(12) United States Patent
Cornelius et al.

(10) Patent No.: US 10,398,601 B2
(45) Date of Patent: Sep. 3, 2019

(54) IMMERSIVE EXPERIENCE HEADSET ADAPTED TO PREVENT FOGGING

(71) Applicant: ABOMINABLE LABS, LLC, Lake Oswego, OR (US)

(72) Inventors: Jack C. Cornelius, Lake Oswego, OR (US); Vincent O'Malley, Portland, OR (US)

(73) Assignee: Abominable Labs, LLC, Lake Oswego, OR (US)

( * ) Notice: Subject to any disclaimer, the term of this patent is extended or adjusted under 35 U.S.C. 154(b) by 11 days.

(21) Appl. No.: 15/959,168

(22) Filed: Apr. 21, 2018

(65) Prior Publication Data

US 2018/0239131 A1    Aug. 23, 2018

Related U.S. Application Data

(63) Continuation-in-part of application No. PCT/US2016/058330, filed on Oct. 22, 2016.
(Continued)

(51) Int. Cl.
*G02B 27/00* (2006.01)
*A61F 9/02* (2006.01)
(Continued)

(52) U.S. Cl.
CPC ............ *A61F 9/025* (2013.01); *A61F 9/02* (2013.01); *A61F 9/027* (2013.01); *A61F 9/029* (2013.01);
(Continued)

(58) Field of Classification Search
CPC . A61F 9/025; A61F 9/029; A61F 9/06; G02B 27/0006; G02B 27/0176; H05B 3/84
(Continued)

(56) References Cited

U.S. PATENT DOCUMENTS 3,012,248 A * 12/1961 Kleinman ............... A61F 9/026
2/436
4,638,728 A   1/1987 Elenewski
(Continued)

OTHER PUBLICATIONS

Best Buy, HTC—Virtual Reality System for Compatible Windows PCs—Black, posted at bestbuy.com, © 2018 Best Buy, [online], [site visted Apr. 9, 2018], 5 pages, available from Internet, <URL: https://www.bestbuy.com/site/htc-virtual-reality-system-for-compatible-windows-pcs-black/5901551.p?skuId=5901551>.

*Primary Examiner* — Ricky D Shafer
(74) *Attorney, Agent, or Firm* — Howard Russell

(57) ABSTRACT

Bus bar electrical interconnection system adapted for use with an irregularly-shaped eye-shield and adapted for interconnection with leads from a battery to power a heating element affixed to the eye-shield, the interconnection system having bus bars, each bus bar adapted for connection with a lead from the battery, one or more of the bus bars having at least one protruding configuration alteration providing a partial contact surface area of the bus bars, and at least one peripheral member securing interconnection of the partial contact surface area of the bus bars with the heating element, for providing customized heating of the heating element depending upon the number of protruding configuration alterations for customized heating to prevent fogging of the eye-shield.

20 Claims, 17 Drawing Sheets

Related U.S. Application Data

(60) Provisional application No. 62/245,904, filed on Oct. 23, 2015.

(51) Int. Cl.
*H05B 3/84* (2006.01)
*G02B 27/01* (2006.01)
*G06T 19/00* (2011.01)
*H05B 1/02* (2006.01)
*A61F 9/06* (2006.01)
*G02C 11/08* (2006.01)

(52) U.S. Cl.
CPC ............ *A61F 9/06* (2013.01); *G02B 27/0006* (2013.01); *G02B 27/0176* (2013.01); *G02C 11/08* (2013.01); *G06T 19/006* (2013.01); *H05B 1/0227* (2013.01); *H05B 1/0252* (2013.01); *H05B 3/84* (2013.01); *H05B 2203/011* (2013.01); *H05B 2203/016* (2013.01)

(58) Field of Classification Search
USPC ......... 359/512; 2/435; 351/62, 158; 219/211
See application file for complete search history.

(56) References Cited

U.S. PATENT DOCUMENTS

| | | |
|---|---|---|
| 4,868,929 A | 9/1989 | Curcio |
| 4,940,884 A | 7/1990 | Gillery |
| 5,351,339 A | 10/1994 | Reuber et al. |
| 5,471,036 A | 11/1995 | Sperbeck |
| 7,648,234 B2 * | 1/2010 | Welchel ................. G02C 11/08 351/62 |
| 8,566,962 B2 | 10/2013 | Cornelius |
| 9,072,591 B2 * | 7/2015 | Cornelius ................. A61F 9/04 |
| 9,210,737 B2 | 12/2015 | Cornelius |
| 9,301,879 B2 | 4/2016 | McCulloch et al. |
| 9,419,520 B2 * | 8/2016 | O'Malley ........... H02M 3/1563 |
| 9,678,367 B2 * | 6/2017 | Cornelius ............... A61F 9/029 |
| 9,693,395 B2 * | 6/2017 | McCulloch ............ A61F 9/029 |
| 9,999,545 B2 * | 6/2018 | McCulloch ............ G02C 11/08 |
| 2002/0044331 A1 | 4/2002 | Agrawal et al. |
| 2008/0290081 A1 | 11/2008 | Biddell |
| 2009/0151057 A1 | 6/2009 | Lebel et al. |
| 2013/0043233 A1 | 2/2013 | Elser et al. |
| 2013/0068495 A1 | 3/2013 | Hadi et al. |
| 2013/0091623 A1 | 4/2013 | McCulloch et al. |
| 2014/0317836 A1 | 10/2014 | McCulloch et al. |
| 2014/0370311 A1 | 12/2014 | Boulord et al. |
| 2015/0121610 A1 | 5/2015 | Cornelius et al. |
| 2018/0045981 A1 * | 2/2018 | Cornelius ........... G02F 1/13306 |
| 2018/0325736 A1 * | 11/2018 | O'Malley ............... A61F 9/025 |

* cited by examiner

IMMERSIVE EXPERIENCE HEADSET ADAPTED TO PREVENT FOGGING

CROSS-REFERENCE TO RELATED APPLICATIONS

This patent application is a continuation-in-part patent application of prior co-pending PCT Patent Application Serial No. PCT/US2016/058330, for ELECTRICAL INTERCONNECTION SYSTEM FOR HEATING EYE-SHIELD, filed 22 Oct. 2016, the PCT patent application having a priority date of 23 Oct. 2015.

FIELD

This invention relates to wearable virtual, enhanced or augmented electronic reality immersive experience headset devices which are worn by users on their heads for facilitating virtual reality, enhanced reality, and augmented reality related activities, and more particularly to such, sometimes fully portable, immersive experience electronic headset devices wearable by users for facilitating such activities, wherein each device comprises a viewing screen adapted for heating, or a lens adapted for heating, to prevent fogging of the viewing screen or lens.

BACKGROUND

Immersive experience headset devices are now available as part of graphics display, sound, haptic and/or other sensory stimulating computing and software systems which provide a user wearing the headset device a certain sensory (visual, aural and/or touch) experience. These headset devices and/or systems also may include laser and/or infra-red detection capability, cameras, and sensors for temperature, humidity, motion, altitude, speed, and the like. These headset devices and systems come in two main varieties. The first of these main varieties of systems comprise virtual reality (V/R) systems wherein a first sub-type of V/R system often, or typically, does not actually involve much physical exertion of oneself by participating in a correspondingly real experience akin to, or correlated with, the sensory experience while using the system. Thus, with such V/R systems the user does not typically engage much in self-motivated, traveling (translational) motion, such as by running along a real sidewalk, by climbing a real mountain, by paddling a real boat, by skiing down a real ski-slope, or by cycling down a real trail or street, etc., even though the user is actually virtually experiencing any one of such activities through the user's visual, aural, and/or other sensory organs. Thus, in such systems the user is usually not part of an actual, real, traveling (translational) experience akin to the sensory experience being provided by the system—except perhaps as may be provided stationed in a vehicle with other automated or protective safety systems in place. Thus, with such V/R systems, not involving a lot of physical exertion, fogging of a vision screen of such a V/R headset has not been as much of a problem, except in cases where the user may transition, for example, from a colder environment to a warmer, more humid, environment, or where a user becomes nervous or anxious, as a result of the experience, thus increasing the heart rate and respiration of the user causing perspiration, wherein fogging of the system could negatively impact the graphics display capability of the system and the visual experience of the user in such a case.

In a second sub-type of V/R system experiences, wherein substantial physical exertion may be, or would be (as to systems still being developed), experienced, such as by swinging the arms as if using a tennis racquet or bat, or the like, while making throwing, punching or climbing motions while standing in place, while engaging in running-in-place-type motions, while using a stationary bicycle to engage in stationary cycling, or while engaging in some other active endeavor while standing or sitting in place, the user's core body temperature may actually be raised. Thus, the user's heart rate and respiratory systems may be taxed (all of course while providing for the physical safety of the user), the user's body temperature may be raised, and this would cause perspiration by the user and associated fogging of the vision screen of the V/R headset device. Such fogging, of course would interfere with the transmission of the graphics display of the device and accordingly would negatively impact the experience of the user of such a device.

As for the other type of immersive experience, there are, or will be, provided enhanced or augmented real experiences via an augmented reality (A/R) system. With such A/R systems, there are provided to the user visual, aural, and/or haptic sensory inputs while the user also actually participates in another real, correlated, experience which may involve extreme human exertion, such as by actually skiing, driving, walking, running, playing, engaging in battle, or other real experience, while simultaneously experiencing enhancing sensory inputs from the A/R system. In such, the A/R system is programmed and designed to enhance or augment the real experience in some way. Thus, such an A/R system provides graphic, sound, haptic and/or other sensory stimulating computing and software system inputs provided to the user in "layered" fashion upon the user's perceptions of the real experience, and in such a way as to not interfere with the real experience, but rather so as to enhance the user's perception, and hence ability to perform, in the real experience. Of course, while such systems involve user translational traveling and motion at times, they have nevertheless been (or would be, regarding such systems still not having been fully developed or commercialized), highly susceptible to fogging of the vision screens or lenses of such systems, and such fogging would negatively impact the experience, and even possibly create an unsafe experience.

There is lacking in the prior art a wearable virtual reality (V/R) or augmented reality (A/R) system adapted for heating, either using an on-board battery, or provided with external power, to prevent fogging of the headset display, wherein a heating element on the lens or viewing screen is connected with an on-board battery or other power source for the system. This is because early systems were primarily V/R systems for stationary use where the user would not expend a lot of energy causing perspiration and excess condensation of such within the V/R headset enclosure. But with the advent of more active gaming and other A/R systems, in addition to such V/R systems, the presentation of fogging conditions is becoming more common.

Thus, virtual reality, enhanced reality, and augmented reality system users, for example V/R or A/R headset users, would in certain instances find it desirable to use virtual reality, enhanced reality and augmented reality systems while engaging in activities which would involve conditions contributing to condensation build-up on a viewing screen or lens of the system, where even momentary impairment of vision by fogging would negatively impact the anticipated experience and would otherwise be problematic and could even be dangerous. When the temperature of such a viewing screen or lens has dropped, or would drop, below a dew-point temperature, i.e., the atmospheric temperature below which water droplets would condense and dew would form, fogging has occurred, or would occur, on the viewing screen or lens.

Thus, for example, an A/R system user would experience fogging of an A/R headset lens, through which they could see variable terrain, as they would be engaged in skiing down a mountain assisted by GPS-oriented map information on a heads-up display portion of the lens. As users would work hard to accomplish the task of skiing down the mountain, their eyes and faces around their eyes would perspire, and combined with other moisture in the air, such would cause that the lens, having been made colder to below a dew point by the exterior environment, would become fogged with condensation on the lens, which would obstruct the user's vision causing a less enjoyable or even unsafe condition.

A common characteristic of such wearable portable lenses or viewing screens is that they would be lightweight enough to be worn on a user's head, and they would be positioned relatively closely to a user's face such that the user's breath and body heat would exacerbate fogging conditions. Examples of fog-prone V/R and A/R systems intended for use during various activities would include a V/R headset for holding a hand-held portable electronic visual display device, such as a smart phone device, up to the user's eyes, or alternatively custom end-user V/R or A/R headsets. While the V/R headsets tend to involve more of an immersive experience with sometimes less physical exertion, A/R headsets may be used while engaging in physical exertion, such as active gaming activities, paintball games, tactical and battlefield related activities, athletic activities, such as downhill skiing, cross-country skiing, snowboarding, snowmobiling, sledding, tubing, ice climbing, rock climbing, hiking, mountaineering, and the like, or for use while engaging in other duties or activities requiring the user to be outside in snowy or other inclement weather conditions conducive to fogging.

Examples of other fog-prone A/R guidance systems would include transparent medical face shields worn to prevent pathogens from getting into the user's mouth or eyes, a transparent face shield portion of a motorcycle or snow-mobile helmet, and eye glasses for use while cycling or playing games. Thus, fogging that impairs vision is a common problem where vision screens or lenses form, or partially form, an enclosure around a user's eyes, especially when such devices are used in colder, or otherwise inclement, weather conditions. To the extent such A/R or V/R systems are truly and completely portable, they would be powered by batteries either on a frame for the system, or carried on the user's person with a wired interconnection between the battery and the system. Other such systems may only be partially portable, perhaps tethered to a computerized V/R system, such as for example a PC gaming system.

There is not known the usage of any active technology to prevent fogging of headset-type A/R or V/R displays, portable or otherwise, in part generally because the problem has not been largely foreseen; such displays are still relatively new commercially speaking, or in some A/R applications still nonexistent, in the marketplace. There have been various active apparatus, including fans and conductive apparatus, devised for use with standard goggles to prevent fogging of the same, but such goggles are quite different than a standard V/R or A/R headset. For one, such goggles are typically designed with venting so as to combat fogging employing airflow readily available and somewhat effective because of fast traveling motion of a user associated with many of the various activities for which such goggles often have been used—i.e., for snowboarding or skiing. Such rapid traveling motion serves to force fresh air into the goggle cavity, which has helped to keep fog at bay. However, such rapid traveling motion is not typical with many, if not most, V/R systems, whereas portable A/R headset systems may involve fast traveling motion, such as skiing or cycling, but the A/R headset systems are still largely being developed for mass commercial use.

With heated-lens goggles, there have been used a layer of polyethylene terephthalate (PET) having a very thin indium-tin-oxide layer, silver nanowires, or other thin-film heater affixed thereto, together with a silver ink or other bus bar of a suitable consistency and thickness applied over the edge of the resistive element heater, so as to make sufficient consistent electrical contact with the resistive element heater, and so as to also provide a thick and substantial enough bus bar element to be able to make a substantial electrical contact through the bus bar.

Thus, as shown in FIG. 1, there have been various conductive apparatus devised for preventing condensation build-up on non-A/R or non-V/R goggle inner lenses, comprising a known device, comprising a rivet 10 and contact 112 for interconnecting such a device's battery with a bus bar 116 painted onto a resistive-element heater (such as for example an Indium-Tin Oxide thin film heating element or a carbon-nano-wire heating element) 108 with a known contact system 100 on a goggle eye-shield lens 102 having comprised a polycarbonate substrate 104 as illustrated in FIG. 1. Thus, the goggle eye-shield lens 102 has comprised a layer of polyethylene terephthalate (PET) 106 having indium-tin-oxide, silver nanowires, or other thin-film heater 108 affixed thereto by a known method of deposition, and having a silver ink bus bar 116 of a suitable consistency and thickness painted over the edge of the resistive element heater 108, so as to make sufficient consistent electrical contact with the resistive element heater, and so as to also provide the thick and substantial enough bus bar element 116 to be able to make contact by putting rivet 110 through the bus bar, the metal contact element 112 in contact with the silver ink bus bar, the resistive element heater 106, and the eye-shield substrate 104. Layering these materials onto a thin goggle eye-shield lens 102 has created a lightweight, transparent eye-shield 102 that has warmed when current has passed through the thin-film heater 108. Passing electrical current through the lead wire 114 to the contact 112 and silver ink bus bar 116 has in turn passed a current through the thin-film heater 108, warming the surface of the lens. The goggle eye-shield substrate 104 may be seen in this instance as providing rigidity so as to enable a sufficiently sturdy and durable connection between a battery (not shown) and the eye-shield heating element 108 through the silver ink bus bar 116 and the metal contact 112.

However, the above-described system, wherein the silver ink needs to be applied over the ITO in a consistent manner so as to make an effective and uniform electrical connection across the length of the goggle eye-shield, has been an inefficient method to make an electrical interconnection system for an eye-shield, and has been more difficult and expensive to implement because it has required additional steps, and thus additional labor and cost, to perform.

Additionally, inserting the rivet 110 through the edge of the layered lens 102 would weaken the integrity of the substrate 104 and silver ink bus bar 116, either of which could crack upon flexion around the rivet hole in the substrate. Further, a silver ink bus bar 116 would be painted on and would not create a strong enough connection point for a lead wire 114 to connect, thus this method would require the use of the contact 112 and rivet 110 to connect the lead wire 114 to the silver ink bus bar 116. Since inserting the rivet 110 would require putting a hole in the substrate 104 and the silver ink bus bar 116, would weaken the integrity of the substrate, this method would introduce cracks, or breakage, of the substrate upon flexion at or around the hole required by the rivet.

Again, there is a lacking in the prior art for an interconnection system to interconnect the battery of a goggle eye-shield, as well as an A/R or V/R headset lens or vision screen, with the resistive-element heater on the lens of such provided in a way so as to be easy to manufacture, involving fewer manually performed steps, so as to be more cost-effective to manufacture, which would provide an optimal electrical interconnection between the heating element and the battery, and which would be readily adaptable for allowing customized tuning of heating of an irregularly-shaped eye-shield, viewing screen or lens substrate, to allow even heating or customized pattern heating of the same.

A perfectly rectangular substrate 200, as shown in FIG. 2, would be less susceptible to hot spots because the current from the battery 214 flows evenly through the ITO 202 between and through the upper and lower bus bars 210, 212. Most A/R and V/R viewing screens, or lenses, however, are of irregular shape (other than square or rectangular), for example being rounded or having a cut-out portion corresponding to resting upon the bridge of a user's nose, so such would be subject to problems of hot spots and also would not provide for easily customizable heating of the viewing screen or lens to allow even heating of the same. Similarly as would be the case with A/R and V/R viewing screens or lenses, goggle eye-shields, such as the eye-shield 500 shown in FIG. 5, have been subject to hot spots in the ITO 502 at a location 522 positioned directly over the cut-out 507 of the eye-shield adapted for sitting upon the bridge of the user's nose; a similarly shaped viewing screen of an A/R or V/R system would likewise be subject to such hot spots, though again there have been no heated A/R or V/R system headset viewing screens or lenses.

The reason for hot spots on irregularly-shaped A/R or V/R vision screen or lens substrates would be because the electrical resistivity between the electrical connections across the resistive elements on each substrate would be greater or lesser at different locations on the substrate such that the amount of electrical current consumed in the areas with less distance between terminal connections would be greater, and the amount of electrical current consumed in areas with greater distance between the terminal connections would be less. Thus, as shown on a theoretical vision screen or lens substrate 500 of FIG. 5, where there would be a bus bar 506 across the top of the brow of the substrate, and a corresponding bus bar 508 across the eye-well portion of the substrate 500 and over the bridge of the cut-out 507 of the eye-shield substrate adapted for resting on the bridge of a user's nose, the distance between the bus bars at locations 513, 515, positioned directly over the user's eyes, would tend to be cooler than the position 517, or area B, positioned directly above the cut-out portion of the eye-shield substrate adapted for resting on the bridge of the user's nose. Again, this is because more current would be used (and wasted) over the bridge of the nose than would be used directly over the eyes, and for similar reasons uneven heating would occur in a similarly designed A/R or V/R irregularly-shaped vision screen substrate or lens substrate.

To overcome fogging conditions, enough power would need to be applied to overcome the fog in the areas with the greatest distance between the terminal connection points, and applying the same amount of power over the smaller areas would cause the smaller areas to overheat, which in turn would waste power (assuming a portable, battery-powered system having more limited power supplies). Because of the irregular shape of A/R and V/R vision screen and lens substrates, these problems would exist whether one is considering resistive-wire applications or resistive-film applications for heating. Thus, the problem would result in limited usefulness of heating of V/R and A/R headset vision screens and lenses.

In one type of V/R and A/R headset, the inner lens or viewing screen comprises separate, dual, substantially-circular inner lenses communicating visually with a split-screen display within the headset system (e.g., as accomplished with a smart phone or other display system attached to or otherwise within the system) such that electronics in the system are used to simulate a 3-D environment visual presentation to the user, as is known in the art. The dual circular inner lenses of such systems would thus be susceptible to fogging, and because of the enclosed nature of the headset, and the fact that in some, if not many, A/R applications there is not a lot of high-speed, translational, traveling movement by the user, but rather active engagement by a user standing, dancing, jumping, or running in place, such that venting of the system, even if venting of such systems had been taught, which it hasn't, would not be all that helpful in reducing fogging, because such would require substantial airflow across the viewing screen or lens. Thus, there needs to be determined a need for active technology for preventing fogging of the inner lenses or vision screens of current V/R and A/R systems.

In another type of A/R or V/R system, there is provided an inner viewing screen, or lens, that is more in the shape of a typical goggle system, wherein there is employed a single inner lens comprising an arched portion over the brow of a user's eyes, and further comprising a cut-out portion corresponding to a portion of the frame of the goggle that rests on the bridge of the user's nose, all similar to the theoretical vision screen shown in FIG. 5.

Standard anti-fogging systems found in prior art goggles, such as are found in U.S. Pat. No. 9,301,879 to McCulloch et al., for Goggle With Easily Interchangeable Lens That Is Adaptable For Heating To Prevent Fogging, would not be ideal alone for either type of A/R or V/R system (dual substantially circular, or having a cutout for the bridge of the user's nose), since as taught in the '879 McCulloch et al. patent, there is provided for the use of a battery-powered resistive heating element (such as ITO, carbon nano-wire, or other heating element technology) deposited on a single goggle lens, and not the ready application of such heating elements for a pair of substantially circular lenses as part of such a split-screen presentation system common to some types of standard A/R and V/R headset systems. Further, the McCulloch et al. system alone may be susceptible to hot spots in the lens directly over the bridge of the nose of a user.

And though U.S. Pat. No. 8,566,962, for PWM Heating System for Eye Shield, to Cornelius, and U.S. Pat. No. 9,210,737, for Multiregion Heated Eye Shield, to Cornelius, teaches a multi-channel, multi-region heated eye shield using PWM, as taught in PCT Patent Application, Serial No. PCT/2016/058330, for Electrical Interconnection System For Customized Heating of an Eye-Shield, to O'Malley et al., it would have been somewhat difficult and more expensive to electrically interconnect and efficiently apply heating elements to circular lenses of a vision screen, such as the aforementioned types of standard A/R or V/R vision screen systems, since not only are the lenses of such systems irregular, being non-rectangular in shape, so as to not as easily permit even heating of the same, but also such lenses are typically smaller than would easily accommodate such a prior art heating element and bus bar application as taught in the aforementioned patents to McCulloch et al., and Cornelius. This, in turn, would make the application of bus bars somewhat more difficult, time-consuming, and therefore less cost-effective to implement for this type of an A/R or V/R system. Further, without tuning of application of heating to such rounded lenses and irregularly-shaped substrates, the heated lenses of such would be susceptible to hot spots, because the electrical resistivity between the electrical connections across the resistive elements on the lenses would be greater or lesser at different locations on the lenses, such that the amount of electrical current consumed in the areas with less distance between terminal connections is greater and the amount of electrical current consumed in areas with greater distance between the terminal connections is less.

Thus, regardless of whether a lens system comprises a dual, substantially circular pair of lenses, or a singular irregularly-shaped lens with a cutout for the user's nose, in order to overcome fogging conditions, enough power would need to be applied to overcome the fog in the areas with the greatest distance between the terminal connection points, causing the smaller areas to overheat, which in turn would waste power. And this problem would be exacerbated in some portable V/R or A/R systems where venting has not been employed, thus enhancing the need for active defogging technology in such systems. Thus, the problem described above relating to more efficiently interconnecting heating elements of such systems with a power source, would result in a limited usefulness of attempting to apply heating to prevent fogging of such system viewing screens.

Other examples of disclosures providing for heating of eyewear lenses include the following: U.S. Pat. No. 4,868,929, to Curcio, for Electrically Heated Ski Goggles, and U.S. Pat. No. 7,648,234, to Welchel et al., for Eyewear with Heating Elements, each comprising an eye-shield with embedded resistive wires operatively connected via a switching device to a power source pack adapted to produce heating of the eye-shield for anti-fog purposes. Neither the Curcio nor Welchel disclosures teach of a bus bar contacting a transparent heating element, such as may be made of Indium-Tin-Oxide (ITO), carbon-nano-wires, or other known heating element material, but rather they teach of interconnection of circuit wires to resistive wires embedded in the lens. Nor do Curcio nor Welchel teach an easier-to-manufacture bus bar interconnection system to achieve customized heating of an irregularly-shaped lens or viewing screen of an A/R or V/R system.

US Patent Application No. 2009/0151057A1 to Lebel et al., for Reversible Strap-Mounting Clips for Goggles discloses use of thin-film heating elements used for heating a goggle eye-shield with a push-button switch for turning on power from a battery carried on an eyewear band or eyewear arm. While Lebel et al. teaches of a transparent, thin-filmed heating element, it does not teach about how the bus bar is connected to the heating element. Nor does Lebel teach an easier-to-manufacture bus bar interconnection system to achieve customized heating of an irregularly-shaped V/R or A/R lens or vision screen. Thus, Lebel would be susceptible to a hot spot over the arched cut-out in the goggle eye-shield of that patent, as described above, where it is adapted to accommodate a user's nose, and using such a device in a limited battery-powered application would unduly discharge the battery and diminish the amount of time a battery would last during a particular use.

U.S. Pat. No. 5,351,339 to Reuber et al., for Double Lens Electric Shield, recognizes the problem of un-even heating where an electroconductive film is deposited on an irregular-shaped visor lens, and it proposes a specific bus bar configuration (electrodes 50 and 60) that addresses the problem of making the distance between electrodes substantially the same for fairly uniform flow of electrical current across the electroconductive film. However, the eye-shield of Reuber is more uniform than that of a typical A/R or V/R headset system lens. Accordingly, the configuration of the electrode bus bars of Reuber would not suffice for the viewing lenses configuration of a typical A/R or V/R headset system. Further, the bus bar of Reuber is connected with a rivet to a larger eye-shield itself, and while this may be somewhat suitable for a visor for a motorcycle helmet, as with Reuber, such attachments to an A/R or V/R headset system would be ineffective in part because of the issue of the additional number of steps and additional cost necessary for manufacture, and in part because of the size of the lenses of an A/R or V/R system may be too small to effectively accommodate such a rivet. Rueber does not teach the use of a physically altered configuration of bus bar having protruding, recessed, or otherwise physically altered portions of a bus bar, which would create partial contact surface areas of the bus bar. Thus, Rueber does not teach a customized heating pattern applicable to a heating element on a substrate, together with a less-costly-to-manufacture clamping, or other mechanized or other engaging, system for holding portions of a bus bar against a thin-film heating element, all while allowing other portions of the bus bar to be out of contact with the heating element, in order to apply a specific heating pattern to a V/R or A/R system to prevent hot spots or to otherwise provide customized heating.

Thus, a problem with prior art heated goggle lenses which have employed electrical heating of the lenses is that of uneven heating over the entire surface of an irregular-shaped lens. Thus, such a problem would also obtain if applied to A/R and V/R system lenses which are manufactured with an irregular shape required to maintain a position close to the face of the wearer. Various general attempts to evenly heat an eye-shield across its entire surface have been made with serpentine wires, or strips of thin-film heating material, included on, or within, eye-shield lenses, as for example in published US Patent Application No. 2008/0290081A1 to Biddell for Anti-Fogging Device and Anti-Fogging Viewing Member, U.S. Pat. No. 4,638,728 to Elenewski for Visor Defroster, and US Published Patent Application No. 2013/0043233A1, to Elser et al., for Device for Active Heating of Transparent Materials.

These references do not teach use of a bus bar interconnection system applied to a wearable, portable V/R or A/R headset viewing screen or lens, let alone teaching such an interconnection system having a physically-altered configuration bus bar allowing partial contact of the bus bar with a transparent heating element for supporting even heating of an irregular-shaped A/R or V/R lens or vision screen, or supporting customized heating of such a lens or vision screen, with a transparent film (such as ITO), carbon-nano-wire, or other heater affixed, or otherwise attached to cover a lens surface. Further these references do not teach such a system combined together with a less-costly-to-manufacture clamping, or other mechanized or other engaging, system for holding portions of the bus bar against the heating element while allowing other portions of the bus bar to be out of contact with the heating element, for applying a specific heating pattern to the lens, to prevent hot spots, or to otherwise provide customized heating, and such has not been taught in the prior art.

U.S. Pat. No. 5,471,036 to Sperbeck for Goggle Defogging System with Transparent Indium-Tin-Oxide Heating Layer Disposed on a Lens provides recognition of the problem of uneven heating of a thin-filmed heating element on a lens over the bridge of a user's nose, and other areas, and provides that "the ITO coating includes an interior heating zone (33) that is electrically isolated form the edge of the inside layer." Further, Sperbeck provides, "the region (48) where the bus bars cross the nose area (41) of the goggle lens is isolated from the interior heating zone (33)." Sperbeck further provides: "As a result, the bus bar only contacts the interior heating zone along the top of the goggle lens and along the bottom of the eye regions (37) of the goggle lens located on either side of the nose area (41)." However, Sperbeck does not teach use of a bus bar interconnection system for use with a V/R or A/R headset system, let alone such an interconnection system having a physically-altered configuration bus bar (as by crimping, bending, serpentining or the like) specifically for the purpose of allowing partial contact of the bus bar with a transparent heating element for supporting even heating of an irregular-shaped eye-shield, or customized heating of such an eye-shield, with a transparent film (such as ITO), or carbon-nano-wire, heater affixed, or otherwise attached, to cover a lens surface. Further, Sperbeck doesn't add a clamping, or other mechanized or other engaging, system to attach portions of such a physically-diverted heating element, enabling specific pattern heating by applying a specific heating pattern to the eye-shield to prevent hot spots, or to otherwise provide customized heating, all in a system that is less costly to manufacture overall than prior-art systems.

In contrast, the bus bars of Sperbeck, make a uniform, smooth-transition path across the path of the lens, and they are not taught to be used in conjunction with a clamping, or other engaging peripheral member for holding only diverted portions of the bus bar against the ITO. Rather, Sperbeck teaches that "The interior heating zone of the ITO coating can be electrically isolated by scoring a groove around the periphery of the ITO coating. Alternatively, acid etching can be used to remove a peripheral part of the ITO coating." Still further, Sperbeck makes use of a prior art, silver ink priming, method of making contact between the ITO coating and the bus bars, stating: "Multiple layers of silver are primed atop the ITO coating . . . ." Sperbeck makes use of a tab 43 and connector 46 for interconnecting the bus bar, leads from the battery, and the ITO on the eye-shield substrate.

In U.S. Pat. No. 9,210,737, for Multiregion Heated Eye Shield, to Cornelius, there is provided an anti-fog eye-shield having an apportioned thin resistive-film heater on the eye-shield to enable even heating of the lens, or other custom heating of the lens, for use in an anti-fog goggle, an anti-fog dive mask or other portable transparent anti-fog eye-protecting shield. In that patent, there is taught apportioning of the heater on the eye-shield with either a split bus bar for each apportioned heating area, or a single bus bar for multiple apportioned heating areas. However, as described above, an altered configuration bus bar presenting partial connection surface areas according to protruding, or otherwise extended, contact areas, is not taught in that patent to Cornelius. Nor is such a system taught in the Cornelius patent combined together with a less-costly-to-manufacture clamping, or other engaging, system for holding portions of the bus bar against the heating element, all while allowing other portions of the bus bar to be out of contact with the heating element. Such a system would be beneficial and cost effective for applying a specific heating pattern to smaller rounded lenses or other irregular viewing screens of newer A/R and V/R system lenses and viewing screens in order to prevent hot spots, or to otherwise provide customized heating, for such systems.

Referring to FIGS. 2-4, a series of general schematic representations of current flow paths is provided and described as background for further description and understanding of the invention and its operation. Referring now specifically to FIG. 2, there is shown a schematic representation of current 204 flowing through a rectangular eye-shield 200 having a thin film-heater 208 attached to a layered lens 202 with an upper bus bar 210 affixed to the entire upper length of the layered lens 202, and a lower bus bar 212 affixed to the entire lower length of the layered lens 202. A battery power source 214 with positive terminal 216 and negative terminal 218 connects to the upper bus bar 210 and lower bus bar 212, using a rivet 224, through a positive circuit wire 220 and a negative circuit wire 222.

If the bus bars 210, 212 are uniformly distributed along the entire upper peripheral length and lower peripheral length of the layered lens 202, and a thin-film heater 208 is also uniformly applied to the surface of the layered lens 202, current 204 will flow uniformly through the thin-film heater 208 to evenly heat the layered lens 202. With a perfect application of the thin-film heater 208 and bus bars 210, 212, the surface of the layered lens will avoid hot spots. However, uniform application is difficult and expensive to achieve. Additionally, a perfectly rectangular eye-shield 200 is impractical because the human face is not flat and rectangular, but is instead curved and intricate.

Referring to FIG. 3, there is shown another schematic representation of current 304, 306 flowing through a transparent thin-film heater 308 of a rectangular eye-shield 300 having a layered lens 302. There is further shown an upper bus bar 310 affixed to a portion less than the entire upper length of the layered lens 302 with gaps or cutouts on both sides of the upper layered lens 302, and a lower bus bar 312 affixed to a portion less than the entire lower length of the layered lens 302 located directly opposite of the upper bus bar 310, with gaps or cutouts on both sides of the lower bus bar 312. A battery power source 314 with positive terminal 316 and negative terminal 318 connects to the upper bus bar 310 and lower bus bar 312 through a positive circuit wire 320 and a negative circuit wire 322.

Because upper bus bar 310 and lower bus bar 312 do not occupy the entire upper and lower lengths of the layered lens 302, currents 304, 306 do not uniformly flow across the layered lens 302. Instead of flowing uniformly across layered lens 302, current 306 bows out into areas of less direct paths creating heating that is not uniform. A warm spot forms in the middle of layered lens 302 where current 304 flows directly, in the shortest path, between upper bus bar 310 and lower bus bar 312. Alternatively, less warm spots form around the outer periphery areas of the eye-shield 300 where current 306 bows out into areas of less direct paths, creating uneven heating. Such uneven heating is undesirable in an eye-shield when dissipating fog or condensation because while the warm spot dissipates fog, the less warm spots might not dissipate fog, leaving a user or wearer of the eye-shield 300 with partially restricted vision. Alternatively, if enough power and current is supplied to the eye-shield 300 in order to dissipate all fog across the entire surface of the eye-shield 300, a hot spot will form where current 304 flows directly between bus bars 310, 312, using unnecessary and excessive amounts of power from battery 314, and lessening the total time a user or wearer can use eye-shield 300.

Referring to FIG. 4, there is shown a schematic representation of current 404, 406 flowing through a transparent thin-film heater 408 of a rectangular eye-shield 400. The rectangular eye-shield 400 comprises a transparent thin-film heater 408 attached to a layered lens 402 with two upper bus bars 410a, 410b spaced apart and affixed to a portion less than the entire peripheral upper length of the layered lens 402 with a gap 412 separating the two upper bus bars 410a, 410b, and a lower bus bar 414 affixed to a portion less than the entire peripheral lower length of the layered lens 402, with gaps or cutouts on both sides of the lower bus bar 414, positioned such that the lower bus bar 414 is offset laterally and directly across from the gap 412 separating the two upper bus bars 410a, 410b. A battery power source 416 with positive terminal 418 and negative terminal 420 connects to the upper bus bars 410a, 410b and lower bus bar 414 through a positive circuit wire 422 and a negative circuit wire 424, supplying power to upper bus bars 410a, 410b, lower bus bar 414, and the transparent thin-film heater 408.

Because upper bus bars 410a, 410b and lower bus bar 414 do not occupy the entire upper and lower lengths of the layered lens 402, and a gap 412 separates bus bars 410a and 410b, currents 404, 406 do not uniformly flow across the layered lens 402. Instead of flowing uniformly across layered lens 402, currents 404, 406 are skewed, flowing diagonally across layered lens 402 from upper bus bars 410a, 410b to lower bus bar 414. Current will mostly flow in straight, direct paths with a higher concentration flowing over the shortest path, however additional current will bow out into areas of less direct paths creating heating that is not uniform. Warm spots form on layered lens 402 where currents 404, 406 flows directly, in the shortest paths, between upper bus bars 410a, 410b and lower bus bar 414. Alternatively, less warm spots form around the outer periphery areas of the eye-shield 300, and near gap 412, where currents 404, 406 bow out into areas of less direct paths, or where the distance traveled by the currents 404, 406 is longer, creating uneven heating. Such uneven heating in this manner is also undesirable in an eye-shield when dissipating fog or condensation, because while the warm spots dissipate fog, the less warm spots might not dissipate fog, leaving a user or wearer of the eye-shield 400 with restricted vision. Alternatively, if enough power and current is supplied to the eye-shield 400 in order to dissipate all fog across the entire surface of the eye-shield 400, hot spots will form where currents 404, 406 flow directly between upper bus bars 410a, 410b and lower bus bar 412, using unnecessary and excessive amounts of power from battery 414, lessening the total time a user or wearer can use the eye-shield 400.

While the above descriptions of current flow through a transparent heating element may have consequences resulting in wasted power and uneven heating if misapplied or misunderstood, intentional use of patterned heating from a bus bar may be advantageously used to tune heating to be more efficient and customized as further described herein.

Referring to FIG. 5, there is shown a graphical representation front view of a prior, irregular-shaped eye-shield 500 comprising a thin-film heater 504 attached to a layered lens 502, an upper bus bar 506 attached to the peripheral upper length of the layered lens 502, and a lower bus bar 508 attached to the peripheral lower length of the layered lens 502. A battery power source 510 with a positive terminal 512 and negative terminal 514 connects to the upper bus bar 506 and lower bus bar 508 through a positive circuit wire 516 and a negative circuit wire 518 attached to the upper bus bar 506 and lower bus bar 508 using rivets 520, supplying power to upper bus bar 506, lower bus bar 508, and the thin-film heater 504.

An irregular shape of an eye-shield 500 is necessary in order to fit the unique curvature and shape of a user's face. However, because of the irregular shape of eye-shield 500, current supplied by the battery power source 510 will not uniformly flow across the layered lens 502. Instead of flowing uniformly across layered lens 502, current will try to flow from upper bus bar 506 to lower bus bar 508 through thin-film heater 504 in the shortest, most direct path. Because of the irregular shape of layered lens 502, the shortest, most direct path occurs in region B 522 above the nose cut-out portion of eye-shield 500, resulting in a warm/hot spot in region B 522 above the nose cut-out portion of the eye-shield. Alternatively, less warm spots form around the outer periphery areas of the eye-shield 500 in regions A and C 524, 526, respectively, where current flows in a longer, or less direct, path from upper bus bar 506 to lower bus bar 508, creating uneven heating of eye-shield 500.

Such uneven heating is undesirable when dissipating fog or condensation, because while the warmth in region B 522 dissipates fog, the less warm spots in regions A and C 524 526 might not dissipate fog, leaving a user or wearer of the eye-shield 500 with partially restricted vision through regions A and C 524, 526, respectively. Alternatively, if enough power and current is supplied to the eye-shield 500 in order to dissipate all fog across the entire surface of the eye-shield 500 in regions A, B and C 524, 522, 526, respectively, a hot spot will form above the nose cut-out of eye-shield 500 where current flows in the shortest, most direct path between upper bus bar 506 and lower bus bar 508. In this way, unnecessary and excessive amounts of power from battery 510 are used, lessening the total time a user or wearer can use eye-shield 500 to dissipate fog.

Referring to FIG. 6, there is shown a graphical representation front view of a prior, split-bus-bar, irregular-shaped eye-shield 600 comprising a thin-film heater 604 attached to a layered lens 602, an upper bus bar 606, made by painting silver ink onto the layered lens 602, attached to the peripheral upper length of the layered lens 602, and two lower, split, bus bars 608a, 608b, also made by painting silver ink onto the layered lens 602, attached to the peripheral lower length of the layered lens 602 and spaced such that there is a gap between them situated at a nose cut-out portion of the eye-shield 600. A battery power source 610 with a positive terminal 612 and negative terminal 614 connects to the upper bus bar 606 and lower bus bars 608a, 608b through a positive circuit wire 616 and a split negative circuit wire 618 attached to the upper bus bar 606 and lower bus bars 608a, 608b, using rivets 620, supplying power to upper bus bar 606 and the lower bus bars 608a, 608b.

The irregular shape of eye-shield 600 is necessary in order to fit the unique curvature and shape of a user's face. Similarly to that described above in connection with FIG. 5, without the region between bus bars 608a, 608b, current supplied by the battery power source 610 would not uniformly flow across the layered lens 602. Instead of flowing uniformly across layered lens 602, current would flow more in the center of the lens where the path is the shortest and most direct, thus causing a hot spot in the center of the layered lens 602.

However, the configuration of bus bars 606, 608a, 608b on the eye-shield, where a silver ink upper bus bar 606 is painted along the entire upper periphery edge of layered lens 602, and where two lower bus bars 608a, 608b are painted along the lower periphery edge of the layered lens, such that there is a gap at the nose cut-out portion of eye-shield 600, creating a more uniform and customized heating of the eye-shield 600 than did previously described eye-shield 500. Eye-shield 600 does not, however, create an ideal situation to uniformly heat layered lens 602 while still conserving power since the bus bars are painted on in a time-consuming, expensive process, and further, eye-shield 600 may be more bulky and cumbersome, needing multiple bus bars and circuit wires to function properly.

Referring to FIG. 7, there is shown a graphical representation front view of a prior, irregular-shaped eye-shield 700 comprising a thin-film heater 704 attached to a layered lens 702. An upper bus bar 706 is attached to the peripheral upper length of the layered lens 702, and a lower bus bar 708 is attached to the peripheral lower length of the layered lens 702. The eye-shield 700 overcomes a limitation of the split bus bar system of eye-shield 600 by providing a slit 703 between lower bus bar 708 and the thin-film heater 704, such that there is no contact between the lower bus bar 708 and the thin-film heater 704 on the layered lens 702 at a location just above the cutout portion of the eye-shield adapted for resting above the bridge of a user's nose. The slit 703 is typically formed by etching, or otherwise cutting, the transparent heating material away from the location of the lens where the bus bar has been applied. A battery power source 710 with a positive terminal 712 and negative terminal 714 connects via the positive terminal to the upper bus bar 706 through a positive circuit wire 716, and connects via the negative terminal to the lower bus bar 708 through a negative circuit wire 718. The upper bus bar 706 and lower bus bar 708 are further attached or connected to the heating element 704 and lens substrate 702 using rivets 720 for supplying power to the upper bus bar 706 and the lower bus bar 708.

As described previously for eye-shield 600, the irregular shape of eye-shield 700 is necessary in order to fit the unique curvature and shape of a user's face. However, because of the irregular shape of eye-shield 700, current supplied by a battery power source 710 would not uniformly flow across the layered lens 702. However, this configuration of bus bars on an eye-shield, similar to that of eye-shield 600, where upper bus bar 706 is along the entire upper periphery edge of layered lens 702, and lower bus bar 708 is situated such that there are two contact areas of bus bar 708 with thin-film heater 708 separated by a slit at the nose cut-out portion of the eye-shield 700, has created a more uniform and customized heating of the eye-shield 700 than did previously described eye-shield 500, and similarly has heated as did eye-shield 600. Like eye-shield 600, however, eye-shield 700 has not created an ideal situation to provide customized, efficient, uniformly applied heat to layered lens 702 while still conserving power.

Referring to FIG. 8A, there is shown a graphical representation front view of a smaller, conceptual circular eye-shield 800, with slitting at 805 similar to that shown and described in connection with FIG. 7, but instead as might be applied to the inner lenses of an A/R or V/R system. Conceptual eye-shield 800 comprises a thin-film heater 804 attached to a layered lens 802, an upper painted silver ink bus bar 806 attached to the peripheral upper length of the layered lens 802, and a lower painted silver ink bus bar 808 attached to the peripheral lower length of the layered lens 802. Presumably, the battery power source 810 with a positive terminal 812, and a negative terminal 814, would connect to the bus bars via a positive circuit wire 816 to the upper bus bar 806, and via a negative circuit wire 818 to the lower bus bar 808 using rivets 820, however it can be seen that the use of such a connection method would be problematic with attempting to place a rivet, which would comprise design and implementation issues on such a smaller substrate surface. Thus, presumably, conceptually, power would be supplied through circuit wires 816, 818 to the upper bus bar and the lower bus bar.

Such a small, circular eye-shield 800 would be desirable where a user desires to achieve a sleek, aerodynamic profile while still protecting their eyes. But because of the small circular shape, current supplied by a battery power source 810 would not uniformly flow across the layered lens 802, but more power would instead flow from upper bus bar 806 to lower bus bar 808 through a thin-film heater 804 in the shortest, most direct path on the outer perimeter of the layered lens where the bus bars are shown closest together. Alternatively, a less warm spot would form in the center of the layered lens 802 where the distance between upper bus bar 806 and lower bus bar 808 would be greatest, which would create uneven heating of the eye-shield 800. Such uneven heating would be undesirable in an eye-shield when dissipating fog or condensation because while the warm regions around the perimeter of the layered lens 802 dissipates fog, the less warm spots in the center region of the layered lens 802 might not dissipate fog, leaving a user with partially restricted vision. Alternatively, if enough power and current is supplied to the eye-shield 800 in order to dissipate all potential fog across the entire surface of the eye-shield 800, hot spots would form in the regions around the perimeter of the layered lens 802 where current flows in the shortest, most direct path between upper bus bar 806 and lower bus bar 808, which would use unnecessary and excessive amounts of power from battery 810, would cause hot spots on the les 802, and would waste power, thus lessening the total time a user or wearer could use the eye-shield 800 to dissipate fog. The implementation of slits 805 as shown is intended to resolve some of the aforementioned uneven heating problem, but overall is not considered an entirely adequate solution for reasons similar to those described in connection with FIG. 7.

Referring to FIG. 8B, there is shown an alternative conceptual embodiment of a graphical representation of a smaller circular eye-shield 850, comprising a thin-film heater 854 attached to a layered lens 852. Layered lens 852 would have painted thereon three silver ink upper bus bars 856a, 856b, 856c attached to the peripheral upper length of the layered lens 852 with gaps separating each of the upper bus bars in split-bus-bar fashion. Layered lens 852 also would have painted thereon three lower bus bars 858a, 858b, 858c attached to the peripheral lower length of the layered lens with gaps separating each of the lower bus bars in split-bus-bar fashion. A battery power source 860 with a positive terminal 862 and negative terminal 864 would connect via a split positive circuit wire 866 to the three upper bus bars 856a, 856b, 856c, and the power source would connect via a split negative circuit wire 868 to the three lower bus bars 858a, 858b, 858c. Attachment of the circuit wires and the bus bars would presumably be through rivets, however it can be readily seen that such would present design and connection problems for so many rivets required on such a small substrate surface.

Just as described previously for eye-shield 800, a small, circular eye-shield 850 is desirable in cases where a user desires to achieve a sleek, aerodynamic profile while still protecting their eyes. Because of the small circular shape, a common current supplied by a single battery power source 860 would not uniformly flow across the layered lens 852, but would instead flow from the upper bus bars 856a, 856b, 856c to lower bus bar 858a, 858b, 858c through a thin-film heater 854 in the shortest, most direct path. Similar to eye-shield 800, in the circular eye-shield 850, the shortest, most direct path would occur near the outer perimeter of the layered lens 852. Alternatively, with a common current power source, a less warm spot would form in the center of the layered lens 852, where the distance between upper bus bars 856b and lower bus bars 858b would be greatest, creating uneven heating of the eye-shield 850. Such uneven heating is undesirable in an eye-shield when dissipating fog or condensation because while the warm regions near the perimeter of the layered lens 852 dissipates fog, the less warm spots in the center region of the layered lens 852 might not dissipate fog, leaving a user with partially restricted vision.

Alternatively, if enough power and current were supplied to the eye-shield 850 in order to dissipate all potential fog across the entire surface of the eye-shield, hot spots would form in the regions around the perimeter of the layered lens 852 where current flows in the shortest, most direct path between upper bus bars 856a, 856c and lower bus bars 858a, 858c, which would use unnecessary and excessive amounts of power from battery 860, lessening the total time a user or wearer could use the eye-shield 850 to dissipate fog. The gaps between upper bus bars 856a, 856b, 856c and lower bus bars 858a, 858b, 858c would help to create a more uniform and customized heating of the eye-shield 850 than would previously described eye-shield 800. Eye-shield 850 would not, however, create an ideal situation to uniformly heat layered lens 852 while still conserving power, though unlike eye-shield 800, some of the failings of eye-shield 850 could be alleviated with a multi-channel power source. Either way, eye-shield 850 might be bulky and cumbersome because it would require multiple positive circuit wires and multiple negative circuit wires, each leading to upper bus bars 856a, 856b, 856c and lower bus bars 858a, 858b, 858c. Adding so many components would also require added expense and time to assemble and may detract from an otherwise desirable sleek design.

Thus, there is needed a bus bar interconnection system which is less labor intensive to manufacture and assemble, and such a system would ideally not require excess wiring or other circuitry.

SUMMARY

In accordance with an aspect of the invention described in priority PCT Patent Application Serial No. PCT/US2016/058330, there is provided an embodiment of a bus bar electrical interconnection system adapted for use with an irregularly-shaped eye-shield substrate and adapted for interconnection with leads from a battery to power a heating element affixed to the eye-shield to provide customized heating to the eye-shield heating element to prevent fogging of the eye-shield. The bus bar electrical interconnection system of this aspect of the invention comprises at least one bus bar, each bus bar comprising means adapted for interconnecting the bus bar with a lead from the battery, such as a rivet on or off of the eye-shield substrate, or other known means of electrical interconnection, each bus bar comprising at least one protruding physical configuration alteration, or protrusion, such as by being crimped, bent, serpentine, or protruded, for providing at least one partial contact area, or surface, of the bus bars or bus bars. This embodiment of this aspect of the invention also comprises at least one peripheral member, or alternatively gluing with a conductive glue together with a frame member, securing interconnection of the partial contact area of the bus bar, or bus bars, with the heating element and adapted for providing customized heating of the heating element depending upon the number of partial contact areas in contact with the heating element and the extent of contact by the partial contact area, or areas, with the heating element for preventing fogging of the eye-shield.

As claimed, the bus bar electrical interconnection system of this aspect of the invention may also provide a plurality of bus bars and may further comprise a battery-powered eye-shield having a heating element thereon. That is, the system may comprise just the bus bar electrical interconnection system alone, or may also include the goggle and/or a battery for the goggle, as well as a strap to hold the goggle on a user's head or helmet. The battery of the battery-powered eye-shield is interconnected with the heating element via the bus bar, or bus bars, of the bus bar electrical interconnection system, and the system may further comprise one or more painted silver ink contact pads located on the heating element, each painted contact pad thus being interposed between at least one of the partial contact areas of the bus bars and the heating element as combined.

The bus bar interconnection system of this aspect of the invention provides custom heating in that a pattern of contact between the bus bar and the heating element may be established that, for example, uses less power because the contacts are uniformly interspersed around the periphery of the eye-shield substrate by uniform spaces between successive protruding portions, as well as between successive receding portions, of the bus bar, or bus bars. Alternatively, those portions of the bus bars that are closest to each other, such as at the cut-out portion of the eye-shield substrate adapted to be positioned directly above a bridge of the user's nose, a nose-bridge portion, when a goggle is worn, or at the furthest extents of the bus bars in the case of opposing (upper and lower, or at each side) bus bars used in a circular configuration eye-shield lens substrate. Such custom heating, then, may provide for more uniform, even, heating of the heating element and the lens substrate. Alternatively, a custom heating profile may entail heating a left side of the goggle, a right side of the goggle, or some other portion of the goggle, without departing from the true scope and spirit of the invention as claimed.

The bus bars of the bus bar interconnection system of this aspect of the invention each have a contacting surface for engaging the heating element of the eye-shield and an opposing non-contacting surface that is not for engaging the heating element of the eye-shield. In accordance with this aspect of the invention, the contacting surface for engaging the heating element of the eye-shield is further provided with a physical configuration alteration, such as a protrusion or recession in the bus bar or bus bars, such that only a portion of the contacting surface area is allowed to engage the heating element at certain pre-defined locations (such as at either or both sides of the nose-bridge portion of the eye-shield while preventing contact of the bus bar, or bus bars, with the heating element of the eye-shield directly above the nose-bridge portion of the eye-shield), the portion being allowed to engage the heating element determining the amount of current to be supplied to the heating element, and at what locations, to provide a customized heating pattern to the eye-shield in accordance with the configuration of the bus bars and the contact engagement member, such as a peripheral member for allowing only certain portions of the bus bar to contact the heating element.

Thus, for example, the contacting surface of each bus bar, or the bus bars, may be provided with different stepped levels so that only a plurality of the most protruding protrusions would contact the heating element, for example in a stepped configuration like separated stepping stones in a path, the contacting surface may be provided with a serpentine configuration such that only an inward most portion is able to contact the heating element. Thus, the partial contacting surface areas of the bus bar, or bus bars, and the clamping or engaging member, may be provided with teeth-like projections such that only a protruding portion, or alternatively an inward most recessed portion, is able to contact the heating element. Or, alternatively, certain areas of a bus bar may be biased forward with springs by the clamping or engaging member, or other means such as by adhering a raised protruding portion to the bus bar, to protrude the contact surface of the bus bar onto the heating element.

The means used to thus alter the physical configuration of the bus bar to provide a partial contact portion of the contact surface area of the bus bar may either provide a uniformly stepped partial contact surface area pattern, a randomly partial contact surface area pattern, or a specifically targeted partial contact surface area pattern (such as on either side of the cut-out portion of the substrate adapted for resting on the bridge of a user's nose to thus avoid a hot spot directly above such cut-out portion). Through experimentation, the user is enabled to select an optimum desired pattern to achieve the customized heating pattern desired for a particularly shaped eye-shield. Thus, the physical configuration alteration of the bus bar may be accomplished by special serpentine or tooth-type design (i.e., a design that is more planar in configuration), bending of the bus bar to create "hills" and "valleys" on the bus bar, or crimping the bus bar to create high areas and low areas on the bus bar.

Thus, the system of this aspect of the invention makes use of a bus bar interconnection system having a physically-altered structure or configuration bus bar allowing partial contact of the bus bar with a transparent heating element, or painted contact pads, for example using silver ink paint, for creating an enhanced and more robust contact (that is resistant to scratching and wear) and supporting even heating of an irregular-shaped eye-shield, or customized heating of such an eye-shield, with a transparent film (such as ITO), carbon-nano-wire, or other type of heating element affixed, or otherwise attached to cover a lens surface. Such a system further preferably comprises a less-costly-to-manufacture clamping, or other mechanized or other engaging, system, or alternatively gluing with a conductive glue together with a frame member, for holding portions of the bus bar, or bus bars, against the heating element while allowing other portions of the bus bar to be out of contact with the heating element, for applying a specific heating pattern to the eye-shield to prevent hot spots, or to otherwise provide customized, or evenly applied, heating, despite an irregular shape of the eye-shield.

This aspect of the invention allows for an eye-shield bus bar interconnection system that is readily capable of quicker and easier installation, build after build, eye-shield after eye-shield, with labor being minimized, by creating a system for snapping together a bus bar interconnection system, for example retained in a gasket mount, and an eye-shield substrate having deposited thereon a resistive heating element and minimal painted silver ink contact pads where necessary. This in turn may avoid some of the expensive, exacting and labor-intensive step of having to paint large bus bars onto the lens substrate over an edge of the heating element followed by fastening a rivet and contact through the bus bar, heating element and lens substrate, replacing it with a simple snap-together structure for later interconnection during a manufacturing process to leads from a battery. This, in turn, saves costs and provides a more reliable connection system that may be customized to prevent hot spots over the nose area and/or to tune the amount of current to be supplied for heating to thus maximize battery life and time-in-use capacity.

In accordance with an embodiment of this aspect of the invention, the plurality of bus bars of the bus bar electrical interconnection system of the invention comprises at least one upper bus bar and at least one lower bus bar, wherein the lower bus bar comprises a protruding configuration alteration so as to be adapted for preventing contact of the bus bar with the heating element of the eye-shield above a nose cut-out of the eye-shield.

Further, the bus bar electrical interconnection system may further comprise one of said bars comprising a plurality of protruding configuration alterations so as to create a stepped partial contact surface area, whether uniform or non-uniform, so as to be adapted for providing a customized amount of power to be supplied to the heating element of the eye-shield in accordance with, and depending upon, the number, extent and location of bus bar protrusions (or conversely recessed areas) allowed to come in contact with the heating element by the clamping, engaging or retaining member. This embodiment of the invention may be used to control the amount of power used by the system or to otherwise customize heating of the eye-shield.

In accordance with another aspect and embodiment of the invention described in priority PCT Patent Application Serial No. PCT/US2016/058330, the bus bar electrical interconnection system bus bars are adapted for interconnection with leads from the battery at a location apart from the eye-shield. Since a more substantial bus bar is able to be used, more substantial than a silver ink painted bus bar, with this aspect of the invention it becomes more possible to interconnect the leads of the battery directly to the bus bar itself, without having to so interconnect these elements by riveting them both to the lens substrate. Such riveting weakens the integrity of the substrate which may crack upon flexion around the rivet hole in the substrate. Riveting, clamping, or screwing may nevertheless be advantageously used in connection with this aspect of the invention to interconnect the bus bar, at a location apart from the eye-shield substrate, with a lead from the battery.

In accordance with these and other aspects of the invention described herein, the means for retaining the bus bars in partial contact with the heating element of the eye-shield may comprise a peripheral channel member, made either of a sturdy and preferably rigid conductive material or a non-conductive material, extending around all or part of the periphery of the eye-shield. In the case where the peripheral member extends around all of the periphery of the eye-shield, it preferably comprises a continuous block-U-shaped channel in cross section. The channel member serves to hold the eye-shield substrate having an affixed heating element coating thereon in contact with those portions of the bus bars protruding so as to be accessible to the heating element. This may be accomplished with corresponding protrusions on the clamping member itself corresponding with lateral non-planar protrusions (hills or valleys) on the bus bar, or aligned with the substrate, heating element and planar serpentine portions of the bus bars in such a way as to hold just the planar protrusions overlapping the heating element in contact with the heating element.

The bus bar electrical interconnection systems of these aspects of the invention may be adapted for use in a snow goggle, a swim goggle, glasses, a motorcycle helmet face shield, a medical face shield, a ballistic-grade goggle or glasses, a portable goggle-type virtual reality system and/or a portable goggle-type augmented reality system as further described below.

In connection with another aspect and embodiment of the invention described in priority PCT Patent Application Serial No. PCT/US2016/058330, there is provided an eye-shield adapted for use with a battery to provide heating to prevent fogging while avoiding hot spots on the eye-shield, comprising: an eye-shield substrate having an outer periphery and adapted for protecting a user's eyes and adapted for defining at least a partially enclosed space between the user's eyes and the eye-shield, a heating element on or otherwise adjacent the eye-shield, and an interconnection system comprising a plurality of bus bars having a plurality of protrusions thereon providing a plurality of partial contact areas on the bus bars, a first interconnection adapted for interconnecting between the leads of the battery and the bus bars, and a second interconnection between the bus bars and the heating element on the eye-shield. The interconnection system is adapted for providing customized heating for the eye-shield depending upon the location, number, and extent of protrusions and partial contact areas, of at least one protruding configuration alteration, of the bus bars, coming in contact with the heating element and providing a partial contact area between the bus bars and the heating element upon interconnection of the bus bars and the heating element by the second interconnecting means. The second interconnection of the eye-shield bus bar interconnection system preferably comprises a peripheral clamping member, or other peripheral channel member, for ensuring interconnection of only the partial contact area of the bus bars with the heating element. Further, there is provided in accordance with this aspect of the invention, a head strap, eye-glass temples or other means (such as a safety suit), for holding the eye-shield on a user's face.

Thus, in accordance with this aspect of the invention, use is provided in an eye-shield of a bus bar interconnection system having a physically-altered structure or configuration bus bar allowing partial contact of the bus bar with a transparent heating element for supporting even heating of an irregular-shaped eye-shield, or customized heating of such an eye-shield, with a transparent film (such as ITO), carbon-nano-wire, or other heating element affixed, or otherwise attached, to cover a lens surface, together with a less-costly-to-manufacture clamping, or other mechanized or other engaging, system for holding portions of the bus bar against the heating element while allowing other portions of the bus bar to be out of contact with the heating element, for applying a specific heating pattern to the eye-shield to prevent hot spots, or to otherwise provide customized heating.

In the first embodiment of this aspect of the invention, the bus bars may be attached to the substrate, as with adhesive, rivet or otherwise, or alternatively the bus bars may be secured in interconnecting relationship with the heating element of the eye-shield substrate with a peripheral clamping type member which would serve to hold the system together and provide that only those portions of the bus bar that have been physically altered so as to be able to make contact with the heating element actually remain in contact with the heating element. The bus bars may contact the heating element by way of a painted-on contact region, pad, or pads, as would be the case with a silver ink painted-on bus bar, located strategically around and adjacent the outer periphery of the eye-shield, at least one of the painted contact pads being in contact with at least one of the bus bars and interposed between the plurality of protrusions and partial contact areas of the bus bars.

In another embodiment of this aspect of the invention, the bus bars are interconnected with leads from the battery by way of a direct clip, screwed-on bracket, rivet or other known method, but attached at a location apart from the eye-shield substrate.

In accordance with this aspect of the invention, the plurality of bus bars comprises at least one upper bus bar and at least one lower bus bar, wherein at least one of the at least one lower bus bar comprises at least one protrusion, also known as a protruding configuration alteration, creating a partial contact area for the at least one of the at least one lower bus bar so as to be adapted for allowing contact of the at least one lower bus bar heating element at either side of a nose-bridge portion of the eye shield while preventing contact of the bus bar with the heating element of the eye-shield directly above the nose-bridge, or other nose cut-out, portion of the eye-shield substrate. That is, for example, on either side of the nose cut-out, or nose-bridge, portion of the eye-shield substrate, the bus bar may be allowed to contact the heating element by combined use of the physically altered structure or configuration of the bus bar and the peripheral member (or conductive gluing). In this way, hot spots over the bridge of the nose cut-out portion are avoided.

Still further, in accordance with this aspect of the invention, the upper bus bar may comprise a plurality of protruding configuration alterations, or protrusions, for providing a partial contact surface area of the bus bars, which may be stepped or evenly dispersed along an outer periphery of the heating element on the eye-shield substrate, customizing the amount and location of application of power to be supplied to the heating element of the eye-shield. This embodiment and feature allows the eye-shield to be fine-tuned as to the amount of power to be delivered to, and to what locations on, the heating element of the eye-shield substrate to minimize wasted battery power. Still further the eye shield of this aspect of the invention may further comprise a plurality of painted contact pads located on the heating element, the contact pads being interposed between the heating element and corresponding location protrusions and partial contact areas of the upper and lower bus bars. Such bus bar and contact pad interconnection allows for lessened losses through a silver ink contact pad as power is distributed to key locations around the periphery of the eye-shield for contact with the contact pads using higher-conductivity bus bars, such as with a copper bus bar.

The eye-shield of this aspect of the invention may be adapted for use in either a snow goggle, a swim goggle, a motorcycle helmet face shield, a medical face shield, an industrial mechanics face shield (i.e., for automotive, welding or other purposes), a ballistic eye-protection eye-shield, a portable goggle-type virtual reality system and/or a portable goggle-type enhanced-reality or augmented-reality system as described further below.

In another embodiment of this aspect of the invention, there is provided a battery-powered eye-shield adapted for preventing fogging of the eye-shield comprising: an irregularly-shaped eye-shield substrate having an outer periphery, a nose cut-out, or nose-bridge, portion, an inner surface, and an outer surface. Further, this embodiment comprises a heating element affixed substantially over an entire portion of the eye-shield substrate's inner surface and a battery with leads for supplying power to heat the heating element to prevent fogging of the eye-shield's substrate. Still further, this embodiment comprises an interconnection system comprising a plurality of bus bars, wherein each bus bar is interconnected with a lead from the battery, and wherein each bus bar is also interconnected with the heating element on the eye-shield. At least one of the bus bars has at least one recession formed therein so as to form at least one corresponding partial contact surface area for allowing contact of the at least one bus bar with the heating element for providing customized heating for the eye-shield based upon the number, extent, and location of the at least one corresponding partial contact area contacting the heating element. The bus bar is held in place by a peripheral interconnecting member, or alternatively by conductive gluing together with a frame member.

Alternatively, preferably, the battery-powered eye-shield of this aspect of the invention further comprises at least one painted contact pad located on the heating element, the contact pads being interposed between at least one of the partial contact areas of the bus bars and the heating element. Such bus bar and contact pad configurations allow for a more robust and enhanced contact between the battery and the heating element, while minimizing possible damage to the heating element, and while providing for an efficient disbursement of power around the periphery of the eye-shield with minimal losses in the circuitry. Further, such a system reduces the cost of manufacturing and assembly of the eye shield.

In the battery-powered eye-shield of this embodiment of this aspect of the invention, the interconnection system comprises at least one upper bus bar and at least one lower bus bar, wherein the lower bus bar is bent to form at least one receding configuration alteration, or recession, such as an out-of-plane hill or valley, or such as a planar serpentine, or angular, configuration, so as to form at least one corresponding partial contact area for allowing contact of the at least one lower bus bar heating element for preventing contact of the at least one bus bar with the heating element of the eye-shield at a location directly above a nose cut-out nose-bridge area of the eye-shield, and wherein the interconnection system further comprises a peripheral channel member securing interconnection of the partial contact area of the bus bars with the heating element.

Still further, in accordance with an embodiment of this aspect of the invention, there is provided a battery-powered eye-shield wherein the interconnection system further comprises at least one upper bus bar and a plurality of lower bus bars. In this embodiment of the invention, the upper bus bar comprises a plurality of bends forming a plurality of receding configuration alterations, or recessions, such as a plurality of hills, valleys, or serpentine portions, providing corresponding stepped partial contact surface areas for allowing contact of the at least one upper bus bar with the heating element for providing customized heating for the heating element of the eye-shield.

Alternatively, in the battery-powered eye-shield of this aspect of the invention, the interconnection system may comprise an upper bus bar and a lower bus bar, wherein at least one protrusion is adhered to the upper bus bar or lower bus bar so as to be adapted to form a partial contact surface area of the bus bar with the heating element of the eye-shield.

Furthermore, in the battery powered eye-shield of this invention, the upper bus bar or lower bus bar may comprise a plurality of protrusions formed, or adhered thereon, forming a plurality of partial contact surface areas providing a stepped partial contact surface area providing a customized amount and location-specific application of power to the heating element of the eye-shield.

Still further, an embodiment of the battery-powered eye-shield of this aspect of the invention comprises an upper bus bar and a plurality of lower bus bars, wherein the bus bars each has a plurality of protrusions or recessions formed therein so as to form corresponding partial contact areas for allowing contact of the bus bars with the heating element. This embodiment further comprises at least one painted contact pad located strategically adjacent the outer periphery of the heating element, the at least one painted contact pad being interposed between the partial contact areas of the bus bars and the heating element so as to provide an enhanced contact and for customized location-specific power from the battery to the heating element via the bus bars. Alternatively, the upper bus bar and the lower bus bars of this embodiment of this aspect of the invention are interconnected with the heating element via the plurality of painted contact pads at strategic locations around the outer periphery of the eye-shields to further provide even heating of the eye shield.

These embodiments of this aspect of the invention provide an eye-shield that is less costly to manufacture and which is unique in being able to be heated evenly, or in another customized fashion, because of a unique physical configuration alteration (protrusions, recessions, bends, crimps, serpentines, etc.) of the bus bar and it's resulting contact pattern on the periphery of the transparent heating element affixed to the eye-shield substrate. Such bus bars may either be affixed to the eye-shield substrate or otherwise ensured in their connection to the heating element on the eye-shield substrate with a peripheral member clamping, or otherwise retaining or holding, the bus bars onto the eye-shield heating element to allow only protruding, or otherwise physically diverted, portions of the bus bar to be held in contact with the heating element. This, in turn, provides an eye-shield that is able to avoid hot spots, for example over the cut-out bridge of the eye-shield substrate adapted for resting on the nose of a user, and is also able to be customized in its power delivery to provide optimum heating and minimized battery power waste. Such results may be determined using a heat sensing camera to examine lenses with different heating pattern configurations in accordance with the construction described above.

In accordance with another aspect and embodiment of the invention described in priority PCT Patent Application Serial No. PCT/US2016/058330, there are further provided at least one, and in other embodiments a plurality, of painted contact pads preferably located around the periphery of the heating element on the eye-shield. Thus, there are provided bus bar interconnection systems, an eye-shield adapted for heating using a battery, and also a battery-powered eye-shield, wherein the interconnection system of the bus bar interconnection system comprises at least an upper bus bar and a lower bus bar, and in another embodiment an upper bus bar and a plurality of lower bus bars, wherein the bus bars each has a plurality of protrusions, or alternatively recessions, formed therein so as to form corresponding partial contact areas for allowing contact of the bus bars with the heating element of the eye-shield.

Such a system in accordance with this aspect and these embodiments of the invention further comprise at least one painted contact pad, or in an alternate embodiment a plurality of contact pads, located strategically adjacent and around the outer periphery of the heating element, the painted contact pads being interposed between the partial contact area, or areas, of the bus bars and the heating element so as to provide an enhanced contact area and for customized location-specific power from the battery to the heating element via the bus bars, to provide even heating of the heating element and to avoid hot spots on the eye-shield.

The enhanced painted contacts pads of this aspect of the invention may be provided via a silver ink painted contact pad or other painted or otherwise applied contact. In a silver ink painted contact pad embodiment, silver ink is painted onto the heating element so as to make contact with the heating element, the silver ink being more robust than the heating element material itself so as to avoid damage to the heating element by scratching from the bus bar. This in turn makes for a robust and durable contact, and contact may be reinforced as in other embodiments of the invention with the use of a clamping, or otherwise engaging, peripheral channel member securing interconnection of only the partial contact areas of the bus bars with the heating element. The painted contact pads of this aspect of the invention may be larger or smaller, depending upon the customization needs for heating of the particular area of the eye-shield lens and associated heating element. Thus, for example where less heat is required, as for example directly over the bridge of the nose of a goggle-shaped eye-shield, the painted contact pads may be smaller and just on either side of the nose-cut-out portion of the eye-shield, whereas directly underneath the location of the eye-shield adapted to be directly in front of the eyes of a user, the painted contact pad may be longer in order to allow greater, more dense, power and heating of the eye-shield at that location.

In accordance with another aspect of the invention, there is provided an electronic headset device adapted for being worn by a user of a virtual reality or augmented reality system and adapted for being powered by a power supply to provide at least a visual sensory experience for the user, wherein such a visual sensory (and auditory or other sensory) experience may be computer generated using laser and/or infra-red detection capability, cameras, and sensors for temperature, humidity, motion, altitude, speed, and the like. The device of this aspect of the invention comprises: a frame adapted for housing electronics and circuitry necessary for transmitting images to the user, the frame forming at least a partial enclosure around the user's eyes. There is further provided held in the frame a vision screen having inner and outer surfaces adapted for displaying the images to the user, and there is also provided a heating element attached to a surface, preferably the inner surface, of the vision screen. The heating element on the vision screen is interconnected with the power supply using an electrical interconnection system adapted for such interconnection to enable activation of the heating element to prevent fogging of the vision screen. And there is also provided a support system depending from the frame for holding the headset device, including its frame, vision screen, and heating element, on a user's head a distance from the user's eyes.

In accordance with another embodiment of this aspect of the invention, the vision screen of the electronic headset device of this aspect of the invention further comprises a plurality of generally circular lenses adapted for displaying the images to the user, wherein the heating element on the vision screen comprises a plurality of heating elements, at least one heating element on each of the plurality of lenses, and wherein the electrical interconnection system is adapted for interconnecting each of the heating elements and the power supply.

Preferably the electrical interconnection system of the electronic headset device in accordance with this aspect of the invention further comprises a bus bar electrical interconnection system adapted for interconnection of the heating element and the power source. In this embodiment, the bus bar electrical interconnection system further preferably comprises a plurality of bus bars, each bus bar comprising means adapted for interconnecting the bus bar with a lead from the power source, at least one of the bus bars comprising at least one protruding configuration alteration providing a partial contact surface area of the bus bars. Further, each bus bar electrical interconnection system of this aspect of the invention further preferably comprises at least one peripheral member, preferably a snap-fit channel member, securing interconnection of the partial contact surface area of the bus bars with said heating element so as to be adapted for providing heating to the heating element for preventing fogging of the vision screen.

Still further, preferably in accordance with this aspect of the invention, the electrical interconnection system of the electronic headset device may further comprise a plurality of bus bar electrical interconnection systems adapted for interconnecting the plurality of heating elements and the power source. In this embodiment, each bus bar electrical interconnection system further comprises a plurality of bus bars, each bus bar comprising means adapted for interconnecting the bus bar with a lead from the power source, at least one of the bus bars comprising at least one protruding configuration alteration providing a partial contact surface area of the bus bars. Further, in this embodiment, each bus bar electrical interconnection system further comprises at least one peripheral member, for example a snap-fit cross-section channel member, securing interconnection of the partial contact surface area of the bus bars with at least one of the heating elements, and adapted for providing customized heating to the heating element depending upon the number of protruding configuration alterations in the at least one of the bus bars for preventing fogging of the vision screen.

In another embodiment of this aspect of the invention, pertaining to a single vision screen embodiment of the invention, at least one of the bus bars of the electronic headset device comprises a plurality of protruding configuration alterations so as to create a stepped partial contact surface so as to be adapted for providing a customized amount of power to be supplied to the heating element of the vision screen. Where the vision screen of the headset device comprises a plurality of circular lenses, there is provided at least one of the bus bars comprising a plurality of protruding configuration alterations so as to create a stepped partial contact surface so as to be adapted for providing a customized amount of power to be supplied to the heating element of the vision screen or screens (lenses).

The electronic headset device of this aspect of the invention may comprise a goggle adapted for use during an augmented reality experience, wherein the goggle lens comprises the vision screen, for example as part of a heads-up display on a ski goggle. The headset device of this aspect of the invention may comprise part of a face shield and motor-cycle helmet combination adapted for use during an augmented reality/heads-up display experience, wherein the face shield comprises the vision screen, for example as part of a heads-up display on a motorcycle helmet visor. The headset of this aspect of the invention may comprise part of a medical face shield adapted for use during an augmented reality experience, wherein the face shield comprises the vision screen, for example as part of a heads-up display on a medical face shield. Or, the headset of this aspect of the invention may comprise part of ballistic eyewear adapted for use during an augmented reality experience, wherein the ballistic eyewear has a lens comprising the vision screen, for example as part of a heads-up display in tactical eyewear.

This aspect of the invention provides for heating of an electronic headset device as part of a virtual reality, enhanced reality, and/or augmented reality, system, adapted in one embodiment for heating by a heating element connected to an external power source via system wiring to the headset from a conventional power source, such as an A/C outlet, or from another external power supply, a power supply worn on the user's body, or other external power source, whether the power source is a separate or integral part of a computing device, such as a PC computer or a gaming system.

In another embodiment of this aspect of the invention, the electronic headset device may be part of a more portable, for example augmented reality (A/R) system, where heating is accomplished by a heating element connected to a battery on-board the headset device. Such a device is capable of preventing fogging of the A/R system to provide for a more enjoyable and safe experience for the user.

Thus, in accordance with this aspect of the invention, power may be supplied to the headset device to prevent fogging from negatively impacting the immersive virtual reality, or augmented reality, experience by limiting vision of the user while engaging in activities during the experience. With today's virtual reality systems, active use by a user during gaming, etc., has led to fogging of the electronic headset devices of such systems, and this aspect of the invention actively addresses such fogging, even though there is less ventilation in such a headset, unlike a typical ski-goggle for example, where the user travels speedily across the snow causing ventilation to flow through vents in such ski goggles. By contrast, today's V/R headsets do not contain similar vents, because such translational motion is not typically encountered—and thus neither has fogging of such been anticipated.

Further, a user is enabled, in accordance with this aspect of the invention, in preventing fogging of an electronic headset capable of displaying images to the user for an augmented reality system, such as with a ski goggle, or a tactical goggle, possessing electronic heads-up display capability showing mapping, GPS directions, temperature, altitude, speed, or other tactical or performance-enhancing information, with power to the headset being supplied either via a battery system worn on the user's body, or alternatively from a battery system worn on the headset device itself. Thus, this embodiment of this aspect of the invention is more portable than it would be if it were tethered to a fixed power supply that is part of a computing device, or with AC power, for example.

In accordance with another aspect of the invention, there is provided an electronic headset device adapted for being worn by a user of a virtual reality or augmented reality system, wherein the device and/or system also may include laser and/or infra-red detection capability, cameras, and sensors for temperature, humidity, motion, altitude, speed, and the like, such headset device being adapted for being powered by an on-board battery power supply to provide at least a visual (but also in some cases an aural, haptic, or other) sensory experience for the user. This embodiment of this aspect of the invention comprises: a frame adapted for housing electronics and circuitry necessary for transmitting images to the user, the frame forming at least a partial enclosure around the user's eyes. In the frame there is held a vision screen adapted for displaying the images to the user, and attached to a surface of the vision screen there is a heating element. Further, there is provided an electrical interconnection system adapted for interconnecting the heating element and the power supply to enable activation of the heating element to prevent fogging of the vision screen. The electrical interconnection system comprises a plurality of bus bars, at least one of the bus bars having at least one protruding configuration alteration providing a partial contact surface area of the bus bars on the heating element. The bus bars, and in particular the protruding configuration alteration bus bar or bus bars, are adapted for providing customized heating for the vision screen depending upon the location, number, and extent of protrusions, of the at least one protruding configuration alteration of the bus bars coming in contact with the heating element. The electrical interconnection system further comprises at least one peripheral member securing interconnection of the partial contact surface area of the bus bars with the at least one heating element. There is also provided in connection with this embodiment of this aspect of the invention, a support system depending from the frame for holding the electronic headset device, including but not limited to the frame, the vision screen, and the heating element, on a user's head a distance from the user's eyes.

The electronic headset of this aspect of the invention enables a user in experiencing either a V/R or an A/R experience to its fullest, without being hampered or endangered by fogging. Since this aspect of the invention provides for a more portable system, the user is able to enjoy a fog-free experience, without being tethered to an external power source. Thus, whether the user is engaged in a V/R experience, which may be more totally immersive then an A/R experience, but which nevertheless involves less translational movement, and thus may actually be more susceptible to fogging, or whether engaged in an A/R experience, wherein ventilation may be employed more effectively, the user is supported in a fog-free virtual, or augmented, reality experience.

In accordance with another embodiment, and another aspect, of the invention, there is provided a heated electronic headset device, as part of a virtual, enhanced, or augmented reality system, wherein such a system may include laser and/or infra-red detection capability, cameras, and sensors for temperature, humidity, motion, altitude, speed, and the like, the electronic headset device having a vision screen, or lenses, having a heating element and heating interconnection system comprising a plurality of bus bars for interconnecting with the heating element. In this embodiment and aspect of the invention, at least one of the bus bars comprises a plurality of protruding configuration alterations so as to create a stepped partial contact surface so as to be adapted for providing a customized amount of power to be supplied to the heating element of the vision screen.

Preferably, in accordance with an embodiment of this aspect of the invention, the electronic headset device further comprises at least one upper bus bar and at least one lower bus bar. Further, the upper bus bar of this embodiment and aspect of the invention may further comprise a plurality of protruding configuration alterations for providing a stepped partial contact surface area of the bus bars for customizing the amount of power to be supplied to the heating element of the vision screen.

The electronic headset device of this aspect of the invention may comprise a goggle adapted for use during an augmented reality, or heads-up display, experience, wherein the goggle lens comprises the vision screen, for example as part of a heads-up display of GPS information on a ski goggle, or as part of a presentation system for displaying and exploring a new model of a vehicle. The headset device of this aspect of the invention may comprise part of a face shield and motor-cycle helmet combination adapted for use during an augmented reality experience, wherein the face shield comprises the vision screen, for example as part of a heads-up display on a motorcycle helmet visor, or as part of a high-performance aircraft helmet visor. The headset of this aspect of the invention may comprise part of a medical face shield adapted for use during an augmented reality experience, wherein the face shield comprises the vision screen, for example as part of a heads-up display on a medical face shield for presenting steps for performing particular procedure. Or, the headset of this aspect of the invention may comprise part of ballistic eyewear adapted for use during an augmented reality experience, wherein the ballistic eyewear has a lens comprising the vision screen, for example as part of a heads-up display in tactical eyewear. The preceding examples of applications of the system are meant to be exemplary, not exhaustive. It will be appreciated by those skilled in the art that there are other A/R and V/R applications where the invention may be utilized without departing from true scope and spirit of the invention.

Thus, in accordance with an embodiment of this aspect of the invention, there is provided an electronic headset device adapted for being worn by a user of a virtual reality or augmented reality system to provide at least a visual sensory experience for the user, and the device comprises a frame adapted for housing electronics and circuitry necessary for transmitting images to the user, the frame also housing laser and/or infra-red detection capability, cameras, and sensors for temperature, humidity, motion, altitude, speed, and the like. The frame of also forms at least a partial enclosure around the user's eyes. Further there is provided, in accordance with this embodiment and aspect of the invention, a plurality of circular vision screen lenses held in the frame and adapted for displaying images to the user. On one of an inner or an outer surface (relative to the user's face), preferably an inner surface (which may be covered with a protective layer), of each vision screen lens, there is preferably provided, at least one heating element attached, thus comprising a plurality of heating elements. This aspect and embodiment of the invention further comprises a plurality of electrical interconnection systems, each of the electrical interconnection systems adapted for heating one of the heating elements, each of the electrical interconnection systems comprising a plurality of bus bars, at least one of the bus bars having at least one protruding configuration alteration providing a partial contact surface area of the bus bars on the heating element, each of the electrical interconnection systems comprising at least one peripheral member securing interconnection of the partial contact surface area of the bus bars with the heating element. Further, this aspect and embodiment of the invention comprises a support system depending from the frame for holding the headset device, including the frame, the vision screen lenses, and the heating elements, on a user's head a distance from the user's eyes.

Further, with the electronic headset device of this embodiment and aspect of the invention, at least one of the bus bars may comprise a plurality of protruding configuration alterations so as to create a stepped partial contact area so as to be adapted for providing a customized amount of power to be supplied to one of the heating elements of the vision screen lenses.

Still further, there may be provided in accordance with an embodiment and aspect of the invention, an electronic headset device further comprising at least one painted contact pad, the at least one painted contact pad being located on one of the heating elements, the at least one painted contact pad being interposed between the stepped partial contact area of the at least one of the bus bars and a heating element.

The embodiments of the electronic headset of this aspect of the invention enable a user in experiencing either a V/R or an A/R experience to its fullest, without being hampered or endangered by fogging. Since this aspect of the invention provides for a more portable system, the user is able to enjoy a fog-free experience, without being tethered to an external power source. Thus, whether the user is engaged in a V/R experience, which may be more totally immersive then an A/R experience, but which nevertheless involves less translational movement, and thus may be even more susceptible to fogging in some cases, or whether engaged in an A/R experience, wherein ventilation may be employed more effectively, the user is nevertheless supported in a fog free virtual, or augmented, reality experience.

As with other aspects and embodiments of the invention, the electronic headset device of this aspect of the invention may comprise a goggle adapted for use during an augmented reality experience, wherein the goggle lens comprises the vision screen, for example as part of a heads-up display with weather, temperature, speed, GPS map information, etc., on a ski goggle. The headset device of this aspect of the invention may comprise part of a face shield and motorcycle, or snowmobile, helmet combination adapted for use during an augmented reality experience, wherein the face shield comprises the vision screen, for example as part of a heads-up display on a helmet visor. The headset of this aspect of the invention may comprise part of a medical face shield adapted for use during an augmented reality experience, wherein the face shield comprises the vision screen, for example as part of a heads-up display on a medical face shield. Or, the headset of this aspect of the invention may comprise part of ballistic eyewear adapted for use during an augmented reality experience, wherein the ballistic eyewear has a lens comprising the vision screen, for example as part of a heads-up display in tactical eyewear.

Thus, in accordance with the aforementioned aspects of the invention, the provision of an interconnection system, or a plurality of interconnection systems, each having a physically-altered structure or configuration bus bar allowing partial contact of the bus bar with a transparent heating element, or painted contact pads, for example using silver ink paint, allows and enables the creating of an enhanced and more robust contact (that is resistant to scratching, cracking, and wear). Further, thus, a system of contacts is provided that supports even heating of an irregular-shaped vision screen, or customized heating of such a vision screen, with a transparent film (such as ITO), carbon-nano-wire, or other, heating element affixed, or otherwise attached, to cover a lens surface. Such a system is cheaper to manufacture, in part because such interconnection systems preferably comprise a less-costly-to-manufacture clamping, channel, or other mechanized or other engaging, system. Or, alternatively the interconnection may be accomplished by gluing with a conductive glue, together with a frame member, for holding portions of the bus bar, or bus bars, against the heating element while allowing other portions of the bus bar to be out of contact with the heating element. This, in turn allows for application of a specific heating pattern to the vision screen to prevent hot spots, or to otherwise provide customized, or evenly applied, heating, despite an irregular shape of the vision screen.

These latter aspects of the invention including novel interconnection systems allow for a vision screen bus bar interconnection system that is readily capable of quicker and easier installation, build after build, vision screen after vision screen, with labor being minimized, by creating a system for snapping together a bus bar interconnection system, for example retained in a gasket mount, and a vision screen substrate having deposited thereon a resistive heating element and minimal painted silver ink contact pads for contact with portions of a bus bar. This in turn may avoid some of the expensive, exacting and labor-intensive step of having to paint larger bus bars onto the lens substrate over an edge of the heating element, followed by fastening a rivet through the bus bar, a metal contact pad, the heating element and the lens substrate, replacing these with a simple, preferably snap-together, structure for later interconnection during a manufacturing process, to leads from a battery. This, in turn, saves costs and provides a more reliable connection system that may be customized to prevent hot spots over the nose area and/or to tune the amount of current to be supplied for heating to thus maximize battery life and time-in-use capacity.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings wherein like reference characters refer to like elements.

DETAILED DESCRIPTION

Figure 1:
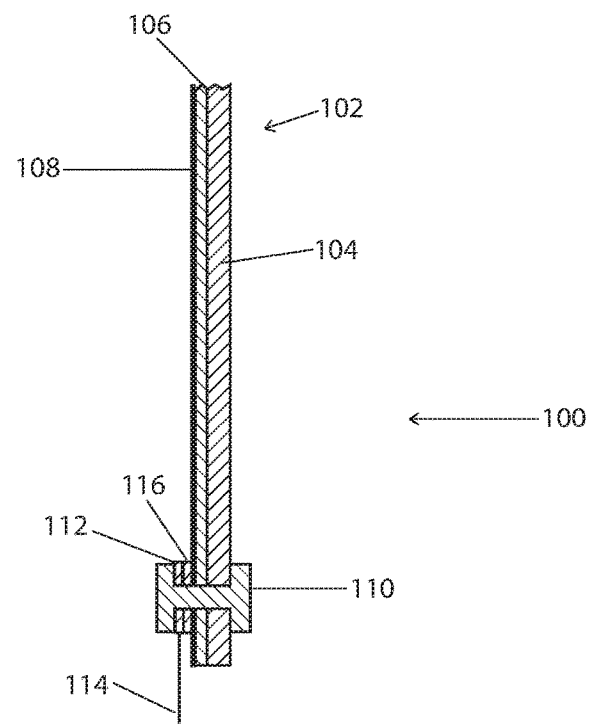
FIG. 1 is a partial cross-section view of a prior silver-ink bus bar electrical interconnection system for a non-A/R or non-V/R lens or eye-shield substrate.
Figure 2:
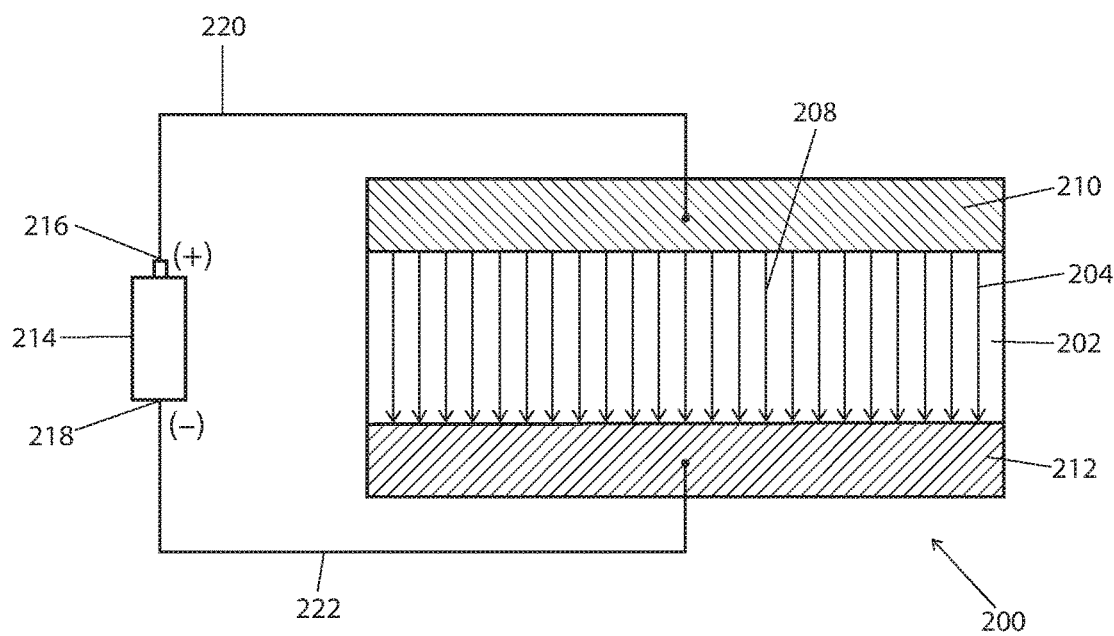
FIG. 2 is a schematic representation of current flow through a transparent heating element on a rectangular non-A/R or non-V/R substrate having upper and lower bus bars across the entire substrate.
Figure 3:
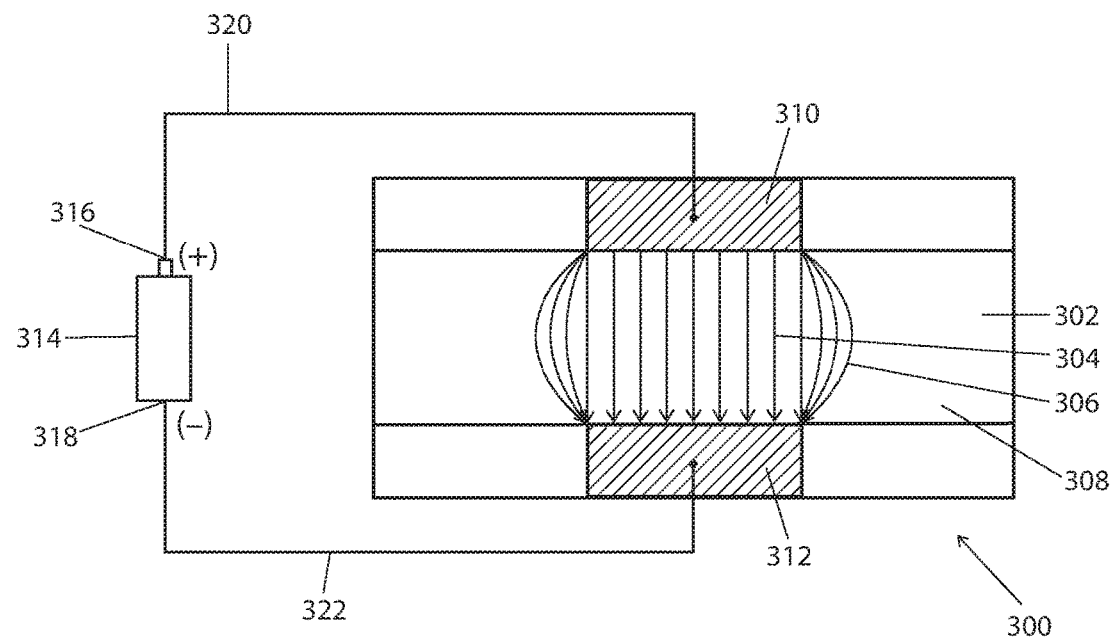
FIG. 3 is another schematic representation of current flow through a transparent heating element on a rectangular non-A/R or non-V/R substrate having central, symmetrically-opposed, partial upper and lower bus bars.
Figure 4:
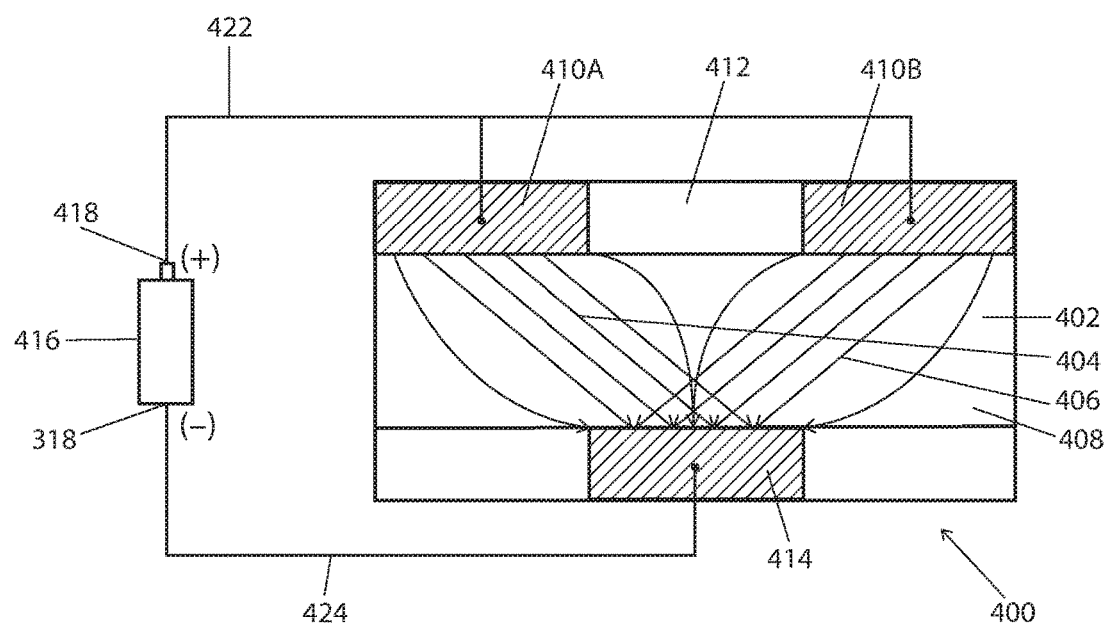
FIG. 4 is yet another schematic representation of current flow through a transparent heating element on a rectangular non-A/R or non-V/R substrate having two upper bus bars and a single offset lower bus bar.
Figure 5:
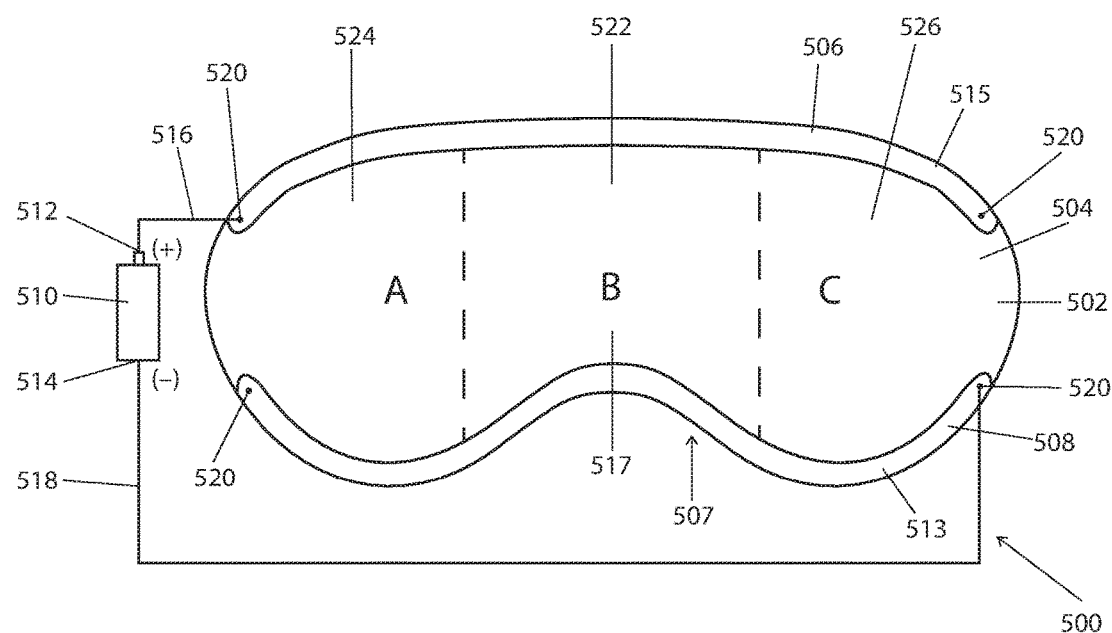
FIG. 5 is a graphic representation front view of a prior non-A/R or non-V/R eye-shield substrate having a silver-ink bus bar electrical interconnection system that is prone to a hot spot over the nose bridge portion of the substrate.
Figure 6:
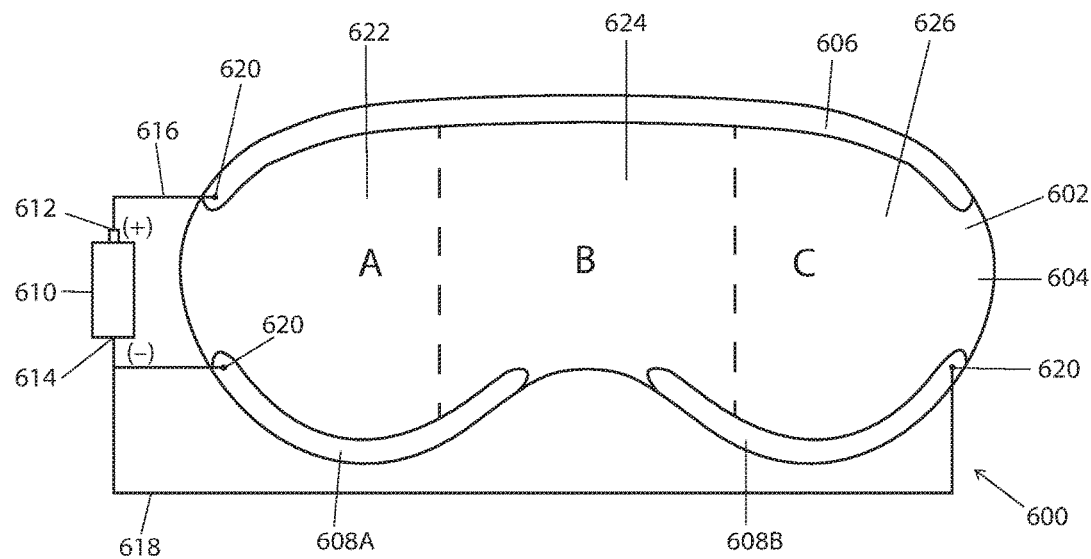
FIG. 6 is a graphic representation front view of another non-A/R or non-V/R eye-shield substrate having a silver-ink bus bar electrical interconnection system which attempts to avoid a hot spot on the substrate over the nose bridge portion of the substrate with a split bus bar system.
Figure 7:
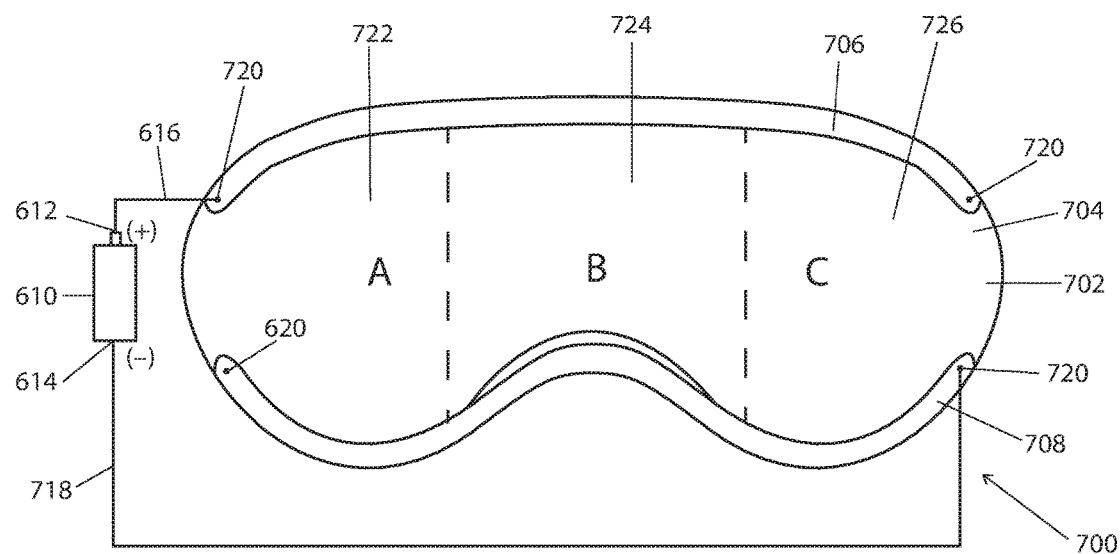
FIG. 7 is a graphic representation front view of a prior non-A/R or non-V/R eye-shield substrate having a silver-ink bus bar electrical interconnection system which attempts to avoid a hot spot on the eye-shield over the nose bridge portion of the eye-shield by slitting the ITO just above the nose bridge portion of the substrate.
Figure 8A:
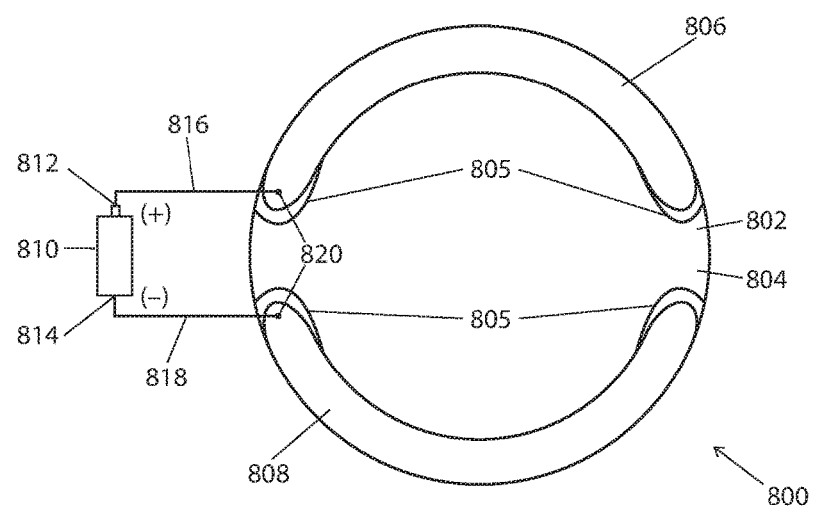
FIG. 8*a* is a graphic representation front view of a smaller circular non-A/R or non-V/R eye-shield substrate having a prior silver-ink bus bar electrical interconnection system using ITO-slitting to prevent overheating of portions of the substrate while preventing fogging.
Figure 8B:
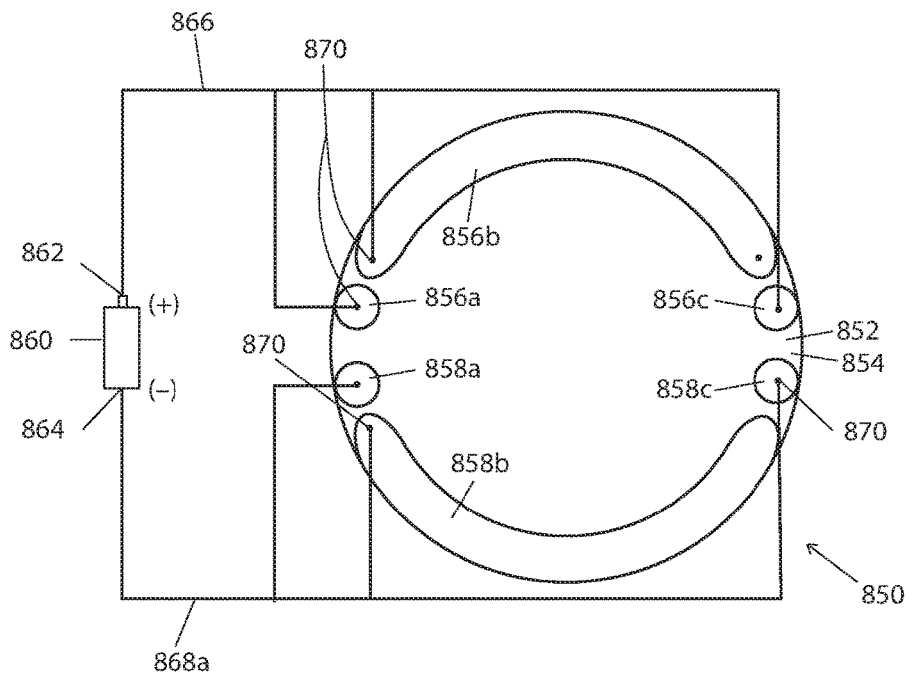
FIG. 8*b* is a graphic representation front view of a smaller circular non-A/R or non-V/R eye-shield substrate having an alternate prior silver-ink bus bar electrical interconnection system using bus bar splitting to prevent overheating of portions of the substrate while preventing fogging.
Figures 9A, 9B:
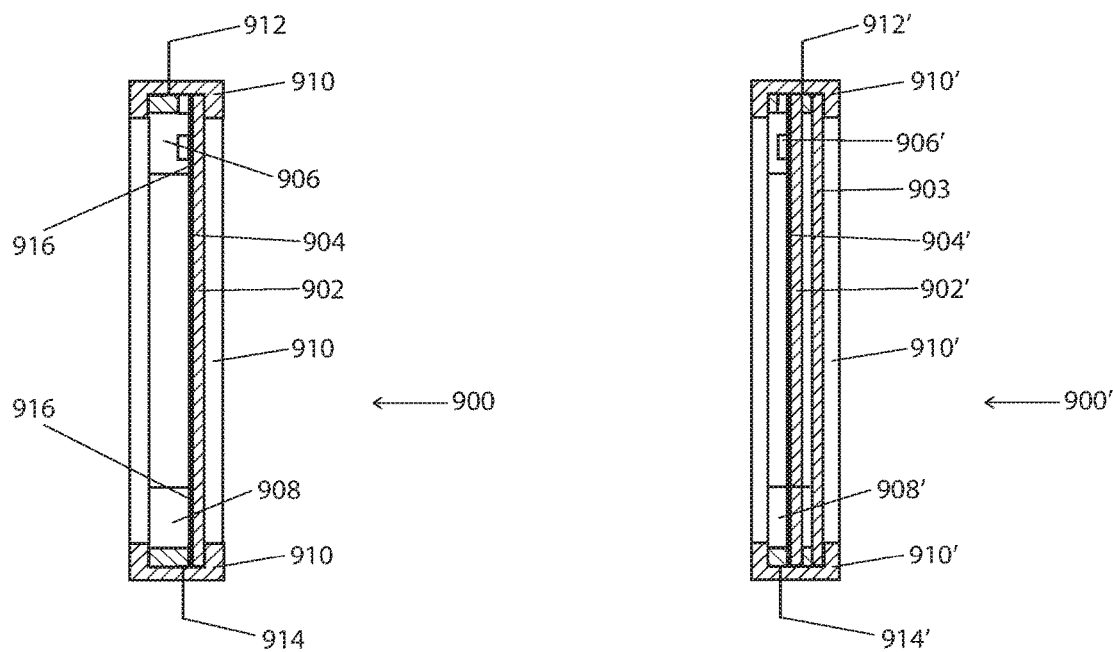
FIG. 9*a* is a cross-section side view of part of an A/R or V/R substrate embodiment shown in FIG. 11 having a bus bar electrical interconnection system in accordance with an aspect of the invention for customized heating to prevent hot spots and fogging of the substrate.
FIG. 9*b* is a cross-section side view of part of an alternative A/R or V/R substrate embodiment similar to that of FIG. 9*a*, but having an additional lens for achieving dual-pane insulation benefits.
Figure 11:
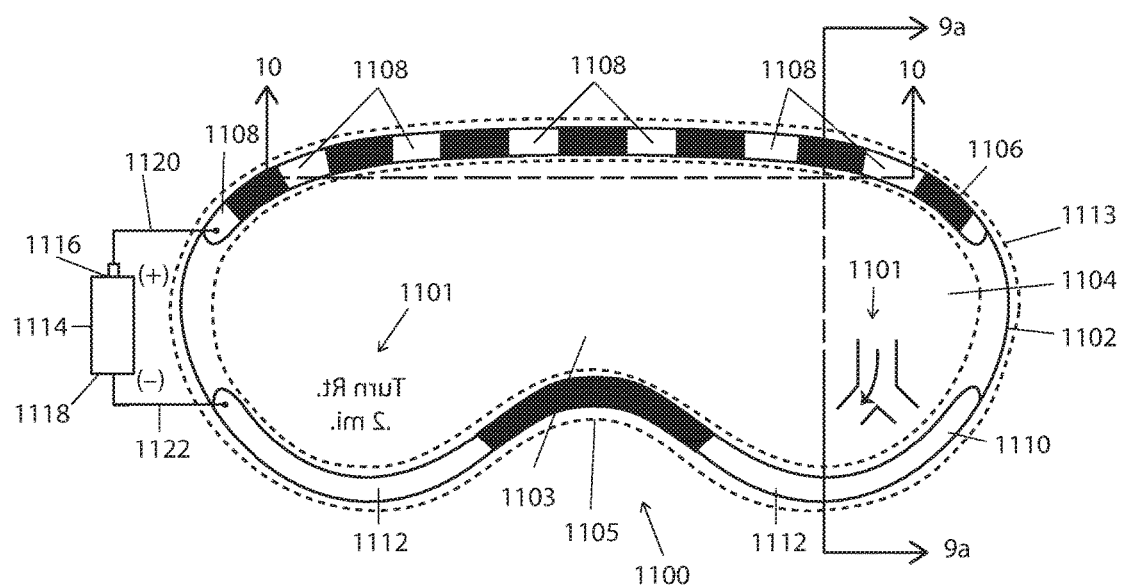
FIG. 11 is a graphic representation of a front view of part of an alternate bus bar electrical interconnection system in accordance with an aspect of the invention for customized efficient and tuned heating to avoid hot spots and prevent fogging of an A/R or V/R substrate.

Referring to FIG. 9a, there is shown a cross-section side view, taken along line 9a-9a of FIG. 11, of a flattened embodiment of a bus bar electrical interconnection system on an augmented reality (A/R) or virtual reality (V/R) eye-shield, or vision screen, 900 in accordance with an aspect of the invention comprising a thin-film heating element 904, such as of Indium-Tin-Oxide (ITO), Carbon Nanowires, or other heating element attached to a polycarbonate, or other suitable material, on a lens 902. An inner protective layer of polyethylene terephthalate (PET) may be employed to cover the heating element to protect it from scratching. An upper bus bar 906 is attached (as by gluing), or preferably clamped or otherwise retained, to the peripheral upper length of the polycarbonate lens 902 and connected to a positive lead wire 912. A lower bus bar 908 is attached (by gluing), or preferably clamped or otherwise retained, to the peripheral lower length of the polycarbonate lens 902 and connected to a negative lead wire 914, such that portions of the upper bus bar 906 and lower bus bar 908 interconnect with the thin-film heating element 904. Both upper bus bar 906 and lower bus bar 908 contain teeth-like contacts 916 protruding from them in order to create distinct contact areas with the thin-film heating element 904. A retaining member 910, made from plastic, rubber, or another suitable material, surrounds the furthest most peripheral edge of the polycarbonate lens 902 securing the thin-film heating element 904, upper bus bar 906, lower bus bar 908, and at least part of positive lead wire 912 and negative lead wire 914. The retaining member 910 ensures interconnection of the partial contact surface area of the bus bars 906, 908 with the thin-film heating element 904. The retaining member 910 preferably comprises a block-U-shaped channel for clamping around, or otherwise engaging in force-fit relationship, all or part of the peripheral edges of the bus bars 908, 906 and the lens substrate 902 having the thin-film heating element 904 thereon, such that the bus bars are held in consistent contact with the heating element.

It will be appreciated by those skilled in the art, as shown in FIG. 9b, that an additional outer lens 903 may also be included in the basic structure of FIG. 9a, in any of the embodiments hereof, to provide additional insulation, and without departing from the true scope and spirit of the invention. Thus, referring to FIG. 9b, the additional outer lens 903 may be added to the A/R or V/R vision screen, or lens 900' which, similar to that of FIG. 9a, also comprises a thin-film heating element 904', such as of Indium-Tin-Oxide (ITO), Carbon Nanowires, or other heating element attached to a polycarbonate, or other suitable material, on a lens 902'. A/R or V/R vision screen or lens 900' may also further comprise an inner protective layer of polyethylene terephthalate (PET) employed to cover the heating element to protect it from scratching. Similar to the A/R or V/R vision screen or lens 900, lens 900' further comprises an upper bus bar 906' attached (as by gluing), or preferably clamped or otherwise retained, to the peripheral upper length of the polycarbonate lens 902' and connected to a positive lead wire 912'. A lower bus bar 908' is also attached (by gluing), or preferably clamped or otherwise retained, to the peripheral lower length of the polycarbonate lens 902' and connected to a negative lead wire 914', such that portions of the upper bus bar 906' and lower bus bar 908' interconnect with the thin-film heating element 904'. Both upper bus bar 906' and lower bus bar 908' contain teeth-like contacts 916' protruding from them in order to create distinct contact areas with the thin-film heating element 904'. A retaining member 910', made from plastic, rubber, or another suitable material, surrounds the furthest most peripheral edge of the polycarbonate lens 902' securing the thin-film heating element 904', upper bus bar 906', and lower bus bar 908', and preferably at least a part of positive lead wire 912' and negative lead wire 914'. The retaining member 910' ensures interconnection of the partial contact surface area of the bus bars 906', 908' with the thin-film heating element 904'. The retaining member 910' preferably comprises a block-U-shaped channel for clamping around, or otherwise engaging in force-fit relationship, all or part of the peripheral edges of the bus bars 908', 906', the lens substrate 902' having the thin-film heating element 904' thereon, and the other lens 903, all such that the bus bars are held in consistent contact with the heating element. The terms vision screen, lens, and eye-shield are used essentially synonymously herein for purposes of the invention as disclosed and claimed herein.

In the embodiments of FIGS. 9a and 9b, upper bus bar 906, 906' and lower bus bar 908, 908' may be customized by adding, subtracting, and changing sizes of the teeth-like contacts 916, 916' protruding from them in order to create a greater contact area where more current is needed to heat the eye-shield 900, 900', or a reduced contact area where less current is needed to reduce heating of the eye-shield 900, 900'. These embodiments and designs are desirable because customizable heating will allow a user to dissipate fog on the polycarbonate lens 902, 902' while still conserving battery power. Additionally, these embodiments are more desirable than previously-described conceptual embodiments because with a single positive lead wire 912, 912' going to a single upper bus bar 906, 906' and a single negative lead wire 914, 914' going to a single lower bus bar 908, 908', it is less cumbersome, less costly and easier to manufacture, since the manual steps of painting larger silver ink bus bars overlapping onto a heating element and securing the lead wire directly to the silver ink bus bars with a rivet and contact are eliminated. This embodiment is adaptable and customizable to any shape and contour of any eye-shield/vision screen/lens.

Figure 10:
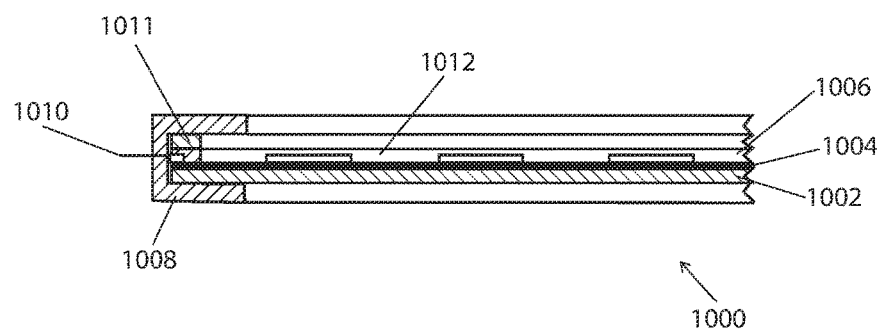
FIG. 10 is a cross-section view of part of an A/R or V/R substrate embodiment shown in FIG. 11 having a bus bar electrical interconnection system in accordance with an aspect of the invention for customized efficient and tuned heating to prevent hot spots and fogging of the substrate.

Referring to FIG. 10, there is shown a partial cross-section, taken along lines 10-10 of FIG. 11, of a flattened embodiment of a bus bar electrical interconnection system on an eye-shield, vision screen, or lens 1000, as may be used in a typical V/R or A/R system, in accordance with an aspect of the invention, comprising a thin-film heating element 1004 attached to a polycarbonate, or other suitable material, lens 1002. A bus bar 1006 is attached along the peripheral length of the polycarbonate lens 1002, and the bus bar contains teeth-like contacts 1012 protruding from them such that portions of the bus bar 1006 interconnect with the thin-film heating element 1004. A retaining member 1008, similar to that shown and described below in connection with FIG. 28b, made from any suitable rigid material, whether non-conductive or conductive, surrounds the peripheral edge of the polycarbonate lens 1002, thin-film heating element 1004, and bus bar 1006, securing these items firmly together in a preferably substantially block-U-shaped, or U-shaped, configuration as shown. The retaining member 1008 may have protruding portions corresponding with only those portions of the bus bar 1006 to make contact (i.e., laterally raised inverted hills, or teeth 1012) with the heating element 1004 in such a way that only the portions of the bus bar that are raised make contact, whereas the portions of the bus bar that do not make contact (i.e., laterally retracted inverted valleys between the teeth 1012) are allowed to remain spaced apart from the heating element since the bus bar does not have a protruding portion in those areas. Further, the non-contact areas may be spaced apart from the heating element with a non-conductive spacer as shown at 1011. A lead wire 1010 is connected to the bus bar 1006 to supply power to the bus bar 1006 and thin-film heating element 1004 in order to heat the polycarbonate lens 1002 to dissipate any fog or precipitation on the polycarbonate lens.

In this embodiment, the bus bar 1006 may be customized by adding, subtracting, and changing sizes of the teeth-like contacts 1012 protruding from them in order to create a greater contact area where more current is needed to heat the eye-shield 1000, and to reduce contact area where less current is needed to reduce heating of the eye-shield 1000. This embodiment and design is desirable because it allows for customizable heating without being bulky or cumbersome and because it allows a user to dissipate fog on the polycarbonate lens 1002 while still conserving battery power. This embodiment is adaptable and customizable to any shape and contour of any eye-shield, vision screen or lens of an A/R or V/R system.

Referring to FIG. 11, there is shown a graphical representation of a front view of a bus bar electrical interconnection system on an irregular-shaped eye-shield (vision screen or lens) 1100 adapted for use in an electronic headset of a V/R or A/R system in accordance with an aspect of the invention. The eye-shield 1100 comprises a polycarbonate lens 1102 adapted for display of information 1101 on the lens and having a thin-film heating element 1104 deposited thereon, and the bus bar electrical interconnection system comprises upper bus bar 1106 and lower bus bar 1110, each bus bar having a contacting side and a non-contacting side, each bus bar being crimped, bent, folded, built up, or otherwise manufactured in an altered structure or configuration to form protrusions and recessions such that each bus bar makes only partial contact with the thin-film heating element 1104. Thus there are provided a plurality of contact areas 1108, comprising teeth-like contacts on the upper bus bar 1106 and also areas of contact 1112 on the lower bus bar 1110, each of the contact areas 1108, 1112 forming, in this embodiment of this aspect of the invention, that part of the bus bars' contacting side which makes contact with the heating element 1104.

The amount of power, and the location or pattern of application of the power, to the thin-film heating element 1104, is dependent upon where and what parts of the bus bars 1106, 1110 are retained against the thin-film heating element by a retaining member 1113 (shown with dotted lines in FIG. 11 to allow visibility of the bus bar configurations, and similar to that shown and described in connection with FIG. 28b). A battery power source 1114 with a positive terminal 1116 and negative terminal 1118 connects at the positive terminal to the upper bus bar 1106 through a positive circuit wire 1120, and connects at the negative terminal to the lower bus bar 1110 through a negative circuit wire 1122. The bus bars 1106, 1110 are secured on a peripheral edge of the polycarbonate lens 1102 by gluing, or a retaining member 1113 which is made from a suitable material to attach the bus bars in partial contacting relationship as described with the heating element 1104. The retaining member may engage the entire periphery of the polycarbonate lens 1102 but so as to enforce contact of only those portions of the bus bar 1106, 1110 designed to make contact with the thin-film heating element 1104.

An irregular shape of eye-shield 1100 is necessary to fit the unique curvature and shape of a user's face. However, because of the irregular shape of the eye-shield, a uniform flow of current across the eye-shield 1100 has been difficult to achieve. In prior concepts of a heated eye-shield, there has been a hot spot above the nose cut-out portion of eye-shields. In the embodiment of the invention shown in FIG. 11, the upper bus bar 1106, and the lower bus bar 1110, are each an individual and a continuous piece of material, and may be customized by adding, subtracting, and changing sizes of the teeth-like contacts protruding from them in order to create greater areas of contact 1108, 1112 on the upper peripheral inner surface, or lower peripheral inner surface, where more current is needed to heat the eye-shield. Conversely, where less current is needed to reduce heating of a particular area of the eye-shield 1100, lesser contact areas 1108, 1112 may be readily created. This capability of this aspect of the invention to enable greater or lesser contact areas 1108, 1112 by the bus bars 1106, 1110 is what gives manufacturers the ability to customize and tune their bus bars to their particular eye-shields' shapes and sizes, available battery power, and other requirements.

This embodiment of a heated eye-shield 1100 is desirable because customizable heating will allow a user to dissipate fog on the polycarbonate lens 1102 while still conserving reserves in the battery 1114. Additionally, this embodiment is more desirable than previous embodiments with multiple bus bars and lead wires on a top periphery and bottom periphery of a lens because, with a single positive lead wire 1120 going to a single upper bus bar 1106, and a single negative lead wire going to a single lower bus bar 1110, the system is less cumbersome, cheaper, and easier to manufacture than would otherwise be the case involving using a rivet to connect the wires to a silver ink painted bus bar on the heating element 1104. This embodiment is also adaptable and customizable to any shape and contour of any eye-shield, whether large, small, or irregular in shape. In particular, since as shown, there is no contact between the lower bus bar 1110 with the thin-film heating element 1104 at a location 1103 just above a nose-bridge cutout portion 1105 of the eye-shield 1100, so that overheating and hot spots are avoided at that location and extending into the center of the eye-shield.

Figure 12:
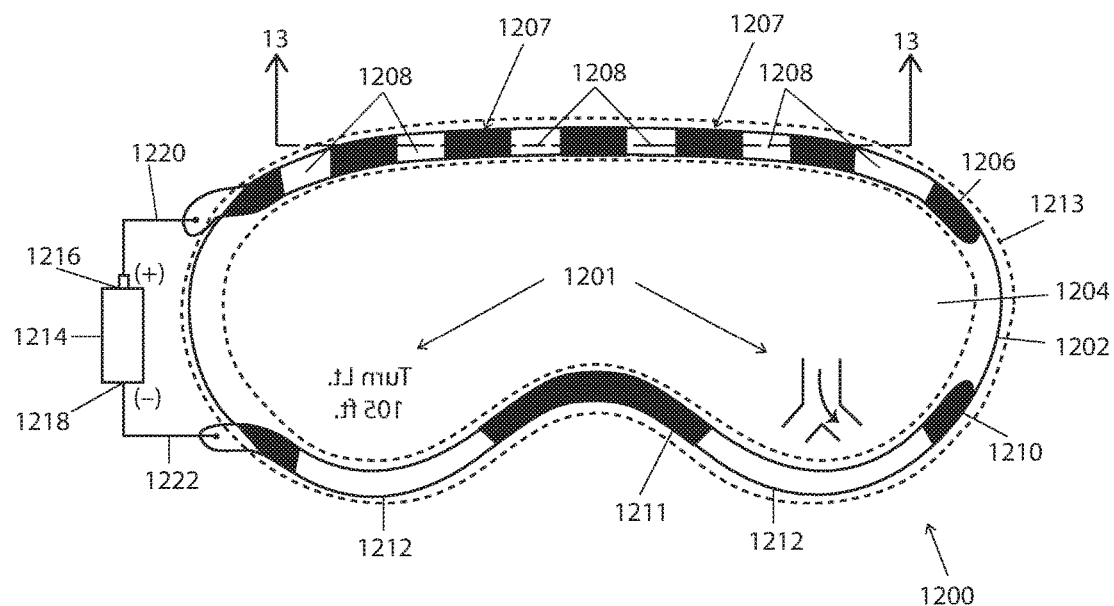
FIG. 12 is a graphic representation of a front view of an alternate bus bar electrical interconnection system in accordance with an aspect of the invention for customized efficient and tuned heating to prevent fogging and avoid hot spots on an A/R or V/R substrate, wherein the interconnection between the battery and the bus bars does not require riveting of the bus bar to the substrate.

Referring to FIG. 12, there is shown a graphical representation of a front view of a bus bar electrical interconnection system on an irregularly-shaped eye-shield (vision screen or lens) 1200 adapted for use in an electronic headset of a V/R or A/R system in accordance with an aspect of the invention. The eye-shield, vision screen or lens 1200 comprises a polycarbonate lens 1202 adapted for display of information 1201 on the lens and having a thin-film heating element 1204 attached thereto, and the bus bar electrical interconnection system comprises upper bus bar 1206 and lower bus bar 1210, each bus bar having a contacting side and non-contacting side, each bus bar being crimped, bent, folded, built up with adhered additional material, or otherwise manufactured in an altered structure or configuration such that each bus bar makes partial contact with the thin-film heating element 1204 at the protruding protrusion portions 1208, 1212 (or alternatively stated between recession portions 1207, 1211, respectively) of the bus bar. Thus, the contacting side of the bus bar 1206 has a plurality teeth-like protrusion contacts that create points or areas of contact 1208 with the thin-film heating element 1204, and the lower bus bar 1210 is crimped, bent, folded, or otherwise manufactured such that the contacting side of the bus bar 1210 has a plurality of teeth-like protrusion contacts 1212 that create one or more points, or areas of contact, 1211 with the thin-film heating element. As shown in FIG. 12, there are recession areas 1207, 1211 between each protrusion contact area 1208, 1212, respectively. Lower bus bar 1210 comprises a protruding configuration alteration, or protrusion, 1212 (or alternatively recession configuration alteration, or recession 1211) so as to be adapted for preventing contact of the lower bus bar with the thin-film heating element 1204 above a nose cut-out portion on the eye-shield 1200. The polycarbonate lens 1202, thin-film heating element 1204, upper bus bar 1206, and lower bus bar 1210 are secured together by glue, or preferably a retaining member 1213 made from a suitable material and as further described in connection with FIG. 28b.

A battery power source 1214 is provided with a positive terminal 1216 and negative terminal 1218. The positive terminal 1216 connects to, or is adapted to connect to, the upper bus bar 1206 through a positive circuit wire 1220, and the negative terminal 1218 connects to, or is adapted to connect to, the lower bus bar 1210 through a negative circuit wire 1222. The contacts between the circuit wires 1220, 1222 and the bus bars 1206, 1210, respectively, are shown achieved at a location apart from the eye-shield lens substrate 1202. Thus, the attachment of the circuit wires 1220, 1222 and the bus bars 1206, 1210, respectively is accomplished preferably with a rivet, but wherein the rivet does not pass through the eye-shield 1202 itself.

As previously described with eye-shield 1100, an irregular shape of eye-shield 1200 is necessary to fit the unique curvature and shape of a user's face. However, because of the irregular shape of the eye-shield 1200, a uniform flow of current across the eye-shield 1200 is difficult to achieve. In prior concepts of a heated eye-shield (not part of an A/R or V/R system), there has been a hot spot above the nose cut-out portions of eye-shields. In this embodiment, however, upper bus bar 1206 and lower bus bar 1210 are each an individual and continuous piece, and may be customized by adding, subtracting, and changing sizes of the teeth-like contacts protruding from them in order to create greater areas of contact 1208, 1212 on the upper peripheral surface or lower peripheral surface. Thus, as previously described, where more current is needed to heat the eye-shield 1200 greater contact area 1208, 1212 may be provided by design, and where less current is needed, lesser contact area 1208, 1212 may be provided by design, all without substantially impacting the time needed to manufacture each eye-shield.

This embodiment and design is desirable because customizable heating will allow a user to dissipate fog on the polycarbonate lens 1202 while still conserving reserves in the battery 1214. Additionally, this embodiment is more desirable than previous embodiments with multiple bus bars and lead wires on a top periphery and bottom periphery of a lens, because with a single positive lead wire 1220 going to a single upper bus bar 1206 and a single negative lead wire 1222 going to a single lower bus bar 1210, it is less cumbersome to users, cheaper, and easier to manufacture. This embodiment is adaptable and customizable to any shape and contour of any eye-shield. Additionally, it is easier to manufacture and maintain the eye-shield 1200 with the lead wires 1220, 1222 attaching to the bus bars 1206, 1210 apart from the eye-shield 1200 because they are attachable anywhere around the eye-shield 1200 instead of directly on the eye-shield 1200.

Figure 13:
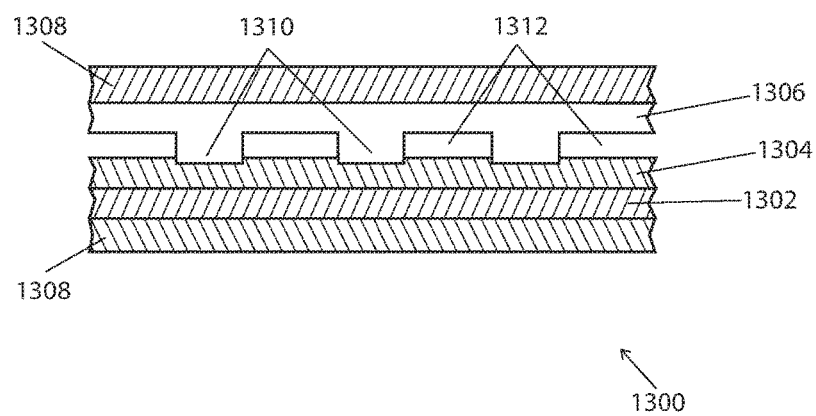
FIG. 13 is another graphic representation of a section view of part of an alternative embodiment of an A/R or V/R substrate bus bar electrical interconnection system in accordance with an aspect of the invention to make the substrate adapted for customized efficient and tuned heating to prevent hot spots while preventing fogging of the substrate.

Referring to FIG. 13, there is shown a graphical illustration of a section of an alternative embodiment of a bus bar electrical interconnection system on an eye-shield (vision screen or lens) 1300 adapted for use in an electronic headset of a V/R or A/R system in accordance with an aspect of the invention, comprising a thin-film heating element 1304 attached to a polycarbonate, or other suitable material, lens 1302 adapted for displaying information (not shown) to a user, a bus bar 1306 secured on a peripheral edge of the polycarbonate lens 1302 by a retaining member 1308, ensuring interconnection of portions of the bus bar with thin-film heating element 1304. Alternatively, gluing, adhesives, or another method may be used to attach the bus bar 1306 to the polycarbonate lens 1302, creating contact between the bus bar 1306 and thin-film heating element 1304. Bus bar 1306 comprises teeth-like contacts 1310 adapted for contacting the thin-film heating element 1304 at spaced intervals 1312. Alternatively, the regions 1312 between teeth-like contacts 1310 may be considered recessions 1312. The teeth-like contacts 1310 may be made on the bus bar 1306 by bending, crimping, or building up to form at least one, or a plurality of, receding and protruding configurations. Alternatively, the teeth-like contacts 1310 may be made on the bus bar 1306 by adhering protruding, electrically conductive, pieces to a bus bar through use of a conductive adhesive. The teeth-like contacts 1310 may be longer or shorter in order to customize heating of the eye-shield 1300 to prevent fogging and to conserve power. Likewise, the spaced intervals 1312 located between the teeth-like contacts 1310 may be wider or narrower in order to additionally customize heating of the eye-shield 1300 to prevent fogging and conserve power. The spaced intervals 1312 may also be insulated with an insulating material in order to prevent incidental contact between the bus bar 1306 and thin-film heating element 1304 where a contact area is not desired.

Customizable teeth-like contacts 1310 and spaced intervals 1312 are desirable in an application with a thin-film heating element 1304 in order to create a heated eye-shield without hot spots or at least where hot spots are minimized. Through customization of a bus bar, contact areas between the bus bar and a thin-film heating element can be made greater or smaller, allowing more or less current to flow through particular areas of the thin-film heating element that heats a lens. When more current flows through an area of a thin-film heating element, more heat is generated in that area. The ability to apply differing amounts of current to different portions of a heated lens through the contact area between the bus bar and thin-film heating element will allow more uniform heating of lenses, even if a lens is of a particular irregular shape.

Figure 14:
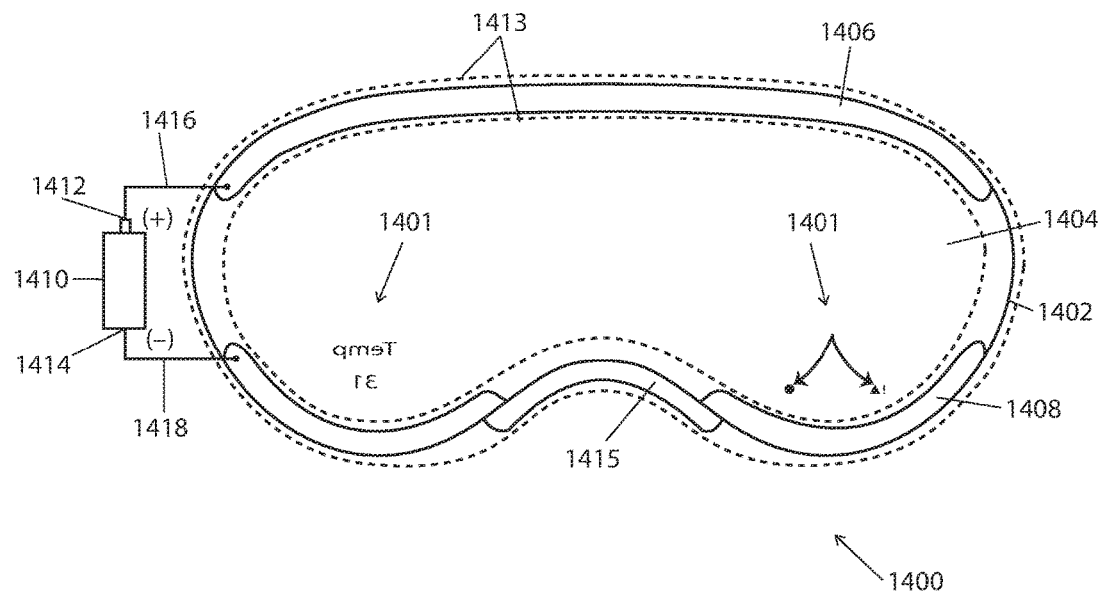
FIG. 14 is a graphic representation of a front view of an alternate bus bar electrical interconnection system in accordance with an aspect of the invention for avoiding a hot spot over the nose-bridge cutout portion of an A/R or V/R substrate, wherein the lower bus bar is bent, crimped, serpentined, or otherwise physically altered so as to have only the non-diverted portions thereof retained in connection with a heating element on the substrate.

Referring to FIG. 14, there is shown a graphical schematic representation of a front view of an embodiment of an electrical interconnection system on an irregular-shaped eye-shield (vision screen or lens) 1400 adapted for use in an electronic headset of a V/R or A/R system in accordance with an aspect of the invention comprising a thin-film heating element 1404 attached to a polycarbonate lens 1402 (the lens being adapted for displaying information 1401 thereon to a user), an upper bus bar 1406 attached to the peripheral upper length of the polycarbonate lens, and a lower bus bar 1408 attached to the peripheral lower length of the polycarbonate lens. A battery power source 1410 with a positive terminal 1412 and negative terminal 1414 connects to the upper bus bar 1406 and lower bus bar 1408, respectively. For interconnection of the upper bus bar 1406 with the battery 1410, a positive circuit wire 1416 is provided, and for interconnection of the lower bus bar 1410 with the battery, a negative circuit wire 1418 is provided. These interconnections between the battery terminals 1412, 1414 and the bus bars 1406, 1410 are made using rivets, glue, clamps, or other method of connection. Lower bus bar 1408 is crimped, bent, or folded such that there is no contact between the lower bus bar 1408 and thin-film heating element 1404 on the portion of the polycarbonate lens 1402 on the cut-out portion of the eye-shield 1400 adapted for resting above the user's nose. A retaining member 1413 clamps, or otherwise holds, appropriate portions of the bus bars 1406, 1408 in contact with the heating element 1404, while ensuring that other portions, such as that shown at 1415, are prevented from coming in contact with the heating element.

Upper bus bar 1406 and lower bus bar 1408 are each an individual and continuous piece of material. In contrast to previous designs, this embodiment helps to prevent hot spots over a nose cut-out portion on the polycarbonate lens 1402 by reducing contact area of the lower bus bar 1408 at the nose-bridge location. This is achieved by crimping, bending, folding, snaking, or otherwise manufacturing the lower bus bar 1402 such that it does not contact the thin-film heating element 1404 over the nose cut-out portion (i.e., as shown at 1415) of the eye-shield.

Figure 15:
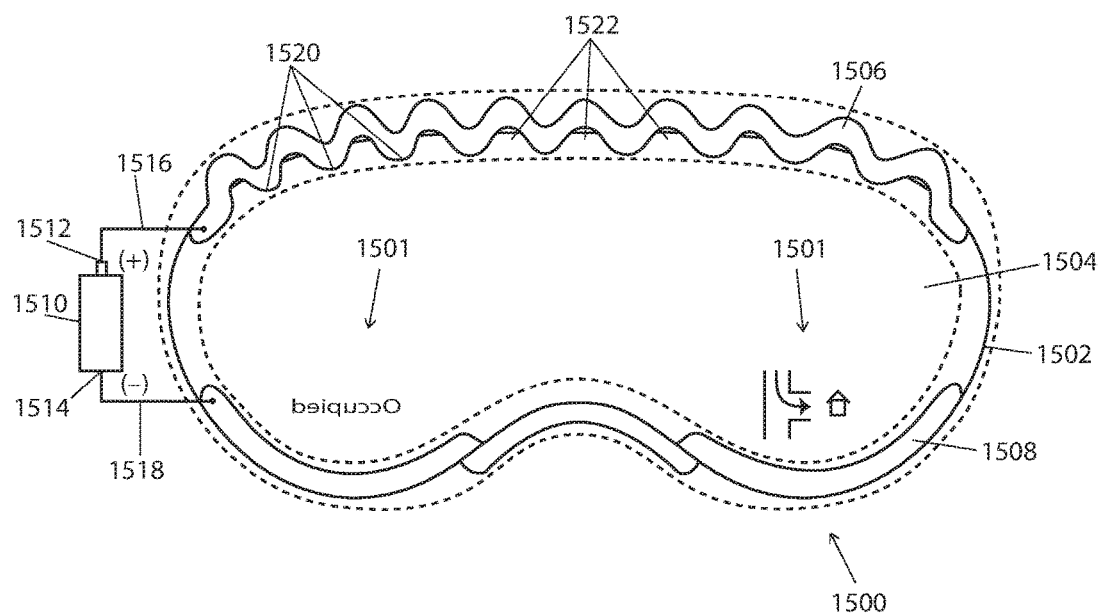
FIG. 15 is a graphic schematic representation of a front view of another alternate bus bar electrical interconnection system in accordance with an aspect of the invention for avoiding a hot spot over the nose-bridge cutout portion of an A/R or V/R substrate, further comprising an upper bus bar having encroaching elements, or teeth-like projections, held partially in contact with a heating element on the substrate for tuning the amount and location of current to be applied to the substrate.

Referring to FIG. 15, there is shown a graphical schematic representation of a front view of an embodiment of an electrical interconnection system on an irregularly-shaped eye-shield, vision screen or lens 1500 adapted for use with an A/R or V/R system and in accordance with an aspect of the invention. Lens 1500 comprises a thin-film heating element 1504 attached to a polycarbonate lens 1502 adapted for 1501. An upper bus bar 1506 is held in partial contact with the peripheral upper length of the polycarbonate lens 1502, and a lower bus bar 1508 is held in partial contact with a portion of the peripheral lower length of the polycarbonate lens 1502. A battery power source 1510 with a positive terminal 1512 and negative terminal 1514 connects to the upper bus bar 1506 and lower bus bar 1508, respectively. The positive terminal 1512 is connected to the upper bus bar 1506 through a positive circuit wire 1516, and the negative terminal 1514 is connected to the lower bus bar 1508 through a negative circuit wire 1518. These contacts are made using rivets, glue, clamps, or other method of connection.

Upper bus bar 1506 is crimped, bent, folded, snaked, or otherwise provided with an altered structure or configuration such that there are encroaching elements, or teeth-like contacts 1520, adapted for contacting the thin-film heating element 1504 at spaced intervals 1522. The teeth-like contacts 1520 are longer or shorter to create more or less contact area in order to customize heating of the eye-shield 1500 to prevent fogging and conserve power. Likewise, the spaced intervals 1522 located between the teeth-like contacts 1520 are wider or narrower in order to additionally customize heating of the eye-shield 1500 to prevent fogging and conserve power. Lower bus bar 1508 is preferably crimped, bent, or folded such that there is no contact between the lower bus bar 1508 and thin-film heating element 1504 on the portion of the polycarbonate lens 1502 on the cut-out portion of the eye-shield 1500 adapted for resting above the user's nose. A retaining member, or other means of securing such as glue or clamps, holds appropriate portions of the bus bars 1506, 1508 in contact with the heating element 1504, while ensuring that other portions are prevented from coming in contact with the heating element.

The irregular shape of eye-shield 1500 makes a uniform flow of current in order to prevent hot spots difficult and this has led to unnecessarily wasted power. Thus, it is desirable, as taught by this embodiment, for the bus bars 1506, 1508 to have customizable peripheral contacts with the thin-film heating element 1504. This embodiment achieves this with a singular upper bus bar 1506 that is crimped, bent, folded, or otherwise made to snake, creating encroaching or protruding elements that make contact with the thin-film heating element 1504 to provide a tuned, or tunable, amount of current and heat to the eye-shield 1500. Lower bus bar 1508 is also customizable and is crimped, bent, folded or otherwise manufactured such that it does not contact the thin-film heating element 1504 over the nose cut-out on the polycarbonate lens 1502. By avoiding hot spots above a nose cut-out through customized bus bars 1506, 1508, battery power will be conserved, and the eye-shield 1500 will be more comfortable to wear.

Figure 16:
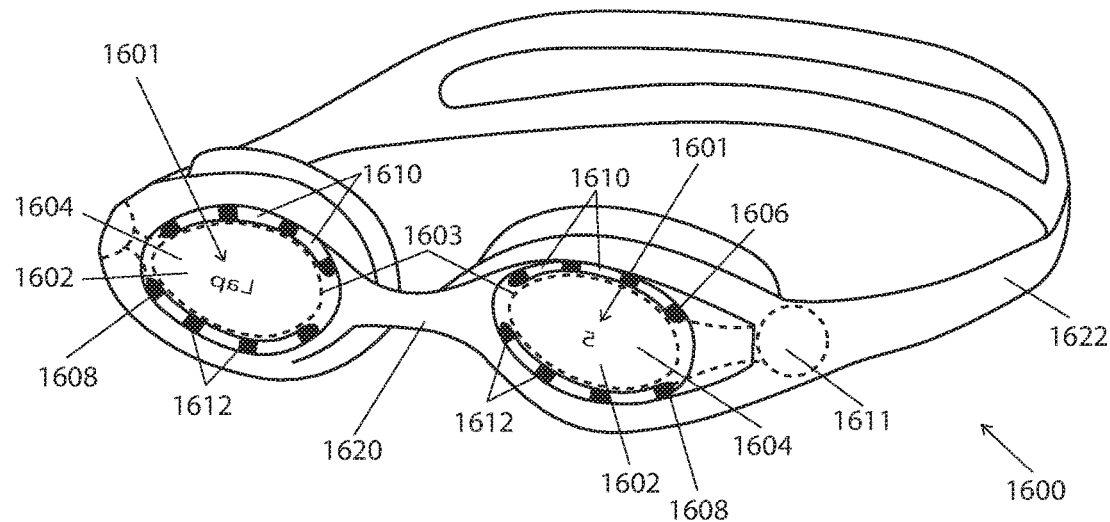
FIG. 16 is a graphic representation of a perspective view of an A/R adapted swimming goggle split-lens system having an alternate embodiment bus bar electrical interconnection system allowing tuning of the amount and location of current to be delivered while preventing hot spots and fogging of the split-lens system.

Referring to FIG. 16, there is shown a graphical schematic representation of a front view of an embodiment of an electrical interconnection system on a swimming goggle split lens eye-shield, vision screen or lens 1600 adapted for us in with an A/R or V/R system and in accordance with an aspect of the invention. The eye-shield 1600 comprises sealed thin-film heating elements 1604 attached to an inner portion of each polycarbonate lens 1602, each polycarbonate lens being adapted for displaying graphic and other visual information 1601 thereon to a user. Upper bus bars 1606 are engaged to the peripheral upper lengths of each polycarbonate lens 1602, and lower bus bars 1608 are engaged to the peripheral lower lengths of each polycarbonate lens 1602. Upper bus bars 1606 and lower bus bars 1608 are crimped, bent, folded, otherwise structurally diverted such that there are encroaching "hill-and-valley" elements, or teeth-like contacts, 1610 adapted for contacting the thin-film heating element 1604 at spaced intervals 1612. The teeth-like contacts 1610 are longer or shorter to create more or less contact area in order to customize heating of the eye-shield 1600 to prevent fogging and conserve power. Likewise, the spaced intervals 1612 located between the contacts 1610 are wider or narrower in order to customize heating of the eye-shield 1600 to prevent fogging and conserve power. The upper and lower bus bars 1606, 1608 are held in contact with a peripheral retaining member 1603 similarly to that previously described.

A battery power source 1611 connects with each of the upper bus bars 1606 and lower bus bars 1608 with lead wires as previously described in connection with other embodiments. The battery power source 1611, each polycarbonate lens 1620, the bus bars 1606, 1608, lead wires, and the retaining member 1603 are enclosed or embedded in a swim goggle frame 1620, and a rubber, extendable, or adjustable strap 1622 connects to the frame in order for a user to secure the eye-shield 1600 safely to the user's head in order to cover and protect the user's eyes.

The embodiment of the invention in FIG. 16 shows a split-lens goggle 1600, exemplifying that the invention may be applied to one or more lenses 1602 of an eye-shield. Each lens 1602 is customizable such that a user's needs may be met to prevent fogging of one or more lenses of an eye-shield 1600. The lenses 1602 can be large or small, and can fit in a large or small frame 1620, because there are not extra wires needed to interconnect the power sources 1611, and also because no rivets are needed to interconnect contacts with silver-ink bus bars 1606, 1608. Each lens 1602 of the swim goggle eye-shield 1600, regardless of size and shape, is customizable to prevent fogging without causing hot spots on the lenses 1602. Customizable bus bars 1606, 1608 manufactured for each lens 1602 will help to dissipate fog while conserving battery power by not overheating portions of a lens while still dissipating fog across the entire surface of the lens. Conserving battery power will allow the user the maximum usage time and on a singular battery or charge.

Figure 17:
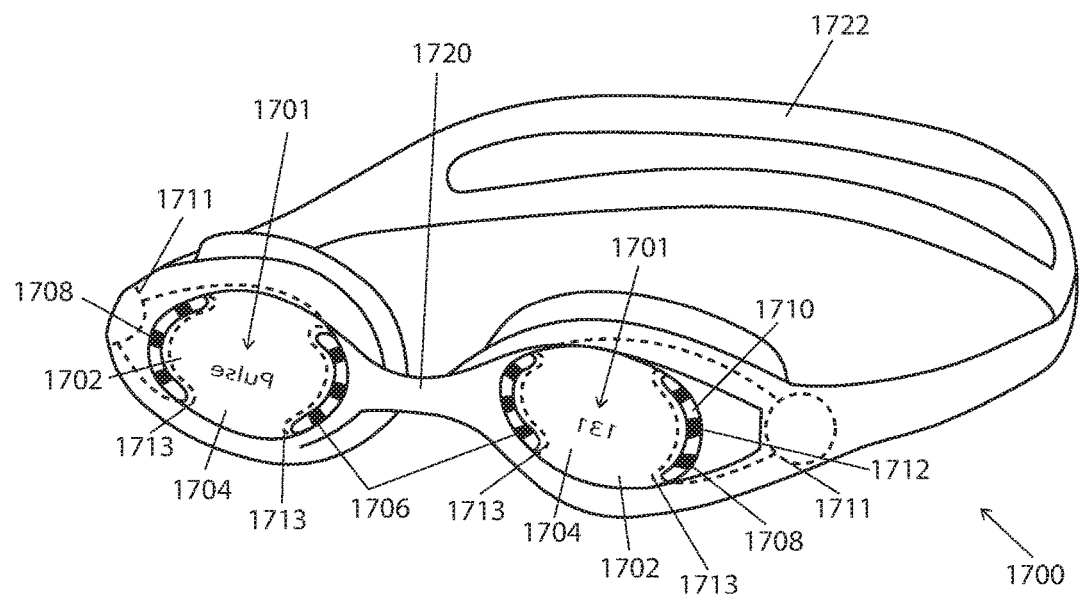
FIG. 17 is a graphic representation of a perspective view of an alternate A/R adapted swimming goggle split-lens system, having an alternate embodiment bus bar electrical interconnection system allowing tuning of the amount and location of current to be delivered while preventing hot spots and fogging of the split-lens system.

Referring to FIG. 17, there is shown a graphical schematic representation of a front view of an embodiment of an electrical interconnection system on an alternate swimming goggle split lens eye-shield 1700 adapted for use with an A/R or V/R system and in accordance with an aspect of the invention. The eye-shield 1700 comprises thin-film heating elements 1704 attached to each polycarbonate lens 1702 (each polycarbonate lens being adapted for displaying information 1701 thereon to a user), and the electrical interconnection system comprises inner bus bars 1706 held in contact with the peripheral inner portions of each polycarbonate lens 1702, and outer bus bars 1708 held in contact with the peripheral outer portions of each polycarbonate lens 1702 by multiple, split, retaining members 1713. Inner bus bars 1706 and outer bus bars 1708 are crimped, bent, folded, built up or otherwise physically altered in structure, or configuration, such that there are encroaching elements, or teeth-like contacts 1710 adapted for contacting the thin-film heating element 1704 (or alternatively painted contact pads—not shown—on the thin-film heating element) at spaced intervals 1712. The teeth-like contacts 1710 are longer or shorter, or higher or lower in the case of "hills and valleys" teeth-like contacts, to create more or less contact area in order to customize heating of the eye-shield 1700 to prevent fogging and conserve power. Likewise, the spaced intervals 1712 located between the teeth-like contacts 1710 are wider or narrower in order to additionally customize heating of the eye-shield 1700 to prevent fogging and conserve power. A battery power source 1711 interconnects with each of the inner bus bars 1706 and outer bus bars 1708 with positive and negative lead wires similarly to that described previously in connection with other embodiments. The battery power source 1711, each polycarbonate lens 1702, the lead wires, the bus bars 1706, 1708, and the retaining members 1713 are enclosed or embedded in a swim goggle frame 1720, and a rubber, extendable, or adjustable strap 1722 connects to the frame in order for a user to secure the eye-lens 1700 safely to the user's head in order to cover and protect the user's eyes.

Similar to the embodiment of the invention in FIG. 16, the embodiment of the invention in FIG. 17 may be applied to one or more lenses of an eye-shield to create a customized eye-shield to dissipate fog while conserving power usage. Additionally, the embodiment in FIG. 17 exemplifies that customizable bus bars can be situated horizontally or vertically, depending on the shape of an eye-shield and the needs of a user. Re-orienting the direction of the bus bars will generally not affect the utility and effectiveness of dissipating fog of an eye-shield of a V/R or A/R system, unless such re-orientation causes greater shape or size irregularities in the eye-shield which are more difficult to overcome. Reorienting the bus bars will not create a more cumbersome or bulkier eye-shield because there are still only two circuit wires, one for each bus bar. Having a customized heated eye-shield will help conserve power in a battery or power source and extend the usability of the eye-shield for defogging.

Figure 18:
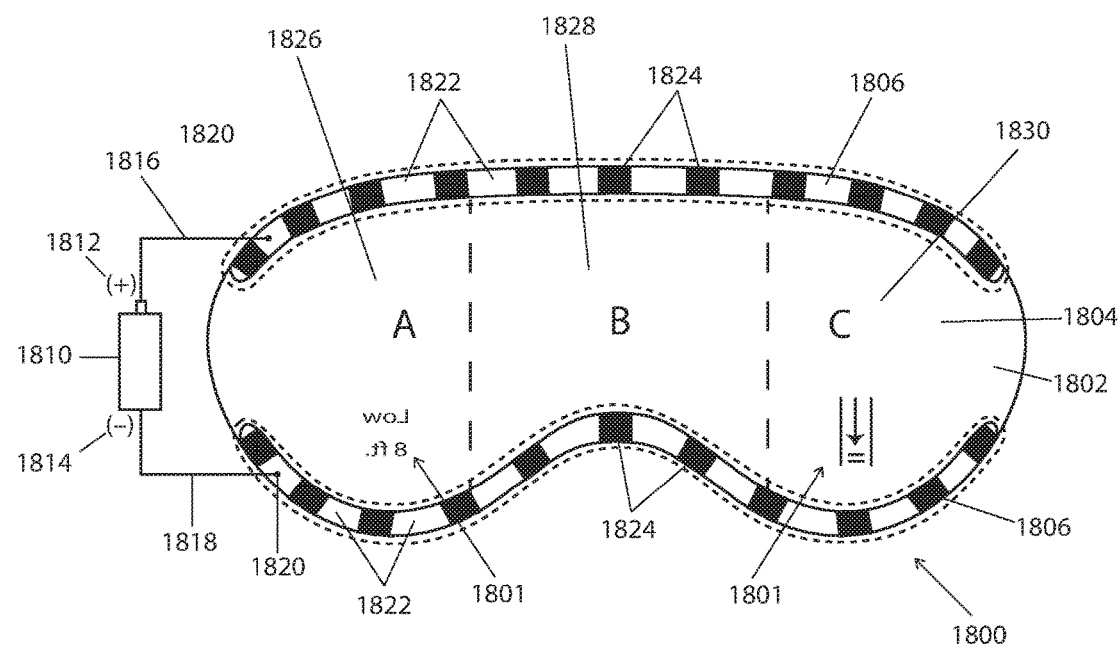
FIG. 18 is a graphic representation of a front view of an alternate bus bar electrical interconnection system in accordance with an aspect of the invention for allowing tuning the amount and location of current to be applied to an A/R adaptive protective eye-shield while avoiding hot spots and fogging of the eye-shield.

Referring to FIG. 18, there is shown a graphical schematic representation of a front view of an embodiment of an electrical interconnection system on an irregular shaped eye-shield 1800 adapted for use with an A/R or V/R system and in accordance with an aspect of the invention. The eye-shield 1800 comprises a thin-film heating element 1804 attached to a polycarbonate lens 1802 which is adapted for displaying information 1801 to a user, and the electrical interconnection system comprises an upper bus bar 1806 attached to the peripheral upper length of the polycarbonate lens 1802, and a lower bus bar 1808 attached to the peripheral lower length of the polycarbonate lens 1802. A battery power source 1810 with a positive terminal 1812 and negative terminal 1814 connects to the upper bus bar 1806 and lower bus bar 1808. Interconnection between the positive terminal 1812 of the battery 1810 and the upper bus bar 1806 is made through a positive circuit wire 1816, and interconnection between the negative terminal 1814 and the lower bus bar 1808 is made through a negative circuit wire 1818. These interconnections between the battery and the bus bars are made by soldering, rivets, glue, clamps, or other method of connection 1820.

The upper bus bar 1806 and lower bus bar 1808 are crimped, bent, folded, built up, or otherwise physically altered in structure or configuration such that there are protruding configurations, or teeth-like contacts 1822, adapted for contacting, or in another embodiment actually contacting, the thin-film heating element 1804 at spaced intervals 1824. The teeth-like contacts 1822 are longer or shorter to create more or less contact area in order to customize heating of the eye-shield 1800 to prevent fogging and conserve power. Likewise, the spaced intervals 1824 located between the teeth-like contacts 1822 are wider or narrower in order to additionally customize heating of the eye-shield 1800 to prevent fogging and conserve power. Lower bus bar 1508 is bent around a cut-out portion of the eye-shield 1800 adapted for resting above the user's nose, and the "hills and valleys" of the bus bars are oriented so as to conserve power and avoid hot spots as much as possible.

As previously discussed with other embodiments of the invention, because the irregular shape of eye-shield 1800 has made a uniform flow of current and application of power through thin-film heating element 1804 across polycarbonate lens 1802 difficult, which fact in turn has resulted in an unnecessary extra use of power, it is desirable, as in this embodiment, for the bus bars 1806, 1808 to have customizable peripheral partial contacts with the thin-film heating element 1804 (or alternatively painted contact pads—not shown—on the thin-film heating element). This embodiment is customizable to avoid hot spots and reduce power usage by having a singular upper bus bar 1506 and a singular lower bus bar 1808 that is crimped, bent, folded, built up or otherwise made with teeth-like contacts, "hills and valleys", or protrusions creating protruding elements with peaks and valleys that make contact with the thin-film heating element 1804 to provide current and, in turn, heat the eye-shield 1800.

The teeth-like contacts 1822 are separated by spaced intervals 1824 that are also customizable to be wider or narrower to further customize heating of the eye-shield 1800. With customizable heating in this embodiment, hot spots that normally occur, for example, over a nose cut-out in the eye-shield 1800, signified by region B 1828, can be avoided by making the teeth-like contacts and spaced intervals wider or narrower to supply less current to the region. Likewise, cool spots may otherwise occur in region A and region C 1826, 1830 and can be avoided by making the teeth-like contacts and spaced intervals wider or narrower to supply more current to these regions A and region C 1826, 1830. Additionally, by supplying only a necessary amount of current to regions A, B and C 1826, 1828, 1830, respectively, to dissipate fog and condensation and not create hot spots, battery power will be conserved, extending the usability of fog dissipating properties of the eye-shield 1800.

An eye-shield bus bar electrical interconnection system in accordance with the invention can be adapted for use with any shaped eye-shield or goggle for an A/R or V/R system and to prevent fogging while preventing hot spots and conserving battery power. FIG. 19 through FIG. 23 exemplify this concept of adaptability of the bus bar electrical interconnection system for a variety of A/R or V/R-type eye-shields.

Figure 19:
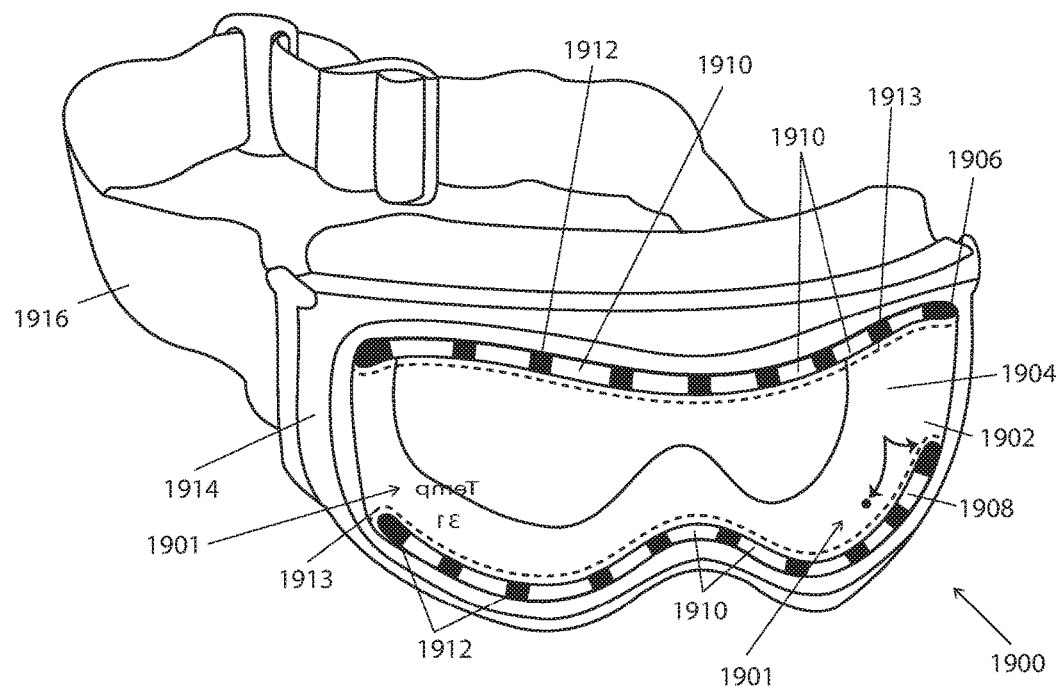
FIG. 19 is a graphic representation of an A/R adapted snow-goggle eye-shield bus bar electrical interconnection system in accordance with an aspect of the invention.

Referring to FIG. 19, there is shown a graphical schematic representation of a front view of an embodiment of an electrical interconnection system embodied in a snow goggle 1900 adapted for use in an A/R or V/R system and in accordance with an aspect of the invention comprising a thin-film heating element 1904 attached to an inner surface of a polycarbonate lens 1902 adapted for displaying information 1901 to a user. An upper bus bar 1906 is attached to the peripheral upper length of the polycarbonate lens 1902, and also a lower bus bar 1908 is attached to the peripheral lower length of the polycarbonate lens. Upper bus bar 1906 and lower bus bar 1908 are crimped, bent, folded, built up or otherwise altered in structure or configuration such that there are teeth-like contacts 1910 adapted for contacting the thin-film heating element 1904 (or alternatively painted contact pads—not shown—on the thin-film heating element) at spaced intervals 1912. The teeth-like contacts 1910 and spaced intervals 1912 are customizable to be longer or shorter, narrower or wider, to dissipate fog effectively on the polycarbonate lens 1902 without creating hot spots, and while conserving battery power. A retaining member 1913 secures the polycarbonate lens 1902, thin-film heating element 1904 and bus bars 1906, 1908 securely around the peripheral edge, ensuring interconnection of the bus bars to the thin-film heating element 1904. The electrical interconnection system, which also includes circuit wires and a battery not shown, are contained in or on a goggle frame 1914, made from plastic or another suitable material, and an adjustable strap 1916 made from elastic or another suitable material.

Figure 20:
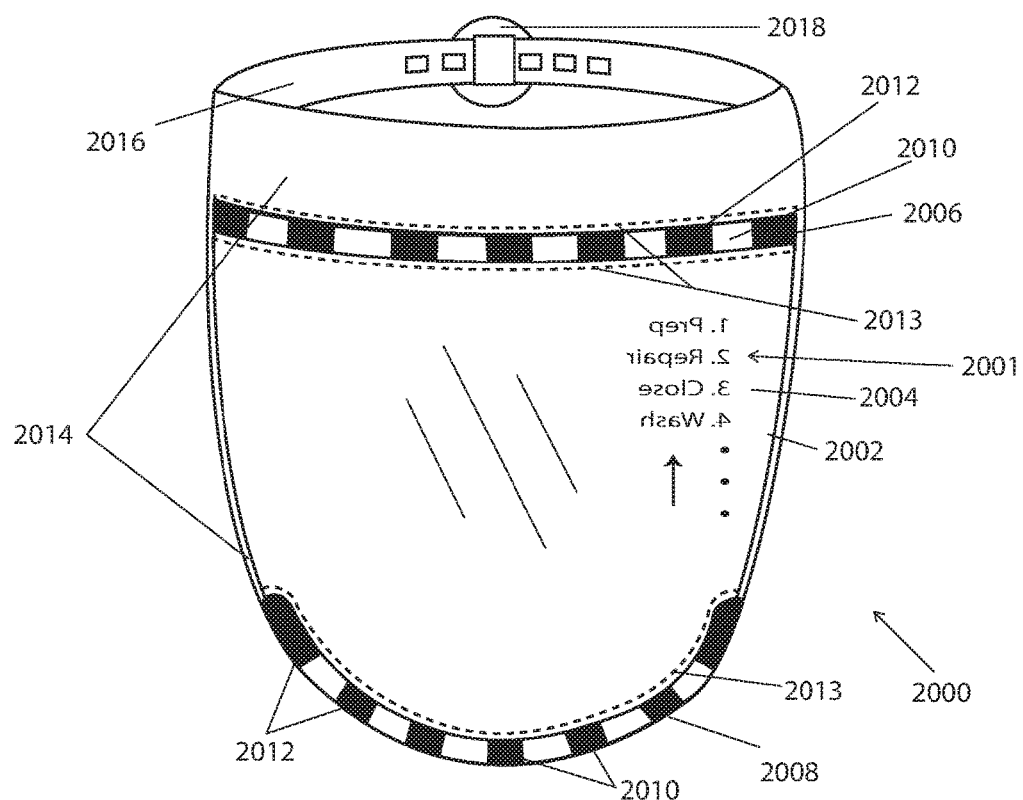
FIG. 20 is a graphic representation of an A/R adapted medical eye-shield bus bar electrical interconnection system in accordance with an aspect of the invention.

Referring to FIG. 20, there is shown a graphical schematic representation of a front view of an embodiment of an electrical interconnection system applied in a face shield, such as a medical face shield, 2000 that is adapted for use with an A/R or V/R system and in accordance with an aspect of the invention. The face shield 2000 comprises a thin-film or other substantially transparent heating element 2004 attached to an inner surface of a polycarbonate, or other suitable material, lens 2002 which is adapted for displaying information 2001 to a user. There is further provided an upper bus bar 2006 attached to the peripheral upper length of the polycarbonate lens 2002, and a lower bus bar 2008 attached to the peripheral lower length of the polycarbonate lens. Upper bus bar 2006 and lower bus bar 2008 are crimped, bent, folded, built up or otherwise altered in structure or configuration such that there are teeth-like contacts 2010 adapted for contacting the thin-film heating element 2004 (or alternatively painted contact pads—not shown—on the thin-film heating element), and spaced intervals 2012. The teeth-like contacts 2010 and spaced intervals 2012 are customizable to be longer or shorter, narrower or wider, to dissipate fog effectively on the polycarbonate lens 2002 without creating hot spots, and while conserving battery power. Retaining members 2013 secure the polycarbonate lens 2002, thin-film heating element 2004 and bus bars 2006, 2008 securely around the peripheral edge, ensuring interconnection of the bus bars 2006, 2008 to the thin-film heating element 2004. The electrical interconnection system, which also includes circuit wires and a battery not shown, which are contained in or on a medical face shield frame 2014 made from plastic or another suitable material, or on a head strap 2016 made from plastic or another suitable material, preferably with a knob 2018 for adjusting the head strap 2016. It will be appreciated by those skilled in the art that face shield 2000 may comprise different protective shield materials as known in the art and may be used in other industrial applications, such as for working with automobiles, welding, or other equipment.

Figure 21:
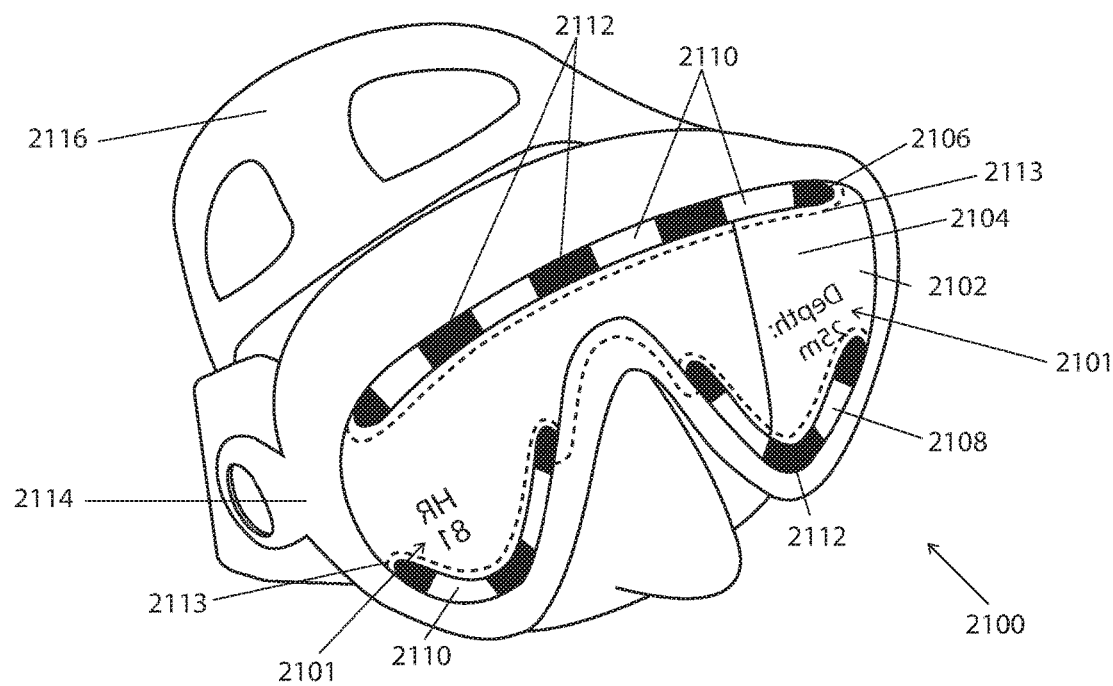
FIG. 21 is a graphic representation of an A/R adapted dive mask eye-shield bus bar electrical interconnection system in accordance with an aspect of the invention.

Referring to FIG. 21, there is shown a graphical schematic representation of a front view of an embodiment of an electrical interconnection system applied in a dive mask 2100 adapted for use with an A/R or V/R system and in accordance with an aspect of the invention. The dive mask 2100 comprises a thin-film heating element 2104 attached to an inner surface of a polycarbonate lens 2102 which is adapted for displaying information 2101 to a user. There is provided an upper bus bar 2106 attached to the peripheral upper length of the polycarbonate lens, and a lower bus bar 2108 attached to the lower peripheral length of the polycarbonate lens. Upper bus bar 2106 and lower bus bar 2108 are crimped, bent, folded, built up, or otherwise altered in structure or configuration, such that there are teeth-like contacts 2110 adapted for contacting the thin-film heating element 2104 (or alternatively painted contact pads—not shown—on the thin-film heating element), and spaced intervals 2112. The teeth-like contacts 2110 and spaced intervals 2112 are customizable to be longer or shorter, narrower or wider, to dissipate fog effectively on the polycarbonate lens 2102 without creating hot spots, and while conserving battery power. A retaining member 2113 secures the polycarbonate lens 2102, thin-film heating element 2104 and bus bars 2106, 2108 securely around the peripheral edge, ensuring interconnection of the bus bars to the thin-film heating element. The electrical interconnection system, which also includes circuit wires and a battery not shown, are contained in or on a dive mask frame 2114, made from plastic or another suitable material, or on an adjustable strap 2116 made from rubber or another suitable material.

Figure 22:
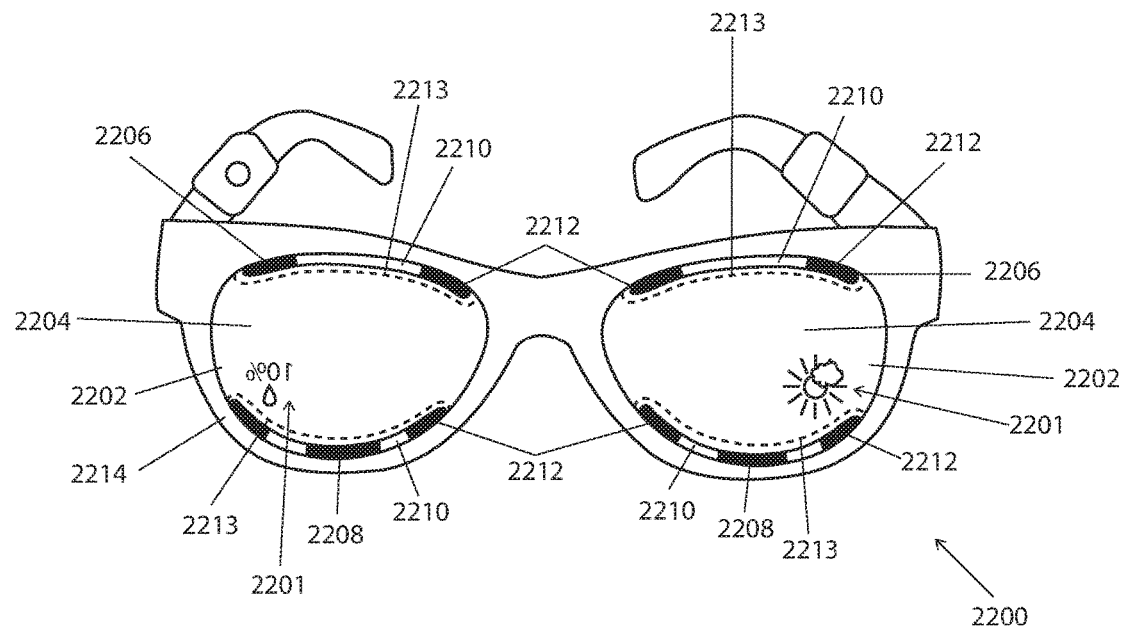
FIG. 22 is a graphic representation of an A/R adapted ballistics-rated, or other eye-glasses, eye-shield bus bar electrical interconnection system in accordance with an aspect of the invention.

Referring to FIG. 22, there is shown a graphical schematic representation of a front view of an embodiment of an electrical interconnection system implemented in eyeglasses 2200 adapted for use with an A/R or V/R system and in accordance with an aspect of the invention. The eyeglasses 2200 comprise two thin-film heating elements 2204 attached to an inner surface of two lenses 2202 adapted also for displaying information 2201 to a user. There are also provided two upper bus bars 2206 each attached to the peripheral upper length of each of the two lenses 2202, and two lower bus bars 2208 each attached to the peripheral lower length of each of the two lenses 2202. Upper bus bars 2206 and lower bus bars 2208 are crimped, bent, folded, built up, or are otherwise altered in structure or configuration such that there are teeth-like contacts 2210 adapted for contacting the thin-film heating elements 2204 (or alternatively painted contact pads—not shown—on the thin-film heating element), and spaced intervals 2212. The teeth-like contacts 2210 and spaced intervals 2212 are customizable to be longer or shorter, narrower or wider, to dissipate fog effectively on the lenses 2202 without creating hot spots, and while conserving battery power. A retaining member 2213 secures the polycarbonate lenses 2202, thin-film heating elements 2204 and bus bars 2206, 2208 securely around the peripheral edge, ensuring interconnection of the bus bars 2006, 2008 to the thin-film heating elements 2204. The electrical interconnection system, which also includes circuit wires and a battery not shown, are contained in or on an eyeglasses frame 2214 made from plastic or another suitable material.

Figure 23:
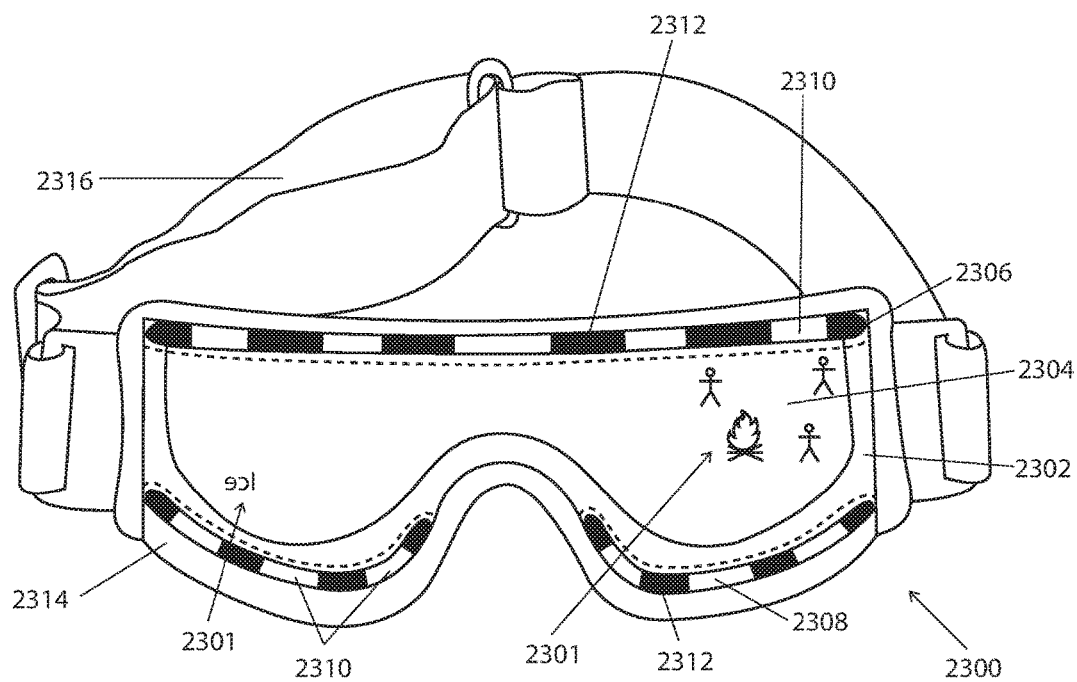
FIG. 23 is a graphic representation of an A/R adapted ballistics-rated goggle eye-shield bus bar electrical interconnection system in accordance with an aspect of the invention.

Referring to FIG. 23, there is shown a graphical schematic representation of a front view of an embodiment of an electrical interconnection system adapted for use in a ballistic eye-protection eye-shield 2300 adapted for use with an A/R or V/R system and in accordance with an aspect of the invention. The eye-shield 2300 comprises a thin-film heating element 2304 attached to an inner surface of a polycarbonate lens 2302 that is also adapted for displaying information 2301 to a user. There is further provided an upper bus bar 2306 attached to the peripheral upper length of the polycarbonate lens 2302, and lower bus bar 2308. Upper bus bar 2306 and lower bus bar 2308 are crimped, bent, folded, built up, or otherwise altered in structure or configuration, such as with protrusions applied with conductive adhesives, such that there are teeth-like contacts 2310 adapted for contacting the thin-film heating element 2304 (or alternatively painted contact pads—not shown—on the thin-film heating element), and spaced intervals 2312. The teeth-like contacts 2310 and spaced intervals 2312 are customizable to be longer or shorter, narrower or wider, to dissipate fog effectively on the polycarbonate lens 2302 without creating hot spots, and while conserving battery power. A retaining member secures the polycarbonate lens 2302, thin-film heating element 2304 and bus bars 2306, 2308 securely around the peripheral edge, ensuring interconnection of the bus bars 2306 2308 to the thin-film heating element 2304. The electrical interconnection system, which also includes circuit wires and a battery not shown, are contained in or on a ballistic eye-protection eye-shield frame 2314 made from plastic or another suitable ballistics material, or on an adjustable head strap 2316 made from rubber, elastic, or another suitable material.

Figure 29:
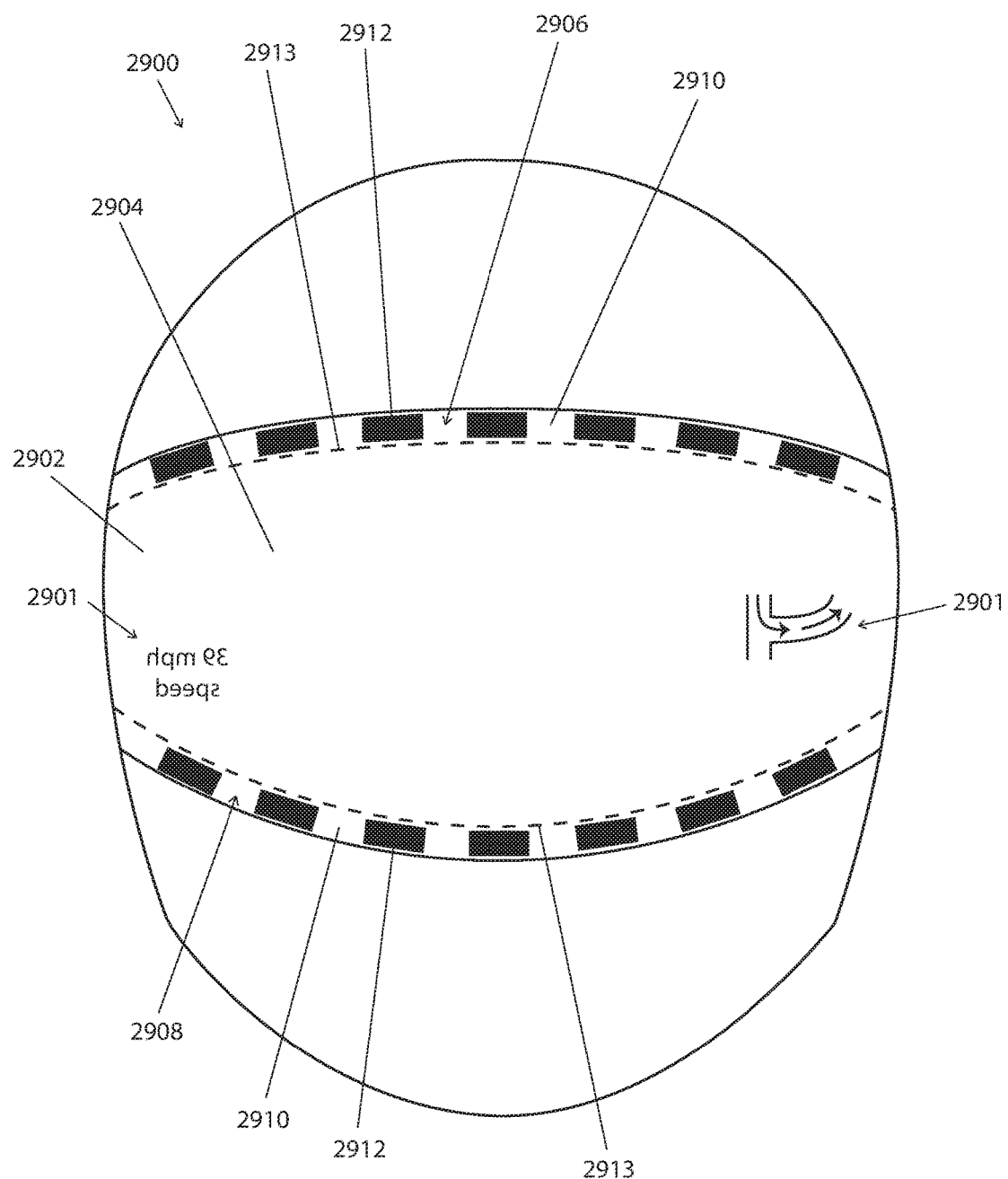
FIG. 29 is a graphic representation of a front view of an A/R adapted motorcycle, or snowmobile, helmet bus bar and electrical interconnection system in accordance with an embodiment and aspect of the invention.

Referring to FIG. 29, there is shown a graphical schematic representation of a front view of an embodiment of an electrical interconnection system applied in a motorcycle helmet 2900 face shield 2902 that is adapted for use with an A/R or V/R system and in accordance with an aspect of the invention. The face shield 2902 comprises a thin-film or other substantially transparent heating element 2904 attached to an inner surface of a polycarbonate, or other impact-resistant, suitable material, lens 2902 which is adapted for displaying information 2901 to a user. There is further provided an upper bus bar 2906 attached to the peripheral upper length of the lens 2902, and a lower bus bar 2908 attached to the peripheral lower length of the lens. Upper bus bar 2906 and lower bus bar 2908 are crimped, bent, folded, built up or otherwise altered in structure or configuration such that there are teeth-like contacts 2910 adapted for contacting the thin-film heating element 2904 (or alternatively painted contact pads—not shown—on the thin-film heating element), and spaced intervals 2912. The teeth-like contacts 2910 and spaced intervals 2912 are customizable to be longer or shorter, narrower or wider, to dissipate fog effectively on the lens 2902 without creating hot spots, and while conserving battery power. Retaining members 2913 secure the lens 2902, thin-film heating element 2904 and bus bars 2906, 2908 securely around the peripheral edge, ensuring interconnection of the bus bars 2906, 2908 to the thin-film heating element 2904. The electrical interconnection system, which also includes circuit wires and a battery not shown, which are contained in or on the helmet 2900 made from plastic or another suitable impact-resistant material.

Figure 24:
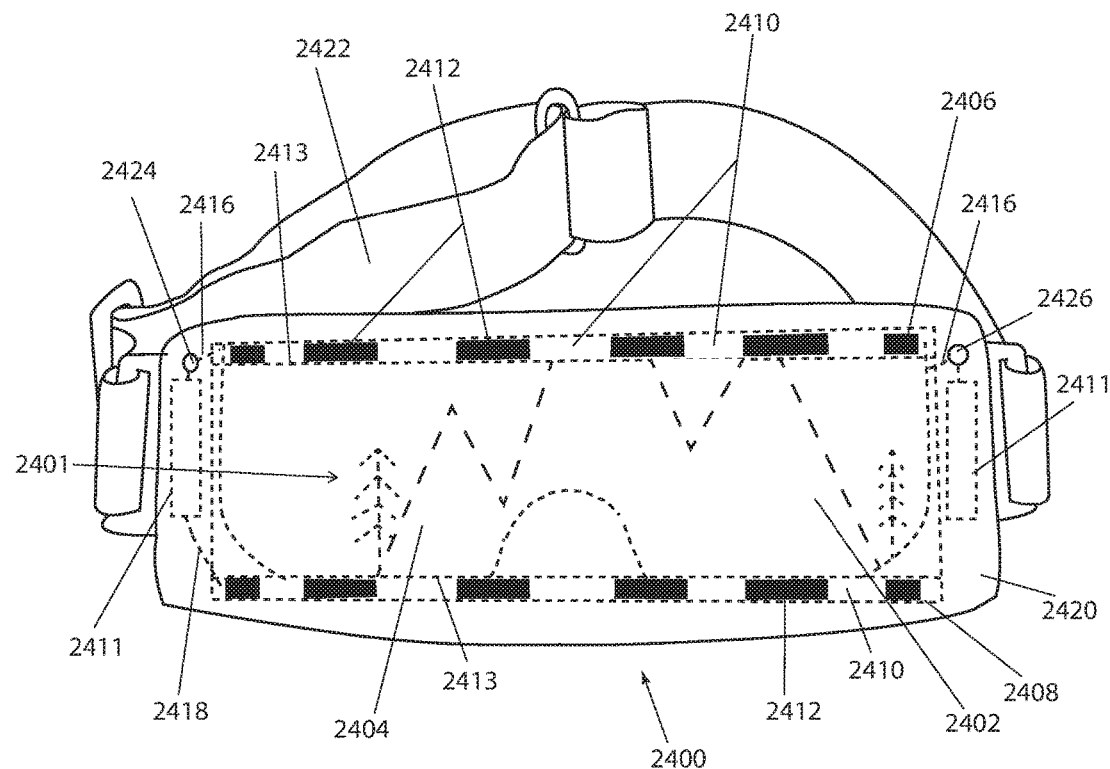
FIG. 24 is a graphical representation of a V/R or A/R system bus bar electrical interconnection system in accordance with an aspect of the invention.

Referring to FIG. 24, there is shown a graphical schematic representation of an embodiment of an electrical interconnection system adapted for use in a portable, goggle-type, virtual-reality (V/R), or alternatively augmented-reality (A/R), system 2400 in accordance with an aspect of the invention. The system 2400 comprises a thin-film or other substantially transparent heating element 2404 attached to an inner surface of a polycarbonate lens 2402 adapted for displaying graphic and other information 2401 to a user as part of the overall V/R or A/R immersive experience system including visual, audio and/or haptic stimulus as part of the system. In this embodiment of the invention, there is provided an upper bus bar 2406 attached to the peripheral upper length of the polycarbonate lens 2402, and a lower bus bar 2408 attached to the peripheral lower length of the polycarbonate lens. Upper bus bar 2406 and lower bus bar 2408 are crimped, bent, folded, built up, or otherwise altered in structure or configuration, such as with protrusions applied with conductive adhesives, such that there are partial contacts 2410 adapted for contacting the thin-film heating element 2404 (or alternatively painted contact pads—not shown—on the thin-film heating element) and spaced intervals 2412. The partial contacts 2410 and spaced intervals 2412 are customizable to be longer or shorter, narrower or wider, to dissipate fog effectively on the polycarbonate lens 2402 without creating hot spots, and while conserving battery power. A retaining member 2413 secures the polycarbonate lens 2402, thin-film heating element 2404 and bus bars 2406, 2408 to the thin-film heating element 2404. The electrical interconnection system, which also includes circuit wires 2416, 2418 and batteries 2411, are contained in or on a virtual reality frame 2420, made of plastic or another suitable material, or on an adjustable strap 2422. On/off, and other control, buttons 2424, 2426 are provided on the frame for purposes of controlling the electrical interconnection and optionally aspects of the V/R system as well.

Figure 25:
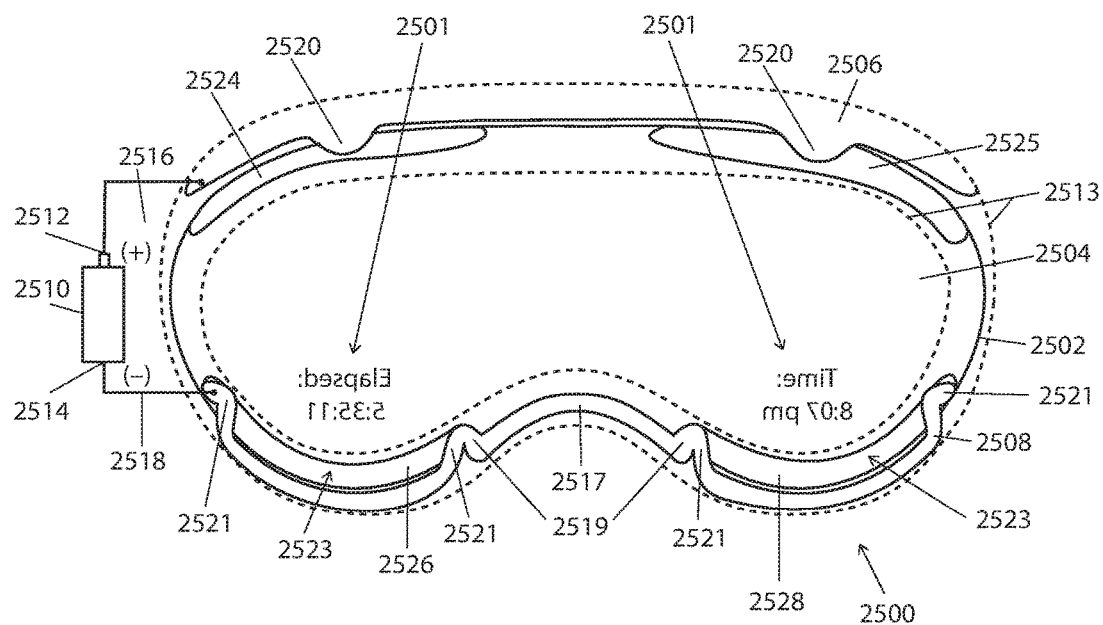
FIG. 25 is a graphical schematic representation of another alternate A/R or V/R battery-powered eye-shield electrical interconnection system in accordance with an aspect of the invention, comprising bus bars which engage the heating element of an A/R or V/R substrate via an alternative partial contact area configuration contacting painted silver ink contact pads on the heating element.

Referring now to FIG. 25, there is shown a graphic schematic representation of a front view of another alternate embodiment of an electrical interconnection system on an irregularly-shaped eye-shield 2500 adapted for use with an A/R or V/R system and in accordance with an aspect of the invention. The eye-shield 2500 comprises a thin-film heating element 2504 attached to a polycarbonate lens 2502 that is adapted for displaying visual information 2501 to a user as part of the A/R or V/R system. An upper bus bar 2506 is held in partial contact with the thin-film heating element 2504 along the peripheral upper length of the polycarbonate lens 2502 via contact pads 2524, 2525 as further described below, and a lower bus bar 2508 is held in partial contact with the thin-film heating element along the peripheral lower length of the polycarbonate lens via contact pads 2526, 2528 as further described below. A battery power source 2510 connects to upper bus bar/wire 2506 via a positive terminal 2512 and a positive circuit wire 2516, and the battery power source connects to the lower bus bar/wire 2508 via a negative terminal 2514 and a negative circuit wire 2518. These contacts are made using rivets, glue, clamps, or other method of connection.

Upper bus bar 2506 is crimped, folded, bent or otherwise provided with an altered structure or configuration, such as protrusions and/or recessions, such that there are protrusion elements 2520, or teeth-like contacts 2520, adapted for contacting the thin-film heating element 2504 through the plurality of painted-on contact pads 2524, 2525 which are preferably painted on as silver ink on the thin-film heating element in order to create a more robust and enhanced contact that is not as easily scratched, or otherwise damaged, as might be the thin-film heating element 2504 itself. The painting on of painted contact pads 2524, 2525 also provide for customized distribution of power onto the heating element 2504 of the eye-shield 2502 as shown by allowing for distribution and application of power at areas on the eye-shield where unobstructed vision, as by fog, is important and where overheating is less likely. Further, by distributing the power onto the thin-film heating element via a bus bar, preferably made of copper, having better conductivity than the painted-on silver ink pads, less losses are incurred within the system, leading to better battery efficiency. Still further, this system of distributing power throughout the system allows for an efficient manufacturing process and a minimization of human labor by allowing for an easier-to-implement and more-robust connection between the heating element 2504 and the battery 2510.

Similarly, lower bus bar 2508 is also crimped, bent, folded, snaked, or otherwise provided with an altered structure or configuration, such as protrusions and/or recessions, such as protruding protrusion contacts 2521, adapted for contacting the thin-film heating element 2504, at spaced intervals 2523, through preferably painted-on contact pads 2526, 2528, which are painted preferably with silver ink on the thin-film heating element 2504 at locations corresponding, or overlapping, with the partial contact areas (2521) of the bus bar 2508. In this embodiment of the invention, there are provided larger contact pads 2524, 2525, 2626, 2628 for interconnecting the partial contact areas 2520, 2521 of the bus bars 2506, 2508 in an efficient manner (e.g., there may be one partial contact area per contact pad as with partial contact 2520, or there also may be multiple contact areas per contact pad as with partial contacts 2521). As with other embodiments of the invention, a retaining member 2513 secures the polycarbonate lens 2502 and thin-film heating element 2504 in contact with the bus bars 2506, 2508 via the corresponding contact pads 2524, 2525, 2526, 2528, respectively, on the thin-film heating element 2504.

The irregular shape of A/R or V/R system eye-shield 2500 makes a uniform flow of current in order to prevent hot spots difficult. Thus, it is desirable, as taught by this embodiment, for the bus bars 2506, 2508 to have customizable peripheral contacts with the thin-film heating element 2504. This embodiment achieves this with a singular upper bus bar 2506 that is crimped, bent, folded, or otherwise made to snake, creating protruding elements 2520, also known as partial contact areas 2520, that make contact with the thin-film heating element 2504 through the painted-on contact pads 2524, 2525 to provide power to heat the eye shield 2500. Lower bus bar 2508 is also customizable and is crimped, bent, folded or otherwise manufactured such that it makes partial contact with thin-film heating element 2504 via the painted-on contact pads 2526, 2528.

Figure 26:
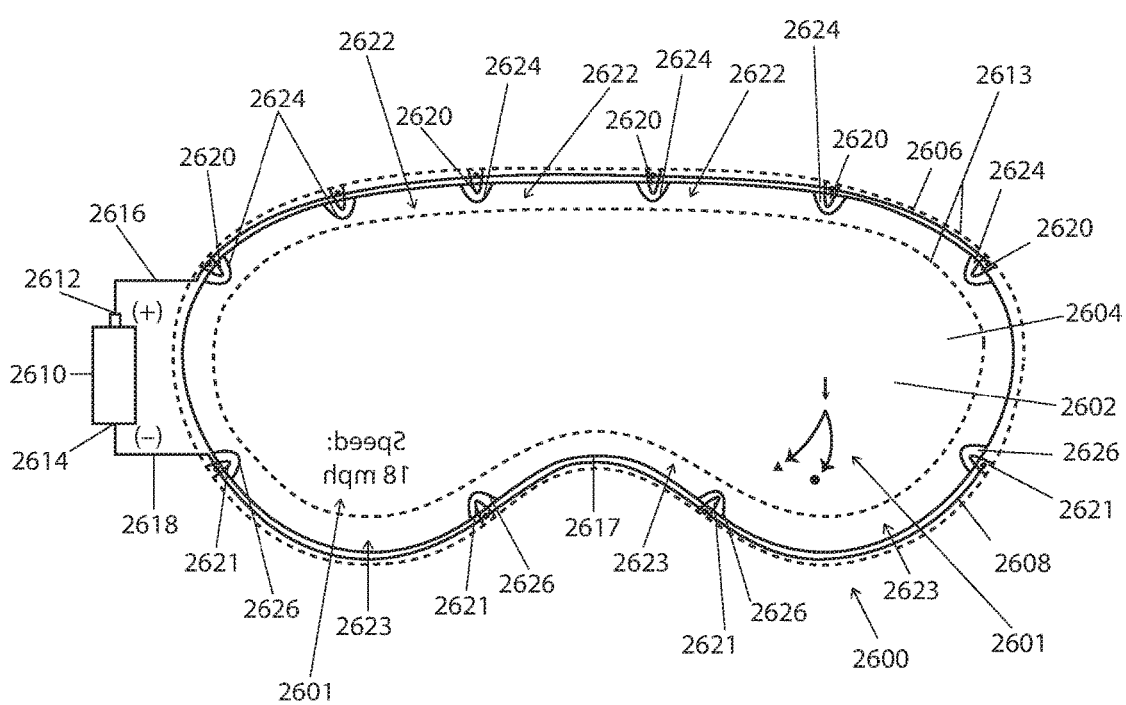
FIG. 26 is a graphic schematic representation of a front view of yet another alternate A/R or V/R battery-powered eye-shield bus bar electrical interconnection system in accordance with an aspect of the invention, comprising bus bars which engage the heating element of the eye-shield substrate via another alternative partial contact area configuration contacting another configuration of painted silver ink contact pads on the heating element.

As can be seen by comparing FIGS. 25 and 26, there are fewer contacts between the bus bar 2506 and the painted-on contact pads 2524, 2625 than there are contacts between the bus bar/wire 2606 and the heating element 2504 through painted-on contact pads 2624, illustrating how the contact system of this aspect of the invention is customizable to provide more or fewer contacts, and at varying locations, from the battery 2510 to the thin-film heating element. Further, the lower bus bar 2508 is crimped, bent, folded or otherwise manufactured as shown at 2519 to continue the bus bar at 2508 across the nose cut-out portion at 2517 such that it does not contact the thin-film heating element 2504 or any contact pad since there is no contact pad at this location, over the nose cut-out portion on the polycarbonate lens 2502. By avoiding hot spots directly over a nose cut-out portion of the eye-shield lens 2502 through such customized bus bars 2506, 2508, battery power will be conserved, and the eye-shield 2500 will be more comfortable to wear.

Referring now to FIG. 26, there is shown a graphic schematic representation of a front view of yet another alternate embodiment of an electrical interconnection system on an irregularly-shaped eye-shield 2600 adapted for use with an A/R or V/R system and in accordance with an aspect of the invention. The eye-shield 2600 comprises a thin-film heating element 2604 attached to a polycarbonate lens 2602 that is adapted for displaying visual and graphic information 2601 to a user of the system. An upper bus bar/wire 2606 is held in partial contact with the thin-film heating element 2604 along the peripheral upper length of the polycarbonate lens 2602, and a lower bus bar/wire 2608 is held in partial contact with the thin-film heating element along the peripheral lower length of the polycarbonate lens. A battery power source 2610 connects to upper bus bar/wire 2606 via a positive terminal 2612 and a positive circuit wire 2616, and the battery power source connects to the lower bus bar/wire 2608 via a negative terminal 2614 and a negative circuit wire 2618. These contacts are made using rivets, glue, clamps, or other method of connection.

Upper bus bar/wire 2606 is provided with an altered structure or configuration, such as protrusions 2620, such that there are protruding elements 2620, or teeth-like contacts 2620, adapted for contacting the thin-film heating element 2604, at spaced intervals 2622, through individual painted-on contact pads 2624 made preferably of silver ink painted on the thin-film heating element in order to create a more robust and enhanced contact that is not as easily scratched, or otherwise damaged, as might be the thin-film heating element itself.

Similarly, lower bus bar/wire 2608 is also provided with an altered structure or configuration, such as protrusions 2621, such that teeth-like contacts 2621 are adapted for contacting the thin-film heating element 2604. The protrusions 2621 are located at spaced intervals 2623, and they contact the thin-film heating element 2604 through painted-on contact pads 2626. The painted on contact pads 2626 are painted on the thin-film heating element 2604 as silver ink at location intervals corresponding with the partial contact areas 2621 of the bus bar/wire 2608. In this embodiment of the invention, there are provided smaller contact pads 2624, 2626 for interconnecting the partial contact areas 2620, 2621 of the bus bars/wires 2606, 2608 in an efficient manner. Thus these partial contact areas 2620, 2621 are shown in this embodiment as one partial contact area per contact pad. As with other embodiments of the invention, a retaining member 2613 secures the polycarbonate lens 2602 and thin-film heating element 2604 in contact with the bus bars/wires 2606, 2608 via the corresponding contact pads 2624, 2626 on the thin-film heating element 2604.

The irregular shape of A/R or V/R eye-shield 2600 makes a uniform flow of current in order to prevent hot spots difficult and this would, without an aspect of the invention, lead to unnecessarily wasted power. Thus, it is desirable, as taught by this embodiment, for the bus bars 2606, 2608 to have customizable peripheral contacts with the thin-film heating element 2604. This embodiment achieves this with multiple teeth 2620 attached to upper bus bar/wire 2606 and lower bus bar/wire 2608, creating partial contact areas 2620, 2621, respectively, that make contact with the thin-film heating element 2604 through the painted-on contact pads 2624 to allow customization of the amount of power and heat applied to the eye shield 2600. This is especially true since the partial contact areas 2620, 2621 may be located at various different locations along the periphery of the eye-shield lens 2602 to make contact with corresponding contact pads 2624, 2626.

The lower bus bar/wire 2608 provides a different customized number of partial contact areas 2621, that is a fewer number of partial contact areas than those partial contact areas 2620 above as part of the upper bus bar/wire 2606 for making partial contact with the thin-film heating element 2604. Since the lower bus bar/wire 2608 makes no contact with the thin-film heating element 2604 (or any contact pad since there is no contact pad at this location) over the nose cut-out portion at 2617 on the polycarbonate lens 2602, hot spots are avoided directly over the nose cut-out portion of the lens 2602. By avoiding hot spots directly over a nose cut-out portion of the eye-shield lens 2602 through bus bar/wire 2606, 2608, battery power will be conserved, and the A/R or V/R eye-shield 2600 will be more comfortable to wear.

Thus, in accordance with an aspect and embodiments of the invention, there are further provided at least one, and in other embodiments a plurality, of painted contact pads preferably located around the periphery of the heating element on the A/R or V/R eye-shield. Thus, there are provided bus bar interconnection systems, an eye-shield adapted for heating using a battery, and also a battery-powered eye-shield, wherein the interconnection system of the bus bar interconnection system comprises at least an upper bus bar and a lower bus bar, and in another embodiment an upper bus bar and a plurality of lower bus bars, wherein the bus bars have a plurality of protrusions, or alternatively recessions, formed therein (or a part thereof) so as to form corresponding partial contact areas for allowing contact of the bus bars with the resistive heating element of the eye-shield.

Thus, such a system in accordance with this aspect and these embodiments of the invention further comprises at least one painted-on contact pad, or in an alternate embodiment a plurality of contact pads, located strategically adjacent and around the outer periphery of the heating element, the painted-on contact pads being interposed between the partial contact area, or areas, of the bus bars and the heating element so as to provide an enhanced contact and for customized location-specific power from the battery to the heating element via the bus bars/wires, to provide even heating of the resistive heating element and to avoid hot spots on the A/R or V/R eye-shield.

The enhanced painted-on contact pads of this aspect of the invention may be provided via a silver ink painted bus bar wherein silver ink is painted onto the resistive heating element so as to make contact with the heating element, the silver ink being more robust than the heating element material, so as to avoid damage to the resistive heater/heating element by scratching from the bus bar. This in turn makes for a robust and durable contact, and the contact is preferably reinforced as in other embodiments of the invention with the use of a clamping, or otherwise engaging, peripheral channel member securing interconnection of only the partial contact areas of the bus bars/wires with the heating element. The painted-on contact pads of this aspect of the invention may be larger or smaller, depending upon the customization needs for heating of the particular area of the eye-shield lens and associated heating element. Thus, for example where less heat is required, as for example directly over the bridge of the nose of a goggle-shaped eye-shield, the painted-on contact pads may be smaller and just on either side of the nose-cut-out portion of the A/R or V/R eye-shield, whereas directly underneath the location of the eye-shield adapted to be directly in front of the eyes of a user, the painted-on contact pads may be longer to correspond with multiple contact teeth, or contact points, from the bus bar/wire (e.g., one painted contact pad to multiple bus bar protrusions), in order to help customize the application of power and to more efficiently distribute the power and prevent power losses that would otherwise occur with one contact point on one end of a longer silver ink contact pad (bus bar), it being the case that a copper bus bar is more efficient in transmitting the power than the silver ink contact pad. This in turn makes design of the system easier and saves some battery life.

Figure 27:
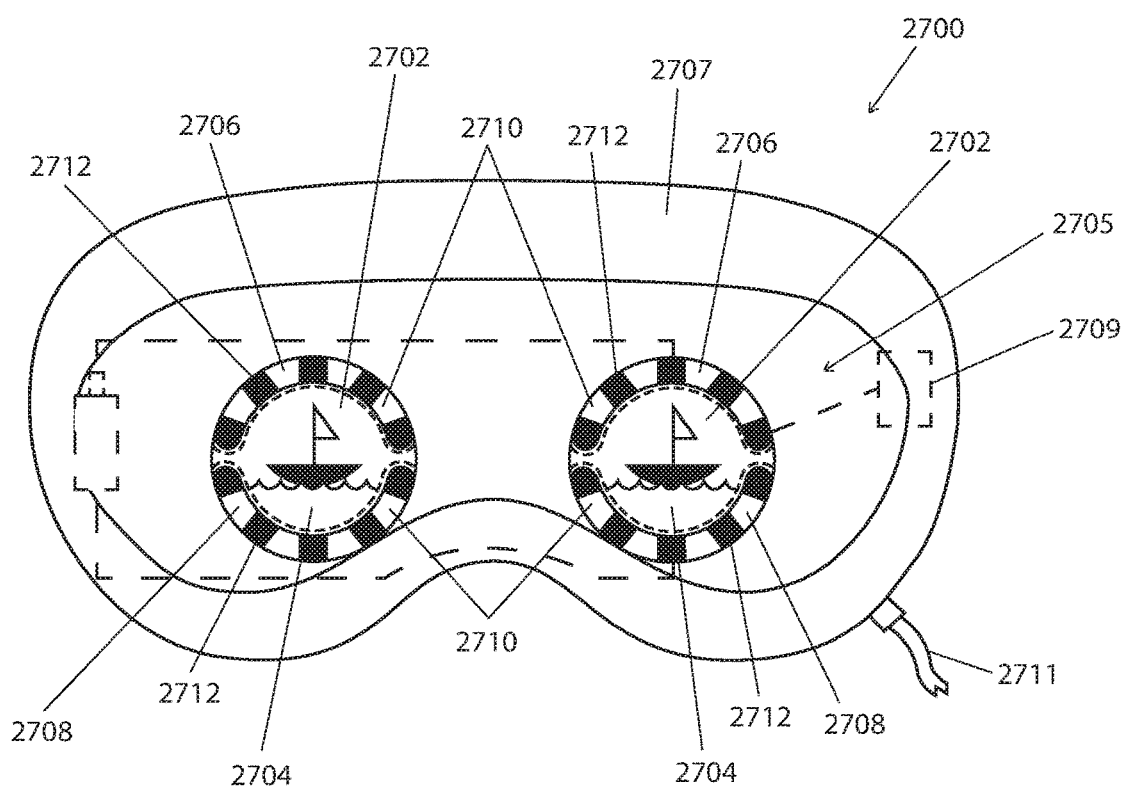
FIG. 27 is a graphic representation of a back view of a V/R system in accordance with an embodiment and aspect of the invention.

Referring now to FIG. 27, an embodiment of an aspect of the invention is illustrated showing a rear view of an inner cavity 2705 of a V/R headset system 2700 enclosed by an outer frame 2707 wherein an aspect of the invention is implemented to provide heating of circular lenses 2702 to prevent fogging of the vision screen portion of the system. The headset system 2700 comprises computing means 2709, onboard the headset portion of the system and/or on a remotely located computer to which the V/R headset system is connected via a tether I/O cord 2711, for providing sensory visual, audio, or haptic input to the user, as well as to provide and receive motion and other I/O input to and from the user to the system. Each lens 2702, adapted for displaying visual or other graphic information to the user, has a heating element 2704 deposited on the inner portion of the lens. Upper bus bars 2706 are engaged to the peripheral upper lengths of each polycarbonate lens 2702, and lower bus bars 2708 are engaged to the peripheral lower lengths of each polycarbonate lens. The upper bus bars 2706 and lower bus bars 2708 are crimped, bent, folded, or otherwise structurally diverted such that there are encroaching "hill-and-valley"-type, or teeth-like contacts 2710 adapted for contacting the heating element 2704 at spaced intervals 2712. The teeth-like contacts 2710 are longer or shorter to create more or less contact area in order to customize heating of the headset lenses 2702 to prevent fogging and to conserve power. Likewise, the spaced intervals 2712 located between the contacts 2710 are wider or narrower in order to customize heating of the headset lenses 2702 to prevent fogging and conserve power. The upper and lower bus bars 2706, 2708 are held in contact with peripheral retaining members 2703 similarly to that previously described.

Figure 28A:
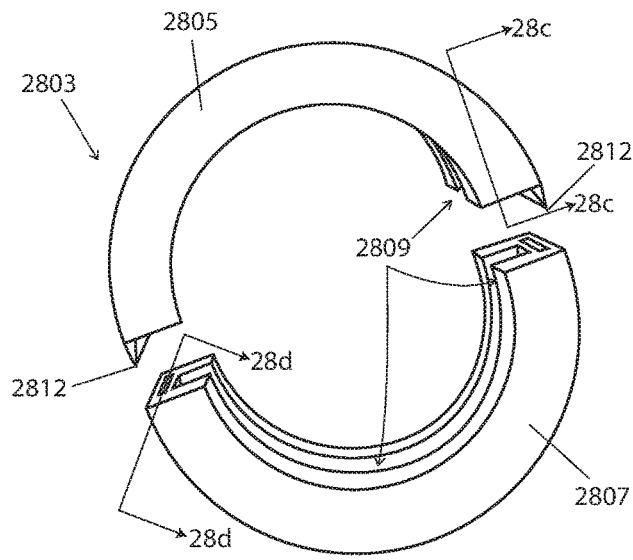
FIG. 28a is a perspective view of a clip-type, or snap-type, clamping and retaining ring-shaped channel member for holding portions of a bus bar onto a heating element, with or without painted contact pads painted on the heating element.

Referring now to FIGS. 28A-D, there are shown two embodiments of different peripheral retaining members 2803 and 2803'. In FIG. 28A, a circular peripheral retaining member 2803 is provided having upper and lower channel member halves 2805, 2807, respectively. Upper and lower channel member halves 2805, 2807, when interconnected together, create a circular block-U-shaped channel 2809 wherein the upper channel 2809 communicates with the lower channel 2809 in order to create a contiguous channel 2809 for retaining in sandwiched fashion at least one lens member (not shown—or two or more lens members in the case of a dual lens embodiment as illustrated and described in connection with FIG. 9B) having a heating element thereon, together with peripheral upper and lower bus bars (which are crimped, bent or otherwise diverted structurally to allow partial contact with the heating element), optionally contact pads painted or otherwise engaged on the lens members, and preferably a portion of the contact wiring for interconnecting the bus bars with the system battery. Thus, the block-U-shaped channel peripheral retaining member 2803 retains the foregoing lens, bus bar, optional contact pads and partial contact wiring in sandwiched contact with each other so as to provide a reliable contact between the heating element of the lens and the battery for the system.

Figure 28C:
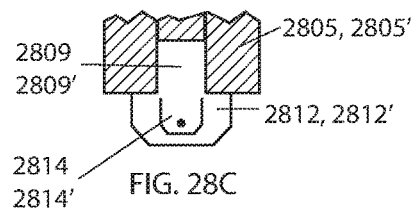
FIG. 28c is a cross-section plan view taken along line 28c-28c of either of FIG. 28a or FIG. 28b, showing a portion of a male portion of a clip-type fastener for either a ring-shaped, or goggle lens-shaped, channel member for fastening the channel member onto a lens or vision screen.
Figure 28D:
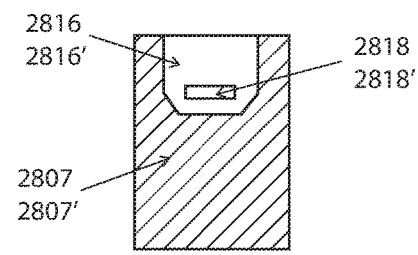
FIG. 28d is a cross-section plan view taken along line 28d-28d of either of FIG. 28a or FIG. 28b, showing a portion of a female portion of a clip-type fastener for either a ring-shaped, or goggle lens-shaped, channel member for fastening the channel member onto a lens or vision screen.
Figure 28B:
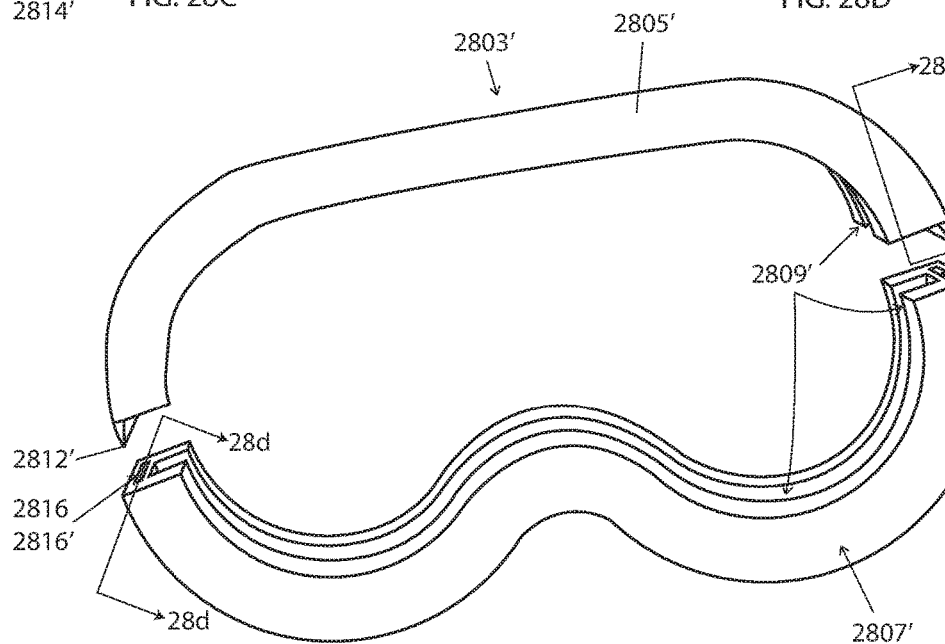
FIG. 28b is a perspective view of a clip-type, or snap-type, clamping and retaining goggle lens-shaped channel member for holding portions of a bus bar onto a heating element, with or without painted contact pads painted on the heating element.

In FIG. 28B, a goggle-lens-shaped peripheral retaining member 2803' is provided having upper and lower channel member halves 2805', 2807', respectively, formed in the shape of the periphery of a standard goggle lens. Upper and lower channel member halves 2805', 2807', when interconnected together, create a circular block-U-shaped channel 2809' wherein the upper channel 2809' communicates with the lower channel 2809' in order to create a contiguous channel 2809' for retaining in sandwiched fashion at least one lens member (not shown—or two or more lens members in the case of a dual lens embodiment as illustrated and described in connection with FIG. 9B) having a heating element thereon, together with peripheral upper and lower bus bars, optionally contact pads painted or otherwise engaged on the heating elements of the lens members, and preferably a portion of the contact wiring for interconnecting the bus bars with the system battery.

As shown in FIGS. 28C and 28D, further details are provided for the system for interconnecting and snapping together the two halves 2805, 2807 (2805', 2807') of the peripheral retaining members 2803 (2803'). FIG. 28C illustrates the male clip portions 2812, 2812' of the interconnecting system. Each male clip portion 2812, 2812' extends from an end of an upper peripheral retaining member channel half 2805, 2805', and has a spring-loaded retention clip 2814, 2814' thereon for engaging with the female portion of the interconnecting system. FIG. 29D illustrates the female receptacle portions 2816, 2816' of the interconnecting system. Each female receptacle portion 2816, 2816' is formed in an end of a lower peripheral retaining channel member half 2807, 2807', and further has a retention socket 2818, 2818' for receiving the spring-loaded retention clips 2814, 2814' of the male clip portions 2812, 2812' for snapping shut, and retaining in engaged relationship, the two halves of the peripheral retaining channel members 2805, 2805' and 2807, 2807'.

Thus, once the lens members, bus bars, contact pads and wiring are interconnected and loaded into, for example, a lower half 2807, 2807' of the peripheral retaining member 2803, 2803', the upper half 2805, 2805' of the member is snapped down onto the lower half, with the male spring-loaded retention clip 2814, 2814' engaging with the retention socket 2818, 2818', to secure the two halves of the peripheral retaining member around the sandwiched lens, bus bar, and contact pad combination, thus holding them firmly together in appropriate electrical contact. This contact is thus made without the need for gluing or otherwise connecting with rivets, screws or other means, and thereby it efficiently maintains the connection for the lens to be placed into the A/R or V/R headset device to enable contact with the battery for the device to prevent fogging of the viewing screen or lens thereof.

While a preferred embodiment of the present invention has been shown and described, it will be apparent to those skilled in the art that many changes and modifications may be made without departing from the invention in its broader aspects. For example, it will be appreciated that one of ordinary skill in the art may mix and match the various components of the various embodiments of the invention without departing from the true spirit of the invention as claimed. The appended claims are therefore intended to cover all such changes and modifications as fall within the true spirit and scope of the invention.

What is claimed is:

1. An electronic headset device adapted for being worn by a user of a virtual reality or augmented reality system and adapted for being powered by a power supply to provide at least a visual sensory experience for the user, said device comprising:

a frame adapted for housing electronics and circuitry necessary for transmitting images to the user, said frame forming at least a partial enclosure around the user's eyes;

a vision screen held in said frame adapted for displaying the images to the user;

a heating element attached to a surface of said vision screen;

an electrical interconnection system adapted for interconnecting said heating element and the power supply to enable activation of said heating element to prevent fogging of said vision screen; and a support system depending from said frame adapted for holding the headset device on a user's head a distance from the user's eyes.

2. The electronic headset device of claim 1, wherein said vision screen further comprises a plurality of generally circular lenses adapted for displaying the images to the user, wherein said heating element on said vision screen comprises a plurality of heating elements, at least one said heating element on each of said plurality of lenses; and wherein said electrical interconnection system is adapted for interconnecting each said heating element and the power supply.

3. The electronic headset device of claim 2, wherein said electrical interconnection system further comprises a plurality of bus bar electrical interconnection systems adapted for interconnecting said plurality of heating elements and said power source, each bus bar electrical interconnection system further comprising:

a plurality of bus bars, each bus bar comprising means adapted for interconnecting the bus bar with a lead from the power source, at least one of the bus bars comprising at least one protruding configuration alteration providing a partial contact surface area of the bus bars; and at least one peripheral member securing interconnection of the partial contact surface area of the bus bars with at least one of said heating elements and adapted for providing customized heating to the heating element depending upon the number of protruding configuration alterations in the at least one of the bus bars for preventing fogging of the vision screen.

4. The electronic headset device of claim 3, wherein at least one of said bus bars comprises a plurality of protruding configuration alterations so as to create a stepped partial contact surface so as to be adapted for providing a customized amount of power to be supplied to the heating element of the vision screen.

5. The electronic headset device of claim 2, wherein the electronic headset device comprises a goggle adapted for use during an augmented reality experience, and wherein the goggle lens comprises the vision screen.

6. The electronic headset device of claim 2, wherein the electronic headset device comprises part of a face shield and motor-cycle helmet combination adapted for use during an augmented reality experience, and wherein the face shield comprises the vision screen.

7. The electronic headset device of claim 2, wherein the electronic headset device comprises part of a medical face shield adapted for use during an augmented reality experience, and wherein the face shield comprises the vision screen.

8. The electronic headset device of claim 2, wherein electronic headset device comprises part of ballistic eyewear adapted for use during an augmented reality experience, and wherein the ballistic eyewear has a lens comprising the vision screen.

9. The electronic headset device of claim 1, wherein said electrical interconnection system further comprises a bus bar electrical interconnection system adapted for interconnection of said heating element and the power source, said bus bar electrical interconnection system further comprising:

a plurality of bus bars, each bus bar comprising means adapted for interconnecting the bus bar with a lead from the power source, at least one of the bus bars comprising at least one protruding configuration alteration providing a partial contact surface area of the bus bars; and at least one peripheral member securing interconnection of the partial contact surface area of the bus bars with said heating element and adapted for providing heating to the heating element for preventing fogging of the vision screen.

10. The electronic headset device of claim 9, wherein at least one of said bus bars comprises a plurality of protruding configuration alterations so as to create a stepped partial contact surface so as to be adapted for providing a customized amount of power to be supplied to the heating element of the vision screen.

11. An electronic headset device adapted for being worn by a user of a virtual reality or augmented reality system and adapted for being powered by an on-board battery power supply to provide at least a visual sensory experience for the user, said device comprising:

a frame adapted for housing electronics and circuitry necessary for transmitting images to the user, said frame forming at least a partial enclosure around the user's eyes;

a vision screen held in said frame adapted for displaying the images to the user;

a heating element attached to a surface of said vision screen;

an electrical interconnection system adapted for interconnecting said heating element and the power supply to enable activation of said heating element to prevent fogging of said vision screen, said electrical interconnection system comprising a plurality of bus bars, at least one of the bus bars having at least one protruding configuration alteration providing a partial contact surface area of the bus bars on said heating element and adapted for providing customized heating for said vision screen depending upon the location, number, and extent of protrusions, of the at least one protruding configuration alteration of the bus bars coming in contact with said heating element, said electrical interconnection system further comprising at least one peripheral member securing interconnection of the partial contact surface area of the bus bars with said at least one heating element; and a support system depending from said frame for holding the headset device on a user's head a distance from the user's eyes.

12. The electronic headset device of claim 11, wherein at least one of said bus bars comprises a plurality of protruding configuration alterations so as to create a stepped partial contact surface so as to be adapted for providing a customized amount of power to be supplied to the heating element of the vision screen.

13. The electronic headset device of claim 12, further comprising at least one upper bus bar and at least one lower bus bar, and wherein said upper bus bar comprises a plurality of protruding configuration alterations for providing a stepped partial contact surface area of the bus bars customizing the amount of power to be supplied to the heating element of the vision screen.

14. The electronic headset device of claim 11, wherein the electronic headset device comprises a goggle adapted for use during an augmented reality experience, and wherein the goggle lens comprises the vision screen.

15. The electronic headset device of claim 11, wherein the electronic headset device comprises part of a face shield and motor-cycle helmet combination adapted for use during an augmented reality experience, and wherein the face shield comprises the vision screen.

16. The electronic headset device of claim 11, wherein the electronic headset device comprises part of a medical face shield adapted for use during an augmented reality experience, and wherein the face shield comprises the vision screen.

17. The electronic headset device of claim 11, wherein the electronic headset device comprises part of ballistic eyewear adapted for use during an augmented reality experience, and wherein the ballistic eyewear has a lens comprising the vision screen.

18. An electronic headset device adapted for being worn by a user of a virtual reality or augmented reality system to provide at least a visual sensory experience for the user, said device comprising:
 a frame adapted for housing electronics and circuitry necessary for transmitting images to the user, said frame forming at least a partial enclosure around the user's eyes;
 a plurality of circular vision screen lenses in the frame and adapted for displaying the images to the user;
 a plurality of heating elements, at least one said heating element attached to a surface of each vision screen lens;
 a plurality of electrical interconnection systems, each said electrical interconnection system adapted for heating one of said heating elements, each said electrical interconnection system comprising a plurality of bus bars, at least one of the bus bars having at least one protruding configuration alteration providing a partial contact surface area of the bus bars on said heating element, each said electrical interconnection system comprising at least one peripheral member securing interconnection of the partial contact surface area of the bus bars with said heating element; and
 a support system depending from said frame for holding the headset device on a user's head a distance from the user's eyes.

19. The electronic headset device of claim 18, wherein at least one of said bus bars comprises a plurality of protruding configuration alterations so as to create a stepped partial contact area so as to be adapted for providing a customized amount of power to be supplied to one of said heating elements of the vision screen lenses.

20. The electronic headset device of claim 19, further comprising at least one painted contact pad, said at least one painted contact pad located on one of said heating elements, said at least one painted contact pad being interposed between the stepped partial contact area of said at least one of said bus bars and said heating element.

* * * * *